US008835422B2

(12) United States Patent
O'Connor et al.

(10) Patent No.: US 8,835,422 B2
(45) Date of Patent: Sep. 16, 2014

(54) SUBSTITUTED IMIDAZOHETEROCYCLE DERIVATIVES

(75) Inventors: Stephen J. O'Connor, Guilford, CT (US); Jason S. Newcom, Norfolk, MA (US); Janet L. Ralbovsky, Memphis, TN (US); Gary R. Gustafson, Ridgefield, CT (US); R. Paul Beckett, Yorktown Heights, NY (US); Robert Zhiyong Luo, New City, NY (US)

(73) Assignee: Cara Therapeutics, Inc., Shelton, CT (US)

( * ) Notice: Subject to any disclaimer, the term of this patent is extended or adjusted under 35 U.S.C. 154(b) by 351 days.

(21) Appl. No.: 13/126,201

(22) PCT Filed: Dec. 1, 2009

(86) PCT No.: PCT/US2009/066172
§ 371 (c)(1),
(2), (4) Date: Apr. 27, 2011

(87) PCT Pub. No.: WO2010/068520
PCT Pub. Date: Jun. 17, 2010

(65) Prior Publication Data
US 2012/0015930 A1    Jan. 19, 2012

Related U.S. Application Data

(60) Provisional application No. 61/121,758, filed on Dec. 11, 2008.

(51) Int. Cl.
*A61K 31/553* (2006.01)
*C07D 498/04* (2006.01)
*C07D 487/04* (2006.01)

(52) U.S. Cl.
CPC ............ *C07D 487/04* (2013.01); *A61K 31/553* (2013.01); *C07D 498/04* (2013.01)
USPC ........................................ 514/211.1; 540/552

(58) Field of Classification Search
USPC ........................................ 514/211.1; 540/552
See application file for complete search history.

(56) References Cited

PUBLICATIONS

Pertwee, Roger G., The Therapeutic Potential of Drugs That Target Cannabinoid Receptors or Modulate the Tissue Levels or Actions of Endocannabinoids, The AAPS Journal, vol. 7, pp. E625-E654, 2005.*
Mackie et al., CB2 Cannabinoid Receptors: New Vistas, British Journal of Pharmacology, vol. 153, pp. 177-178, 2008.*
Mackie, Ken, Cannabinoid Receptors As Therapeutic Targets, Annu. Rev. Pharmacol. Toxicol., vol. 46, pp. 101-122, 2006.*
Hanus, Lumir O., Discovery and Isolation of Anandamide and Other Endocannabinoids, Chemistry & Biodiversity, vol. 4, pp. 1828-1841, 2007.*

* cited by examiner

*Primary Examiner* — Brenda Coleman
(74) *Attorney, Agent, or Firm* — Algis Anilionis; F. Chau & Associates, LLC

(57) ABSTRACT

The present invention provides substituted imidazoheterocycles having the general structure of formula I:

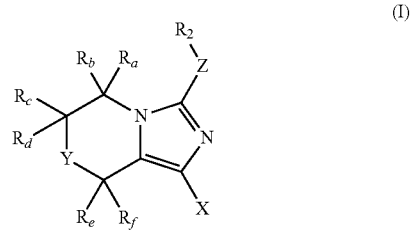

wherein Y is chosen from —O—, —OCR$_g$R$_h$—, —CR$_g$R$_h$O—, —CR$_g$R$_h$—, —(CR$_g$R$_h$)$_2$—, —NR$_i$—, —CR$_g$R$_h$NR$_i$— and —NR$_i$CR$_g$R$_h$—. Also provided are pharmaceutically acceptable salts, acid salts, hydrates, solvates and stereoisomers of the compounds of formula I. The compounds are useful as modulators of cannabinoid receptors and for the prophylaxis and treatment of cannabinoid receptor-associated diseases and conditions, such as pain, inflammation and pruritis.

9 Claims, No Drawings

SUBSTITUTED IMIDAZOHETEROCYCLE DERIVATIVES

RELATED APPLICATION

This application claims the benefit of PCT/US2009/066172 filed 1st Dec. 2009, which in turn claims the benefit of provisional application U.S. Ser. No. 61/121,758 filed on 11 Dec. 2008; the specifications of each of these applications are hereby incorporated by reference in their entireties.

FIELD OF THE INVENTION

The invention relates to substituted imidazoheterocycles, and more particularly to substituted 5,6,7,8-tetrahydroimidazo[1,5-a]pyrazines; 6,8-dihydro-5H-imidazo[5,1-c][1,4]oxazines; and 5,6,7,8-tetrahydroimidazo[1,5-a]pyridines, as well as substituted 6,7,8,9-tetrahydro-5H-imidazo[1,5-a][1,4]diazepines; 5,6,7,9-tetrahydroimidazo[5,1-c][1,4]oxazepines; 5,6,8,9-tetrahydroimidazo[1,5-d][1,4]oxazepines; and 6,7,8,9-tetrahydro-5H-imidazo[1,5-a]azepines and the use of these compounds in the prophylaxis and treatment of cannabinoid receptor-associated diseases, disorders and conditions, such as pain, inflammation and pruritis.

BACKGROUND OF THE INVENTION

Classical cannabinoids such as the marijuana-derived compound $\Delta^9$-tetra-hydrocannabinol, ($\Delta^9$-THC) exert their pharmacological effects through interaction with specific members of the G-protein coupled receptor (GPCR) family. Two cannabinoid receptors have been cloned and characterized: CB1, a receptor found in the mammalian brain and to a lesser extent in peripheral tissues; and CB2, a receptor found primarily in the peripheral tissues, particularly in cells of the immune system. Several endogenous ligands for these cannabinoid receptors, known as endocannabinoids, have been identified. For a review see Hanus, L. O., *Discovery and isolation of anandamide and other endocannabinoids*, Chem. Biodivers. (2007) 8:1828-41.

Compounds that are modulators of one or both of the cannabinoid receptors have been shown to produce a variety of pharmacological effects that may be of therapeutic benefit in humans (see, for example, Mackie, K., *Cannabinoid receptors as therapeutic targets*, Ann. Rev. Pharmacol. Toxicol. (2006) 46: 101-122; Pertwee, R. G., *The therapeutic potential of drugs that target cannabinoid receptors or modulate the tissue levels or actions of endocannabinoids*, AAPS J. (2005) 7:E625-654). The cannabinoid receptor modulator can be an agonist, an inverse agonist or a neutral antagonist, and may interact at the same (orthosteric) site as the endogenous ligand, or at a different (allosteric) site.

Activation of the CB1 receptor in the brain is believed to mediate undesirable psychotropic effects associated with $\Delta^9$-THC and other centrally acting cannabinoid ligands. As a result, there has been considerable interest in developing compounds that possess high affinity and selectivity for the CB2 receptor (see for example, Raitio, K. H. et al., *Targeting the Cannabinoid CB2 Receptor: Mutations, Modelling and Development of selective CB2 ligands*, Curr. Med. Chem. (2005) 12: 1217-37). CB2 receptor agonists have shown efficacy in preclinical models of neuropathic and inflammatory pain and may also find application in cancer, multiple sclerosis, osteoporosis, Alzheimer's disease, liver disease and diabetes (Mackie, K.; Ross R A; *CB2 cannabinoid receptors: new vistas*, Br. J. Pharmacol. (2008) 153: 177-78 and references cited therein). There is an ongoing need to identify new cannabinoid receptor ligands that exhibit improved drug-like properties. In addition there is a need for new cannabinoid ligands that are restricted to the periphery with low or minimal effects on the central nervous system (CNS).

SUMMARY OF THE INVENTION

The present invention provides compounds of the structure of formula I:

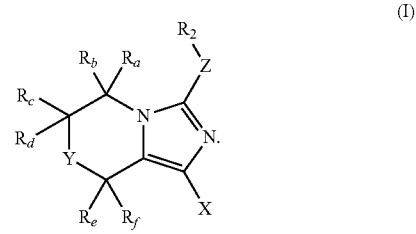

(I)

In formula I: X is chosen from —(CO)$R_1$ and a 5-, 6-, 7-, 8-, 9- or 10-membered heterocyclyl group; Y is chosen from —O—, —OCR$_g$R$_h$—, —CR$_g$R$_h$O—, —CR$_g$R$_h$—, —(CR$_g$R$_h$)$_2$—, —NR$_i$—, —CR$_g$R$_h$NR$_i$— and —NR$_i$CR$_g$R$_h$—; Z is chosen from a bond, —(CH$_2$)$_p$—, —CH=CH—, —C≡C—, —CONH—; —NHCO— and —CO—; and the radicals R$_a$, R$_b$, R$_c$, R$_d$, R$_e$, R$_f$, R$_g$ and R$_h$ are each independently —H or C$_1$-C$_8$ alkyl.

The radical R$_i$ is chosen from —H, C$_1$-C$_8$ alkyl, C$_3$-C$_6$ alkenyl, C$_3$-C$_6$ alkynyl, —(CH$_2$)$_q$aryl, C$_3$-C$_8$ cycloalkyl, C$_3$-C$_8$ cycloalkenyl, —SO$_2$R$_3$, —COR$_3$, —CONR$_3$R$_4$, —CSNR$_3$R$_4$, —COOR$_3$ and —(CH$_2$)$_q$hetero-cyclyl, wherein the alkyl, cycloalkyl, cycloalkenyl, aryl and heterocyclyl of R$_i$ are each optionally substituted with one to four substituents independently chosen from halo, —OH, oxo, —NH$_2$, —NO$_2$, —CN, —COOH, —COR$_3$, —OCF$_3$, —CF$_3$, C$_1$-C$_6$ alkyl, C$_1$-C$_4$ alkoxy, C$_3$-C$_8$ cycloalkyl, phenyl, trifluoro-methoxy and trifluoromethyl.

In formula I the radical R$_1$ is chosen C$_1$-C$_8$ alkyl, C$_2$-C$_8$ alkenyl, aryl, —NR$_5$R$_6$,

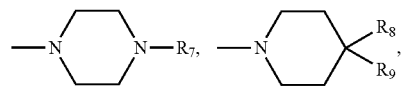

and 5-, 6-, 7, 8-, 9- and 10-membered heterocyclyl; wherein the alkyl, alkenyl, aryl and heterocyclyl of R$_1$ are each optionally substituted with one to three substituents independently chosen from C$_1$-C$_6$ alkyl, C$_2$-C$_6$ alkenyl, C$_3$-C$_6$ cycloalkyl, C$_1$-C$_6$ alkoxy, aryl, 5-, 6-, and 7-membered heterocyclyl, halo, —OH, —NH$_2$, —CN and —NO$_2$.

The radical R$_2$ is chosen —H, halo, C$_1$-C$_6$ alkyl, C$_2$-C$_6$ alkenyl, C$_2$-C$_6$ alkynyl, C$_3$-C$_{10}$ cycloalkyl, C$_3$-C$_8$ cycloalkenyl, C$_1$-C$_4$ alkoxy, aryl, 5- to 10-membered heterocyclyl; wherein the C$_2$-C$_6$ alkenyl, C$_2$-C$_6$ alkynyl, C$_3$-C$_{10}$ cycloalkyl, C$_3$-C$_8$ cycloalkenyl, aryl, 5- to 10-membered heterocyclyl of R$_2$ are optionally substituted with one to five substituents independently chosen from C$_1$-C$_6$ alkyl, C$_1$-C$_6$ alkoxy, C$_1$-C$_6$ haloalkyl, C$_1$-C$_6$ haloalkoxy, C$_3$-C$_8$ cycloalkyl, C$_4$-C$_8$ cycloalkenyl, halo, —OH, —NH$_2$, (A)(A')(A")(A''')aryl, (A)(A')(A")(A''')heterocyclyl, NR$_{14}$R$_{15}$, (CH$_2$)$_p$NR$_{14}$R$_{15}$, —CN, —NO$_2$, oxo, —COOR$_{14}$, SOR$_{14}$, SO$_2$R$_{14}$, SO$_2$NR$_{14}$R$_{15}$, NR$_{15}$SO$_2$R$_{16}$, COR$_{14}$, CONR$_{14}$R$_{15}$ and NR$_{15}$COR$_{16}$;

wherein (A), (A'), (A") and (A''') are each an independently chosen from —H and $C_1$-$C_6$ alkyl; and each heterocyclyl of (A)(A')(A")(A''')heterocyclyl is independently a 5- to 10-membered heterocyclyl.

The radical $R_3$ and $R_4$ are each independently chosen from —H, $C_1$-$C_6$ alkyl, $C_3$-$C_6$ alkenyl, $C_3$-$C_6$ alkynyl, $C_3$-$C_8$ cycloalkyl, $C_3$-$C_8$ cycloalkenyl, aryl, 4-, 5-, 6-, 7- and 8-membered heterocyclyl.

The radical $R_5$ is chosen from —H, $C_1$-$C_6$ alkyl and $C_1$-$C_6$ haloalkyl; wherein the alkyl and haloalkyl of $R_5$ are optionally substituted with one to four substituents independently chosen from $C_1$-$C_6$ alkoxy, —OH, —$NH_2$ and —CN.

The radical $R_6$ is chosen from —H, —$CR_{10}R_{11}R_{12}$, —$CR_{10}R_{11}COR_{13}$, $C_1$-$C_8$ alkyl, $C_3$-$C_{10}$ cycloalkyl, aryl, 5-, 6-, 7-, 8-, 9- and 10-membered heterocyclyl; wherein the alkyl, cycloalkyl, aryl, and heterocyclyl of $R_6$ are optionally substituted with one to three substituents independently chosen from $C_1$-$C_6$ alkyl, aryl, halo, —OH, $C_1$-$C_6$ alkoxy, $C_1$-$C_6$ hydroxyalkyl, —$COR_{13}$, —$SO_2R_{11}$, —$SO_2NR_8R_9$, —$NH_2$, —CN and —$NO_2$; alternatively, $R_5$ and $R_6$ taken together with the nitrogen atom to which they are bonded form a 5-, 6-, 7-, 8-, 9- or 10-membered heterocyclyl, which heterocyclyl substituent of $R_6$ is optionally substituted with one to two substituents independently chosen from —$CONR_1R_2$ and oxo.

The radical $R_7$ is chosen from —H, $C_1$-$C_6$ alkyl, $C_1$-$C_6$ haloalkyl, —$COR_3$, —$COOR_3$, —$SO_2R_3$, and 5-, 6-, 7-, 8-, 9- and 10-membered heterocyclyl.

The radicals $R_8$ and $R_9$ are independently chosen from —H, $C_1$-$C_6$ alkyl, $C_1$-$C_6$ haloalkyl, $C_1$-$C_6$ alkoxy, $C_2$-$C_6$ alkenyl, $C_3$-$C_6$ cycloalkyl, aryl, 5-, 6-, 7-, 8-, 9-, 10-membered heterocyclyl, halo, —OH, —$CONH_2$, —$NH_2$, —CN and —$NO_2$.

In a first alternative, $R_8$ and $R_9$, taken together with the nitrogen atom to which they are bonded form a heterocyclyl ring which is optionally substituted with one to three substituents chosen from $C_1$-$C_6$ alkyl, halo, oxo and aryl.

In a second alternative, $R_8$ and $R_9$, taken together with the carbon atom to which they are bonded form a cycloalkyl which is optionally substituted with one to three substituents chosen from $C_1$-$C_6$ alkyl, halo, oxo and aryl.

The radical $R_{10}$ is —H or $C_1$-$C_6$ alkyl.

The radical $R_{11}$ is chosen from —H, $C_1$-$C_8$ alkyl, $C_2$-$C_6$ alkenyl, $C_2$-$C_6$ alkynyl, $C_3$-$C_{10}$ cycloalkyl, aryl, 5-, 6-, 7-, 8-, 9-, and 10-membered heterocyclyl; wherein the alkyl, alkenyl, alkynyl, cycloalkyl, aryl and heterocyclyl of $R_{11}$ are optionally substituted with one to three substituents independently chosen from $C_1$-$C_4$ alkyl, $C_3$-$C_6$ cycloalkyl, aryl, and 5- to 10-membered heterocyclyl, halo, —OH, $C_1$-$C_6$ alkoxy, —$NH_2$, -guanidino, —CN, —$NO_2$, oxo, —$COOR_{10}$, —$CONR_8R_9$, —$SO_2NR_8R_9$, —$SR_{10}$, —$SOR_4$ and —$SO_2R_4$.

The radical $R_{12}$ is chosen from —H, $C_1$-$C_6$ alkyl and $C_1$-$C_6$ hydroxyalkyl.

The radical $R_{13}$ is —$NR_8R_9$ or —$OR_{10}$.

The radicals $R_{14}$, $R_{15}$ and $R_{16}$ are each independently —H, or $C_1$-$C_6$ alkyl; alternatively, $R_{14}$ and $R_{15}$ taken together with the nitrogen atom to which they are bonded form a heterocyclyl chosen from 5- to 10-membered heterocyclyl.

In formula I, the operator, p is an integer from 1 to 6; and the operator, q is zero or an integer from 1 to 4.

In the compounds of formula I, each of the following exclusions apply:

(1) When the linker, Z is a bond, or —CO—, then the radical $R_2$ is not —H.

(2) When the ring component, Y is —$CR_gR_h$—; the linker Z is —CO—, and each and every one of $R_a$, $R_b$, $R_c$, $R_d$, $R_e$, $R_f$, $R_g$, and $R_h$ is —H, and the radical $R_2$ is a 10-membered heterocyclyl, then the 10-membered heterocyclyl of $R_2$ is not substituted with both phenyl and hydroxyl.

(3) When the ring component, Y is —$CR_gR_h$—; and the linker Z is a bond; and each and every one of $R_a$, $R_b$, $R_c$, $R_d$, $R_e$, $R_f$, $R_g$, and $R_h$ is —H; and the radical $R_2$ is methyl; and X is —$(CO)R_1$; then the radical $R_1$ is not methyl.

(4) When the ring component, Y is —$(CR_gR_h)_2$—; and the linker Z is a bond; and each and every one of $R_a$, $R_b$, $R_c$, $R_d$, $R_e$, $R_f$, $R_g$, and $R_h$ is —H; and the radical, X is —$(CO)R_1$; then radical $R_2$ is not 3-fluorophenyl, 4-methylphenyl, or 4-chlorophenyl.

(5) When the ring component, Y is —$NR_i$—, —$(NR_iCH_2)$— or —$(CH_2NR_i)$—, then at least one of $R_a$, $R_b$, $R_c$, $R_d$, $R_e$, $R_f$, $R_g$, and $R_h$ is not —H.

The present invention also provides pharmaceutically acceptable salts, acid salts, stereoisomers and mixtures of stereoisomers of compounds of formula I.

The many embodiments of the compounds of formula I of the invention exhibit useful properties related to their activities as ligands of cannabinoid receptors and the biological consequences of binding to these receptors.

In particular embodiments of the invention, the compounds of formula I bind one or more cannabinoid receptors, such as without limitation, CB1 and CB2. Such compounds include those that can be classified as agonists, partial agonists or inverse agonists for a particular cannabinoid receptor and in certain embodiments these compounds exhibit selectivity for the CB2 receptor over the CB1 receptor. In one aspect, the cannabinoid receptor is a mammalian cannabinoid receptor, such as a human cannabinoid receptor, which can be, including but not limited to, a human CB1 or a human CB2 receptor.

The invention also provides compounds and pharmaceutical compositions useful for the prophylaxis and treatment of a CB2-associated and/or CB1-associated disease or condition. The pharmaceutical compositions include a compound of formula I and a pharmaceutically acceptable vehicle, diluent, excipient or carrier.

The invention further provides a method of prophylaxis or treatment of a CB2-associated disease or condition by administering a compound of formula I or a pharmaceutically acceptable salt, acid salt hydrate, solvate, stereoisomer, or mixture of stereoisomers thereof. In another embodiment, the invention provides a method of prophylaxis or treatment of a CB2-associated and/or CB1-associated disease, disorder or condition by administering a compound of formula I or a pharmaceutically acceptable salt, acid salt hydrate, solvate, stereoisomer or mixture of stereoisomers thereof. Such CB2-associated diseases or conditions and CB1-associated and CB2-associated diseases, disorders and conditions include, without limitation, pain and inflammation, wherein such pain can be inflammatory pain, visceral pain, neuropathic pain or hyperalgesia. Each of these types of pain can present as acute or chronic pain.

DETAILED DESCRIPTION OF THE INVENTION

The following terms are used in this specification:

Alkyl—a saturated branched or straight chain monovalent hydrocarbon radical of a specified number of carbon atoms. Thus, the term alkyl includes, but is not limited to, methyl, ethyl, propyl, isopropyl, n-butyl, t-butyl. A chain of one to six carbon atoms is also herein interchangeably designated as $C_1$-$C_6$ alkyl; a chain of three to six carbon atoms can be alternatively designated as $C_3$-$C_6$ alkyl and so on.

Alkenyl—refers to branched or straight chain hydrocarbon radical having at least one double bond between two carbon atoms. It should be noted that in an alkenyl substituted nitrogen, the unsaturated carbon atom cannot be bound directly to the nitrogen atom, i.e. there must be at least one unsaturated carbon (—CH$_2$— or —CR'R"—) intervening between the nitrogen atom and the nearest unsaturated carbon atom.

Alkynyl—refers to branched or straight chain hydrocarbon radical having at least one triple bond between two carbon atoms. It should be noted that in an alkynyl substituted nitrogen, the unsaturated carbon atom cannot be bound directly to the nitrogen atom, i.e. there must be at least one unsaturated carbon (—CH$_2$— or —CR'R"—) intervening between the nitrogen atom and the nearest unsaturated carbon atom.

Haloalkyl—an alkyl group having one or more hydrogen atoms substituted with a halogen atom, each independently chosen such that a haloalkyl group having more than one halogen atom can be a mixed haloalkyl, such as for instance, 2-fluoro, 2-chloroethyl, or perhalo as in trifluoromethyl.

Alkoxy—refers to an (alkyl)$_a$-O-(alkyl)$_b$ substituent group wherein a is zero or an integer, and b is an integer and the alkyl group is as defined above. So that for instance alkoxy can be and without limitation, —O-methyl, O-ethyl, —O-propyl, —(CH$_2$)$_a$O-methyl, —(CH$_2$)$_a$O-ethyl, —(CH$_2$)$_a$—O-propyl, and so forth.

Cycloalkyl—a saturated monocyclic, polycyclic or bridged hydrocarbon ring system radical or linking group. In a substituted cycloalkyl ring, the substituent is bonded to ring carbon atom replacing a hydrogen atom. The term C$_3$-C$_{10}$ cycloalkyl is herein used to designate a ring of three to ten carbon atoms, or a ring of three of more carbon atoms with the remaining carbon atoms forming one or more alkyl substituents of the ring. Similarly, a C$_3$-C$_7$ cycloalkyl designates a saturated or partially unsaturated carbocycle, although not all the designated number of carbon atoms are necessarily ring carbon atoms. Cycloalkyl typically includes, but is not limited to, cyclopropyl, cyclobutyl, cyclopentyl, cyclohexyl, cyclohexenyl, cycloheptyl and cyclooctyl. However, C$_{10}$ cycloalkyl includes 1,3,3-trimethylbicyclo[2.2.1]heptyl, wherein seven of the ten designated carbon atoms form the seven-membered bicyclo-carbocycle and the remaining three are methyl substituents.

Cycloalkenyl—partially unsaturated monocyclic, polycyclic or bridged hydrocarbon ring system radical or linking group having at least one double bond between two carbon atoms. In a substituted cycloalkenyl ring, the substituent is bonded to ring carbon atom replacing a hydrogen atom. The term C$_3$-C$_{10}$ cycloalkenyl is herein used to designate a ring of three to ten carbon atoms, or a ring of three or more carbon atoms with the remaining carbon atoms forming one or more alkyl substituents of the ring. Similarly, C$_3$-C$_7$ cycloalkenyl designates as partially unsaturated carbocycle, although not all the designated number of carbon atoms are necessarily ring carbon atoms. Cycloalkenyl typically includes, but is not limited to, cyclopentenyl, cyclohexenyl, cycloheptenyl.

Heterocyclyl—a saturated, partially unsaturated or unsaturated monocyclic, polycyclic or bridged hydrocarbon ring system radical or linking group, wherein at least one ring carbon atom has been replaced with a heteroatom selected from nitrogen, oxygen and sulfur. A heterocyclyl ring system further includes a ring system having one, two, three or four nitrogen ring atoms, or a ring system having zero, one, two or three nitrogen ring atoms and one oxygen or sulfur ring atom. The heterocyclic ring system can include more than one ring heteroatom, wherein one heteroatom is nitrogen and the other is selected from nitrogen, oxygen and sulfur. A heterocyclyl radical is derived by the removal of one hydrogen atom from a single carbon or nitrogen ring atom. Heterocyclyl includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl, imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyranyl, 4H-pyranyl, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, diazepinyl, indolizinyl, indolyl, isoindolyl, 3H-indolyl, indolinyl, benzo[b]furyl, benzo[b]thienyl, 1H-indazolyl, benzimidazolyl, benzothiazolyl, purinyl, 4H-quinolizinyl, quinolinyl, isoquinolinyl, cinnolinyl, phthalzinyl, quinazolinyl, quinoxalinyl, 1,8-napthyridinyl, pteridinyl, quinuclidinyl.

Heterocyclyl—as used herein, also includes an aromatic heterocycle such as pyrrolyl, pyrazolyl, imidazolyl, triazolyl, oxazolyl, isoxazolyl, thiazolyl, isothiazolyl, furyl, thienyl, pyridyl, pyrazinyl, pyrimidinyl, and can be optionally substituted by alkyl. Arylalkyl—an optionally substituted aryl group attached to the end carbon atom of C$_1$-C$_4$ alkyl group. As used herein "heterocyclyl" also includes bicyclic heterocyclyl radicals in which one or both rings are heterocyclic, such as for example, but not limited to imidazopyrazinyl, benzofuranyl, benzodioxolyl, benzothiophenyl, and quinolinyl.

Aryl—an unsaturated, π-electron conjugated monocyclic or polycyclic hydrocarbon ring system radical or linking group of six, eight, ten or fourteen carbon atoms. An aryl radical is derived by the removal of one hydrogen atom from a single carbon ring atom. Aryl includes, but is not limited to, phenyl, naphthalenyl, azulenyl, anthracenyl.

Aminosulfonylalkyl—a radical of the formula —NHSO$_2$-alkyl. Sulfonylaminoalkyl—a linking group of the formula —SO$_2$NH-alkyl- or a radical of the formula —SO$_2$N(alkyl)$_2$. Alkylcarbamoyl—a linking group of the formula -alkyl-C(O)NH— or a radical of the formula -alkyl-C(O)NH$_2$. Carbamoylalkyl—a linking group of the formula —NHC(O)-alkyl- or a radical of the formula —NHC(O)-alkyl.

Halogen—fluoro, chloro, bromo or iodo. Carboxyl—a radical of the formula —COOH. Hydroxyl—a radical of the formula —OH. Cyano—a radical of the formula —C≡N. Oxo—a radical of the formula =O in which the oxygen atom is double-bonded. Amino—a radical of the formula —NH$_2$ or a linking group having the formula —NH—. Aminoalkyl—a radical of the formula —NH-alkyl or —N(alkyl)$_2$.

As used herein, the terms: compound, salt, polymorph, isomer, solvate are also interchangeably referred to in the plural form.

The compounds of the present invention can contain one or more stereogenic centers, depending upon the location and nature of the various substituents desired. These stereogenic centers may be present in the (R) or (S) configuration, resulting in racemic mixtures and/or diastereomeric mixtures. Substituents on a partially or fully saturated ring may also be present in either cis or trans form. All such configurations (including enantiomers and diastereomers) of the compounds described or exemplified herein, are contemplated within the scope of the present invention. Compounds of the invention can also exist as individual stereoisomers or as mixtures in varying ratios (e.g. enantiomerically enriched or racemates). Enantiomeric mixtures of the compounds may be partially or fully resolved through standard purification and/or separation techniques known in the art, including but not limited to chiral chromatography (e.g. chiral derivatized solid phase), formation and separation of diastereomeric salts (e.g. tartaric acid salts or camphorsulfonic acid salts), or enzymatic separation. Diastereomeric mixtures can be separated by techniques well known in the art, based on their physical and/or chemical differences, or by methods described above.

In this specification, salts of a compound of formula I refers to a complex of the compound with an inorganic or organic counter ion or counter ions. For examples, see Handbook of Pharmaceutical Salts: Properties, Selection and Use; Stahl P. H., Wermuth, C. G., Eds.; John Wiley and Sons, 2002. Pharmaceutically useful salts include those obtained by treating the compound, functioning as a base, with an inorganic or organic acid to form a salt or salts. Additional pharmaceutically useful salts are those listed in U.S. Pat. No. 7,517,874.

As used herein, the term "solvates" describes a complex wherein the compound is coordinated with a proportional amount of a solvent molecule. Specific solvates, wherein the solvent is water, is referred to as hydrates. Combinations of a drug and propylene glycol(1,2-propanediol) have been used to form pharmaceutical drug solvates. See for example U.S. Pat. No. 3,970,651. Other suitable solvates are hydrates of drug compounds. Such hydrates include hydrates which either have comparable activity or hydrates which are converted back to the active compound following administration.

The present invention also contemplates pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients.

The compounds of the present invention described and exemplified herein modulate a signal that regulates a biological activity, by modulating the activity of a cannabinoid receptor. Modulation of a cannabinoid receptor can be effected by a compound of the present invention acting as an agonist, a partial agonist, inverse agonist or an antagonist upon binding at a cannabinoid receptor such as CB2 and/or CB1. The modulation of a cannabinoid receptor can be activation by compound of the present invention acting an agonist. Alternatively, the modulation of a cannabinoid receptor can be inhibition or deactivation by an antagonist. One particular signal regulated by CB2 is the intracellular concentration of cyclic adenosine monophosphate (cAMP).

The term 'agonist' as used herein means a molecule that produces a physiological response by activating a receptor.

The term 'inverse agonist' as used herein means a molecule that tends to reverse the effect of an agonist. Current theory holds that this occurs due to the higher affinity of the inverse agonist for binding the inactive conformation over the active conformation of the receptor.

The term 'antagonist' as used herein means a molecule that binds a receptor and thereby interferes with the interaction of an agonist and its cognate receptor, or blocks the constitutive activity of the receptor.

The term 'neutral antagonist' as used herein means a molecule that binds a receptor with equal affinity for the active and inactive conformations and thereby inhibits receptor activity by competing with an agonist.

In one embodiment of the compounds of the present invention of formula I when Y is —$CR_gR_h$—, Z is —CO—, $R_a$, $R_b$, $R_c$, $R_d$, $R_e$, $R_f$, $R_g$, and $R_h$ are each —H, and $R_2$ is aryl provided that the aryl of $R_2$ is not substituted with both phenyl and hydroxyl.

In another embodiment of the compounds formula I when Y is —$CR_gR_h$—, Z is a bond, $R_a$, $R_b$, $R_c$, $R_d$, $R_e$, $R_f$, $R_g$, and $R_h$ are each —H, $R_2$ is methyl, X is —(CO)$R_1$, provide that $R_1$ is not methyl.

In another embodiment when Y is —($CR_gR_h$)$_2$—, Z is a bond, $R_a$, $R_b$, $R_c$, $R_d$, $R_e$, $R_f$, $R_g$, and $R_h$ are each —H, X is —(CO)$R_1$, and $R_2$ is halophenyl, but not 3-fluorophenyl, 4-methylphenyl, or 4-chlorophenyl.

In another embodiment when Y is —$NR_i$—, —($NR_iCH_2$)— or —($CH_2NR_i$)—, then at least one of $R_a$, $R_b$, $R_c$, $R_d$, $R_e$, $R_f$, $R_g$, and $R_h$ is $C_1$-$C_8$ alkyl.

In one embodiment of the compounds of the present invention of formula I the linking group, Z is —($CH_2$)$_p$, —CH=CH—, —C≡C—, —CONH—; —NHCO—, or —CO—, and the radical $R_2$ is chosen from halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, 5-, 6-, 7-, 8-, 9-, 10-membered heterocyclyl; wherein the $C_2$-$C_6$ alkenyl, $C_2$-$C_6$ alkynyl, $C_3$-$C_{10}$ cycloalkyl, $C_3$-$C_8$ cycloalkenyl, aryl, 5-, 6-, 7-, 8-, 9-, and 10-membered heterocyclyl of $R_2$ are optionally substituted with one to five substituents independently chosen from $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, $C_4$-$C_8$ cycloalkenyl, halo, —OH, —$NH_2$, (A)(A')(A")(A''')aryl, (A)(A')(A")(A''')heterocyclyl, $NR_{14}R_{15}$, ($CH_2$)$_pNR_{14}R_{15}$, —CN, —$NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A") and (A''') are each an independently chosen from —H and $C_1$-$C_6$ alkyl and each heterocyclyl of (A)(A')(A")(A''') heterocyclyl is independently chosen from 5-, 6-, 7-, 8-, 9-, 10-membered heterocyclyl. In another embodiment Z is —($CH_2$)$_p$ or —CH=CH—.

In another embodiment of the compounds of formula I, Y is chosen from the following: —O—, —$OCR_gR_h$—, —$CR_gR_hO$—, —$CR_gR_h$—, and —($CR_gR_h$)$_2$—.

In a first embodiment of the compounds of formula I the radical X is —(CO)$R_1$, wherein $R_1$ is $NR_5CHR_{11}COR_{13}$. In a second embodiment X is —(CO)$R_1$ and $R_1$ is $NHCHR_{11}CONR_8R_9$. In a third embodiment X is —(CO)$R_1$ and $R_1$ is $NHCHR_{11}CONHCH_3$. In a fourth embodiment X is —(CO)$R_1$ and the radical $R_1$ is NHCH(tBu)CONHCH$_3$.

In another embodiment of the compounds of the present invention the radical $R_2$ is chosen from halo, $C_1$-$C_6$ alkyl, $C_2$-$C_6$ alkenyl, $C_3$-$C_7$ cyclo-alkyl, $C_3$-$C_7$ cycloalkenyl, aryl, 5- and 6-membered monocyclic heterocyclyl and 9- and 10-membered bicyclic heterocyclyl; wherein the $C_1$-$C_6$ alkyl, $C_2$-$C_6$ alkenyl, $C_3$-$C_7$ cyclo-alkyl, aryl, 5- and 6-membered monocyclic heterocyclyl and 9- and 10-membered bicyclic heterocyclyl of $R_2$ are optionally substituted with one to three substituents independently chosen from $C_1$-$C_4$ alkyl, $C_1$-$C_4$ alkoxy, $C_1$-$C_4$ haloalkoxy, $C_1$-$C_4$ haloalkyl, $C_3$-$C_6$ cycloalkyl, aryl, 5-, 6- and 7-membered heterocyclyl, halo, —OH, —$NH_2$, $NR_{14}R_{15}$, ($CH_2$)$_pNR_{14}R_{15}$, —CN, —$NO_2$, oxo, —$COOR_{14}$, —$SO_2R_{14}$, —$SO_2NR_{14}R_{15}$, —$NR_{15}SO_2R_{16}$, —$COR_{14}$, —$CONR_{14}R_{15}$ and —$NR_{15}COR_{16}$.

In another embodiment of the compounds of the present invention of formula I the radical $R_2$ is chosen from —H, halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$alkoxy, aryl, 5-, 6-, 7-, 8-, 9-, 10-membered heterocyclyl; wherein the $C_2$-$C_6$ alkenyl, $C_2$-$C_6$ alkynyl, $C_3$-$C_{10}$ cycloalkyl, $C_3$-$C_8$ cycloalkenyl, aryl, 5-, 6-, 7-, 8-, 9-, and 10-membered heterocyclyl of $R_2$ are optionally substituted with one to five substituents independently chosen from $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, $C_4$-$C_8$ cycloalkenyl, halo, —OH, —$NH_2$, (A)(A')(A")(A''')aryl, (A)(A')(A")(A''')heterocyclyl, $NR_{14}R_{15}$, ($CH_2$)$_pNR_{14}R_{15}$, —CN, —$NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A") and (A''') are each an independently chosen from —H and $C_1$-$C_6$ alkyl and each heterocyclyl of (A)(A')(A")(A''')heterocyclyl is independently chosen from 5-, 6-, 7-, 8-, 9- and 10-membered heterocyclyl.

In another embodiment the radical $R_2$ is chosen from $C_1$-$C_6$ alkyl, $C_3$-$C_6$ alkenyl, $C_3$-$C_7$ cycloalkyl, $C_3$-$C_7$ cycloalkenyl, phenyl, and 5- and 6-membered monocyclic heterocyclyl; wherein the $C_1$-$C_6$ alkyl, $C_3$-$C_6$ alkenyl, $C_3$-$C_7$ cycloalkyl, $C_3$-$C_7$ cycloalkenyl, phenyl, and 5- and 6-membered monocyclic heterocyclyl of $R_2$ are optionally substituted with one to two substituents independently chosen from $C_1$-$C_4$ alkyl, $C_1$-$C_4$ alkoxy, —$OCF_3$, —$CF_3$, $C_3$-$C_6$ cycloalkyl, -halo, —OH, and —CN; and the $C_3$-$C_7$ cycloalkyl, $C_3$-$C_7$ cycloalkenyl, phenyl, and 5- and 6-membered monocyclic heterocyclyl of $R_2$ are further optionally substituted with an additional halo substituent.

In another embodiment at least one of $R_a$, $R_b$, $R_c$, $R_d$, $R_e$, $R_f$, $R_g$ and $R_h$ is $C_1$-$C_8$ alkyl and $R_2$ is chosen from halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, 5-, 6-, 7-, 8-, 9-, 10-membered heterocyclyl; wherein the $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, aryl, 5-, 6-, 7-, 8-, 9-, and 10-membered heterocyclyl of $R_2$ are optionally substituted with one to five substituents independently chosen from $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, $C_4$-$C_8$ cycloalkenyl, halo, —OH, —$NH_2$, (A)(A')(A")(A''')aryl, (A)(A')(A")(A''')heterocyclyl, $NR_{14}R_{15}$, $(CH_2)_pNR_{14}R_{15}$, —CN, —$NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A") and (A''') are each an independently chosen from —H and $C_1$-$C_6$ alkyl and each heterocyclyl of (A)(A')(A")(A''')heterocyclyl is independently chosen from 5-, 6-, 7-, 8-, 9-, 10-membered heterocyclyl.

In another embodiment the linking group Z is a bond and the radical, $R_2$ is phenyl wherein the phenyl is optionally substituted with a substituent independently chosen from halo, —$CH_3$, —$OCH_3$, —$CF_3$ and —CN; and the phenyl is further optionally substituted with an additional one to two halo substituents.

In other embodiments of the compounds of formula I, $R_2$ is an aryl or substituted aryl chosen from: phenyl, 3-chloro-4-methylphenyl, 2-chloro-4-fluorophenyl, 2-fluoro-4-chlorophenyl, 2-fluoro-4-bromophenyl, 2-fluoro-5-chlorophenyl, 2,4-difluoro-phenyl, 2,5-difluorophenyl, 3,5-difluorophenyl, 3,4-difluorophenyl, 2-fluoro-4-methyl-phenyl, 2-fluoro-5-methylphenyl, 2-fluoro-3-methoxyphenyl, 2-fluoro-4-methoxyphenyl, 2-fluoro-4-trifluoromethylphenyl, 2-fluoro-5-trifluoromethylphenyl, 3-cyano-4-fluoro-phenyl, 2-fluoro-4-methyl-5-chlorophenyl, 2,4-difluoro-5-chlorophenyl, 2,4,5-trifluoro-phenyl, 3,4,5-tri-fluorophenyl, 2,5-difluoro-4-methoxyphenyl, 2-fluoro-phenyl, 4-fluoro-phenyl, 2-chlorophenyl, 3-chlorophenyl, 3-methyl-4-fluorophenyl, 2-fluoro-3-chloro-phenyl, 3-trifluoromethylphenyl, 3-methylphenyl, 3-fluoro-4-methyl-phenyl, 3-methyl-4-fluoro-phenyl, 3-chloro-4-fluorophenyl, and 3-fluoro-4-chlorophenyl.

In still other embodiments of the compounds of formula I, $R_2$ is a substituted or unsubstituted alkyl, cycloalkyl, spiroalkyl, alkenyl, cycloalkenyl or heterocyclyl chosen from the following: ethyl, n-propyl, isopropyl, 1,2-dimethylpropyl, isobutyl, 3,3-dimethylbutyl, n-pentyl, n-hexyl, 1-methyl-2,2,2-trifluoroethyl, cyclopropylethyl, ethenyl, propen-1-yl, propen-2-yl, 2-methylpropen-1-yl, 3,3-dimethylbut-2-en-2-yl, 2-methylpropen-1-yl, 1-penten-1-yl, 1-hexen-1-yl, 3-methoxypropyl, cyclopropyl, cyclopentyl, cyclopentenyl, cyclohexyl, 4-methylcyclohexyl, 4,4,-difluorocyclohexyl, 1,4-dioxaspiro[4.5]dec-7-en-7-yl, cyclohexen-1-yl, 4-methylcyclohexen-1-yl, 4-tert-butyl-cyclohexen-1-yl, cyclohep-tyl, cyclohepten-1-yl, thiophen-3-ylethyl and 2-(thiophen-3-yl)ethen-1-yl.

In further embodiments of the compounds of formula I, $R_2$ is a heterocyclyl chosen from the following: dihydropyran-2-yl, tetrahydropyran-2-yl, dihydropyran-4-yl, piperidin-4-yl, pyridin-2-yl, 3,4-dihydropiperidin-4-yl, pyridin-3-yl, pyridin-4-yl, 3-fluoro-pyridin-4-yl, pyrimidin-5-yl, 1-methylpyrazol-4-yl, 3,5-dimethylisoxazol-4-yl, thiophen-2-yl, thiophen-3-yl, 4-methylthiophen-3-yl, furan-2-yl, 5-methyl-furan-2-yl, furan-3-yl, thiazol 2 yl benzofuran-2-yl, benzothiophen-3-yl, benzo[d][1,3]dioxol-5-yl and 2,3-dihydrobenzo[b][1,4]dioxin-6-yl.

In another embodiment of the compounds according to the present invention, Y is chosen from —$NR_i$—, —$CR_gR_hNR_i$— and —$NR_iCR_gR_h$—; Z is chosen from a bond, —$(CH_2)_p$— and —CO—; and X is —$(CO)R_1$.

In still another embodiment of the compounds of the invention, Y is chosen from oxygen, —$OCR_gR_h$— and —$CR_gR_hO$—; Z is chosen from a bond, —$(CH_2)_p$— and —CO—; and X is —$(CO)R_1$.

In another embodiment of the compounds according to the present invention, Y is chosen from —$CR_gR_h$— and —$(CR_gR_h)_2$—; Z is chosen from a bond, —$(CH_2)_p$— and —CO—; and X is —$(CO)R_1$.

In still another embodiment of the compounds of the invention, Z chosen from a bond and —$(CH_2)_p$—; and $R_1$ is chosen from —$NR_5R_6$,

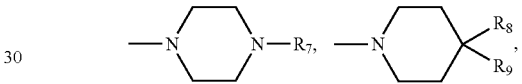

and a 7-, 8-, 9- or 10-membered heterocyclyl; wherein the 7-, 8-, 9- or 10-membered heterocyclyl of $R_1$ is optionally substituted with one to three substituents independently selected from the group consisting of $C_1$-$C_6$ alkyl, halo, —OH, —$NH_2$, —CN and —$NO_2$.

In a further embodiment of the compounds according to the present invention, Z is a bond and $R_1$ is —$NR_5R_6$; wherein $R_5$ is hydrogen; $R_6$ is chosen from —$CR_{10}R_nR_{12}$, and —$CR_{10}R_{11}COR_{13}$; $R_{10}$ is hydrogen; $R_{11}$ is chosen from hydrogen, $C_1$-$C_8$ alkyl l$C_3$-$C_{10}$ cycloalkyl, aryl, 5-, 6-, 7-, 8-, 9- and 10-membered heterocyclyl; wherein the alkyl, cycloalkyl, aryl and heterocyclyl of $R_{11}$ are optionally substituted with one to three substituents independently chosen from $C_1$-$C_4$ alkyl, $C_3$-$C_6$ cycloalkyl, aryl, 5-, 6-, 7-, 8-, 9- and 10-membered heterocyclyl, halo, —OH, $C_1$-$C_6$ alkoxy, —$NH_2$, —CN, —$NO_2$, oxo, —$COOR_{10}$, and —$CONR_8R_9$; $R_{12}$ is chosen from $C_1$-$C_6$ alkyl and $C_1$-$C_6$ hydroxyalkyl; and $R_{13}$ is —$NR_8R_9$.

The above-described compounds of formula I of the present invention can be formulated in pharmaceutically acceptable salts, acids salts, solvates (including hydrates) and stereoisomers of the compounds having the structure of formula I. Also provided by the present invention are mixtures of stereoisomers of the compounds having the structure of formula I wherein the mixture can include equal quantities of each stereoisomer, or the mixture can contain an excess of one stereoisomer over another.

In one embodiment of the invention, the compounds having the structure of formula I bind one or more cannabinoid receptors such as, without limitation the CB1 receptor or the CB2 receptor.

As used herein, a cannabinoid receptor-associated disease, condition or disorder is any disease, condition or disorder that is preventable or treatable by modulation of a cannabinoid receptor, such as and without limitation, CB2 or CB1. The modulation can be activation by an agonist, or inhibition by an inverse agonist. The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

The cannabinoid receptor-associated disease, condition or disorder can be any cannabinoid receptor-associated disease, condition or disorder, such as and without limitation: pain, inflammation, immunomodulation and pruritis; and can also include osteoclastogenesis. The cannabinoid receptor-associated disease, condition or disorder can also be obesity.

The cannabinoid receptor-associated pain can be neuropathic pain, somatic pain, visceral pain, cutaneous pain, ocular pain, otic pain, diabetic pain, pain associated with inflammatory bowel disease or irritable bowel syndrome, breakthrough cancer pain, metastatic cancer pain, virally-induced pain (such as AIDS-associated pain), or chemotherapy-induced pain.

The cannabinoid receptor-associated inflammation can be otic or ocular inflammation due to any of a variety of causes; inflammation due to rheumatoid arthritis, eczema, atopic dermatitis, inflammatory bowel disease, irritable bowel syndrome, kidney dialysis, insect bites or the inflammation can be inflammation caused by autoimmunity.

The cannabinoid receptor-associated pruritis can be opioid-induced pruritis, where in the pruritis is caused by use or abuse of an opioid, such as morphine.

The cannabinoid receptor can be any mammalian cannabinoid receptor, such as but not limited to, a human cannabinoid receptor or a rat cannabinoid receptor. In one aspect, the compounds of the invention having the structure of formula I are cannabinoid receptor agonists that activate a cannabinoid receptor.

In some embodiments, a particular dose and route of administration of the compound can be chosen by a clinician to completely prevent or cure the disease, condition or disorder. In other embodiments a particular dose and route of administration of the compound chosen by the clinician ameliorates or reduces one or more symptoms of the disease, condition or disorder.

As used herein, "effective amount" or "sufficient amount" of the synthetic peptide amide of the invention refers to an amount of the compound as described herein that may be therapeutically effective to inhibit, prevent, or treat a symptom of a particular disease, disorder, condition, or side effect.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

Pharmaceutically acceptable salts, pharmaceutically acceptable carriers used in parenteral preparations, suitable aqueous vehicles, buffers, suspending and dispersing agents and emulsifying agents useful in the preparation of pharmaceutically acceptable compositions that include the compounds of formula I of the present invention include those listed in U.S. Pat. No. 7,517,874.

The pharmaceutical compositions that include the compounds of formula I of the invention can be delivered or administered intravenously, transdermally, transmucosally, intranasally, subcutaneously, intramuscularly, orally or topically (such as for example to the eye). The compositions can be administered for prophylaxis or treatment of individuals suffering from, or at risk of a disease or a disorder. Prophylaxis is defined as a measure designed to preserve the health of an individual.

For therapeutic applications, a pharmaceutical composition is typically administered to a subject suffering from a disease, condition or disorder, in an amount sufficient to inhibit, prevent, or ameliorate the disease or disorder. An amount adequate to accomplish this is defined as an effective amount or a therapeutically effective dose.

The pharmaceutical compositions of the invention can be administered to a mammal for prophylactic or therapeutic purposes in any of the above-described formulations and delivery modes. The mammal can be any mammal, such as a domesticated or feral mammal, or even a wild mammal. The mammal can be any mammal, such as for instance a primate, ungulate, canine or feline. For instance, and without limitation, the mammal can be a pet or companion animal, such as a dog or a cat; a high-value mammal such as a thoroughbred or show animal; a farm animal, such as a cow, a goat, a sheep or pig; or a primate such as an ape or monkey. In one embodiment, the mammalian cannabinoid receptor is a human cannabinoid receptor, such as a human CB1 receptor (hCB1) or a human CB2 receptor (hCB2).

Without wishing to be bound by any particular theory, it is believed that due to their ability to bind and modulate the activity of the CB2 receptor, the compounds of the present invention are useful in the treatment of conditions or disorders that include, but are not limited to, inflammatory diseases such as rheumatoid arthritis, systemic lupus erythematosus, Crohn's disease, psoriasis, eczema, multiple sclerosis, diabetes and thyroiditis.

Certain compounds of the invention can also be used in the treatment of disorders that include, but are not limited to, pain (e.g. inflammatory pain, visceral pain, postoperative pain, cancer pain, neuropathic pain, musculoskeletal pain, dysmenorrhea, menstrual pain, migraine, headache); skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer, pancreatic cancer.

In addition, certain compounds of the invention can be used to modulate bone formation and/or resorption for treating conditions including, but not limited to, ankylosing spondylitis, gout, arthritis associated with gout, osteoarthritis and osteoporosis. Certain compounds of the invention can also be used for the treatment of neuropathic pain including but not limited to diabetic neuropathy, fibromyalgia, lower back pain, sciatica, pain from physical trauma, cancer, amputation, toxins or chronic inflammatory conditions. The compounds of the invention and their pharmaceutically acceptable salts can be administered in a standard manner, for example orally, parentarally, sublingually, dermally, transdermally, rectally, or via inhalation, or by buccal, nasal, ocular or otic administration.

General Methods

All reactions involving moisture sensitive compounds were carried out under an anhydrous nitrogen or argon atmosphere. All reagents were purchased from commercial sources and used without further purification. Unless otherwise noted, the starting materials used in the examples were obtained from readily available commercial sources or synthesized by standard methods known to those skilled in the art of organic synthesis. Reactions performed under microwave irradiation conditions were carried out in a Biotage Initiator® 60 microwave system (Charlottesville, Va.; model no. 10986-22V) with a 300 Watt magnetron. Normal phase chromatography and reverse phase chromatography was performed on an ISCO CombiFlash® Companion®, CombiFlash® Companion/TS® system (Teledyne Isco, Inc., Lincoln, Nebr.) or ISCO CombiFlash® Sq 16×. Reverse phase chromatography was also performed on a Waters Autopurification System with 3100 Mass Detector. The HPLC column was a Waters XBridge C18 5 μm OBD 19×150 mm; eluents were A: water with 0.1% formic acid and B: acetonitrile with 0.1% formic acid. Gradient elution was from 5% B-95% B. The total run time was 13 minutes. Mass spectra (MS) data were acquired on the Waters SQ Detector/3100 Mass detector using electrospray techniques or a Waters ZQ mass spectrometer with a Waters 600 HPLC pump and a 2487 UV detector and a 1525 u binary LC pump with integrated degasser.

Compounds were also characterized by their LCMS-Electrospray chemical ionization mass spectra (LC ESCI-MS) on one of the following systems:

(1) Waters HPLC-MS system (Waters Corp., Milford, Mass.) equipped with a 2767 Sample Manager, 2545 Binary Gradient Module, SFO System Fluidics Organizer, 2996 Photodiode Array Detector and 3100 Mass Detector. Data were collected across a range of wavelengths from 220-280 nm in positive ESCI mode. Spectra were scanned from 100-1400 atomic mass units (amu). The HPLC column was a Waters XBridge C18 3.5 μm 4.6×30 mm; eluents were A: water with 0.1% formic acid and B: acetonitrile with 0.1% formic acid. Gradient elution was from 5% B-95% B over 2.3 minutes with an initial hold of 0.2 minutes and a final hold at 95% B of 0.5 minutes. The total run time was four minutes.

(2) Waters (Waters Corporation, Milford, Mass.) UPLC-MS system equipped with an Acquity Sample Manager, Acquity Binary Solvent Manager, Acquity Photodiode Array Detector, Acquity Evaporative Light Scattering Detector and SQ Detector. Data were collected at 220 nm and 254 nm and in positive electrospray-chemical ionization mode. The UPLC column used was a Waters Acquity UPLC BEH C18 1.7 um 2.1×50 mm. Spectra were scanned from 100-1400 amu. The eluents were A: water with 0.1% formic acid and B: acetonitrile with 0.1% formic acid. Gradient elution from 5% B to 95% B over 0.8 minutes was used with a final hold at 95% B of 0.2 minutes at a flow rate of 0.8 milliliters per minute. Total run time was 1.5 minutes.

Nuclear magnetic resonance spectra were recorded using a Bruker Avance spectrometer (DPX400 Shielded), a Jeol ECX 400 MHz spectrometer or a Bruker Avance III (400 MHz shielded) spectrometer equipped with a Gradient Multinuclear Broadband Fluorine Observe (BBFO) probe. Spectra were acquired in the indicated solvent. Chemical shifts (δ) are given in ppm (parts per million upheld or downfield from TMS defined as 0 ppm). Coupling constants J are in hertz (Hz). Peak shapes in the NMR spectra are indicated by symbols 'q' (quartet), 't' (triplet), 'd' (doublet), 's' (singlet), 'br s' (broad singlet), 'br' (broad) 'm' (multiplet) and 'br d' (broad doublet).

Boc$_2$O: Di-tert-butyl dicarbonate; brine: Saturated sodium chloride; ° C.: degrees Celsius; CHCl$_3$: Chloroform; DBU: 1,8-Diazabicyclo[5,4,0]undec-7-ene; DCM: Dichloromethane; DMAP: 4-N,N-Dimethylaminopyridine; DMF: Dimethylformamide; DCE: Dichloroethane; DIEA: N,N-Diisopropylethylamine; DMS: Dimethylsulfate; DMSO: Dimethylsulfoxide; EtOH: Ethanol; EDCI: N-(3-dimethylaminopropyl)-N'-ethyl-carbodiimide; eq.: Equivalent; EtOAc: Ethyl acetate; HCl: Hydrochloric acid; HOAc: Acetic acid; HOBt: N-hydroxybenzotriazole; H$_3$PO$_4$: Phosphoric acid; iPrOH: Isopropanol; K$_2$CO$_3$: Potassium Carbonate; KH: Potassium hydride; LiOH: Lithium hydroxide; MeCN: Acetonitrile; MeOH: Methanol; MgSO$_4$: Magnesium sulfate; NaHCO$_3$: Sodium bicarbonate; NaOH: Sodium hydroxide; Na$_2$SO$_4$: Sodium sulphate; N$_2$: Nitrogen gas; PtO$_2$: Platinum (IV) oxide; psi: pounds per square inch; TBAF: tetra n-butylammonium fluoride; TBTU: O-(Benzo-triazol-1-yl)-N,N,N',N'-tetramethyluronium tetrafluoroborate; TEA: Triethylamine; TFA: Trifluoroacetic acid; THF: Tetrahydrofuran.

Synthetic Schemes:

Compounds of the present invention can be prepared according to the non-limiting synthetic schemes outlined in the general Schemes 1-10.

Products of the formula I where Y is —CR$_g$R$_h$NR$_i$— can be synthesized from intermediates of the type 1-4 (scheme 1).

Amino acids and amino esters 1-1 such as, for instance, glycine or alanine can be alkylated under basic conditions with substituted or unsubstituted acrylonitriles. The resulting amines can be reacted with the appropriate reagents to protect the amine, such as (Boc)$_2$O, to provide the intermediate 1-2. Reduction of the nitrile to the amine under reducing conditions, for instance PtO$_2$ and H$_2$, yields the intermediate 1-3. The amine 1-3 can then be cyclized under the appropriate conditions, such as EDCI/HOBt, to provide the intermediate 1-4.

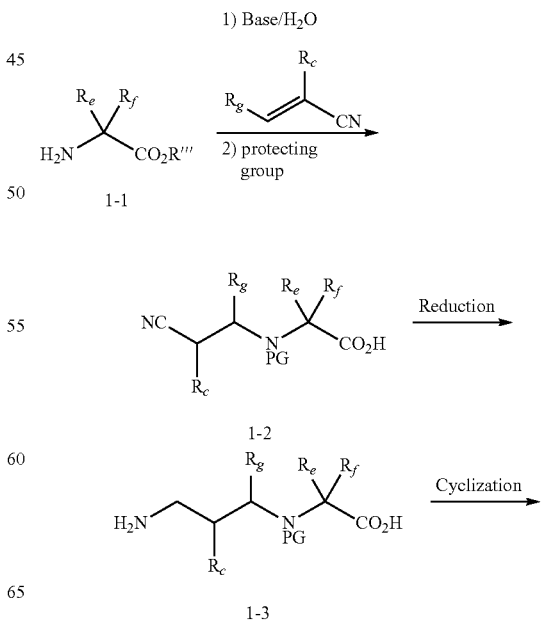

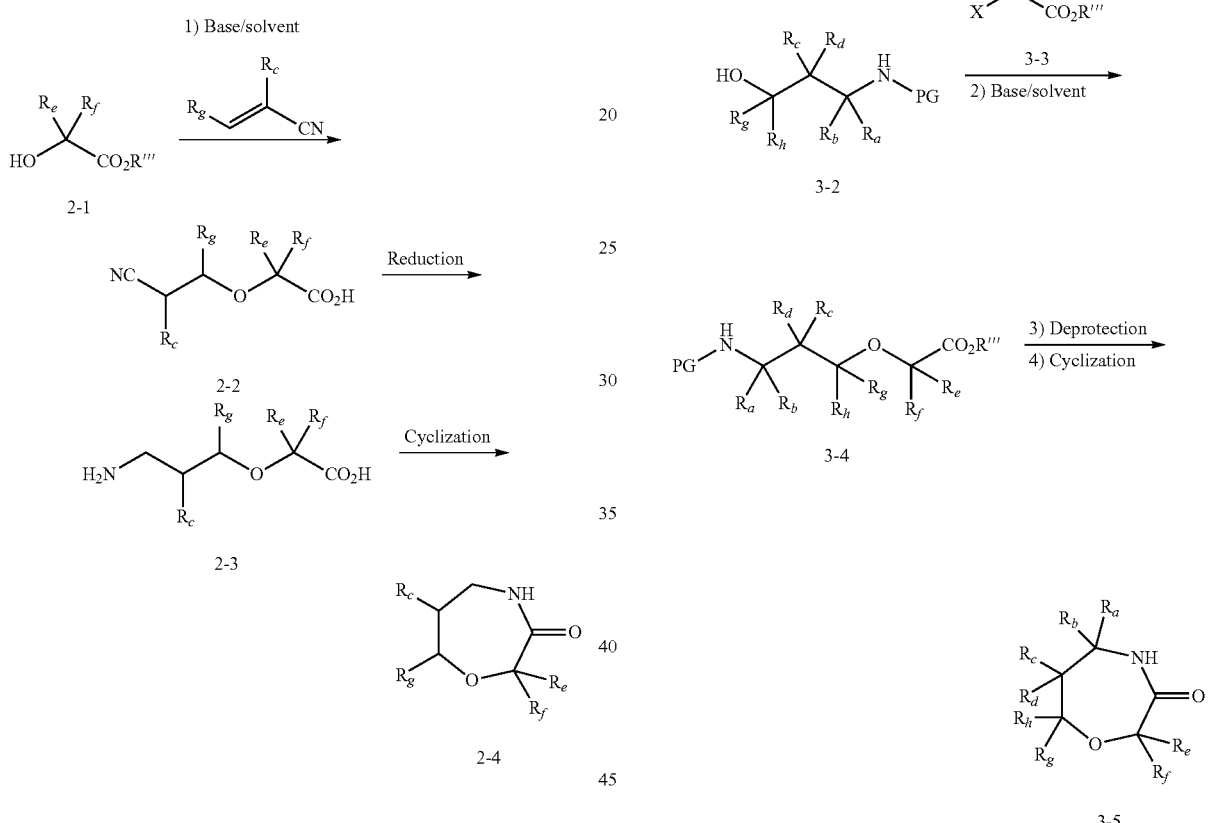

Products of the formula I where Y is —CR$_g$R$_h$O— can be synthesized from intermediates of the type 2-4 (scheme 2).

Alpha-hydroxy acids and esters 2-1 such as, for instance, glycolic or lactic can be alkylated under basic conditions with substituted or unsubstituted acrylonitriles to provide the ether intermediate 2-2. Reduction of the nitrile to the amine under reducing conditions, such as, for instance PtO$_2$ and H$_2$, yields the intermediate 2-3. The amine 2-3 can then be cyclized under the appropriate conditions, such as EDCI/HOBt, to provide the intermediate 2-4.

Intermediates of type 3-5, wherein Y is —CR$_g$R$_h$—, —(CR$_g$R$_h$)$_2$—, —O—, —OR$_g$R$_h$— can prepared according to scheme 3. Amino alcohols 3-1 can be selectively protecting using reagents such as di-tert-butyl dicarbonate to provide intermediate 3.2, This intermediate can be selectively alkylated on oxygen with intermediates such as 3-3 in the presence of a base such as sodium hydride in an aprotic solvent such as DMF or using aqueous sodium hydroxide under phase transfer conditions to provide intermediate 3-4. Deprotection of intermediate 3-4 followed by cyclization in the presence of a base such as potassium carbonate or sodium methoxide provides intermediate 3-5.

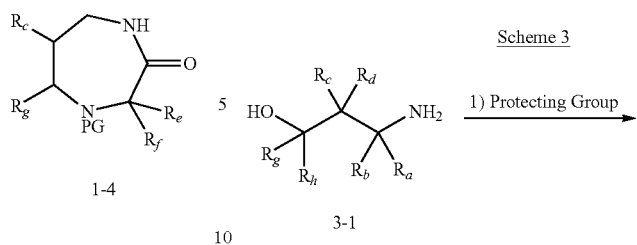

Intermediates of the type 4-2, wherein Y is —CR$_g$R$_h$—, —(CR$_g$R$_h$)$_2$—, —O—, —OR$_g$R$_h$—, are commercially available or can be prepared from an appropriate ketone via Beckmann rearrangement (shown in scheme 4).

Scheme 5A

1) Reductive Amination
2) protecting group

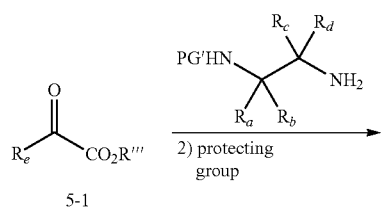

5-1

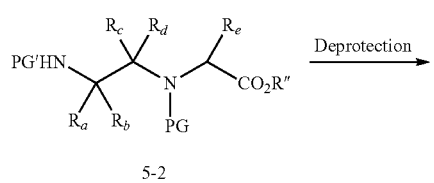

5-2

Deprotection

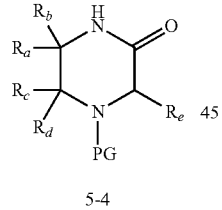

5-3

Cyclization

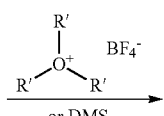

5-4

Intermediates of the type 5-4 and 5-8, wherein Y is —$NR_i$— can be prepared from appropriate suitably protected diamines and glyoxalic acid or pyruvic acid.

Alternatively, these intermediates can be prepared from alpha amino acids such as glycine or alanine and suitably protected alpha amino ketones or aldehydes (scheme 5A and 5B).

Scheme 5B

1) Reductive Amination
2) protecting group

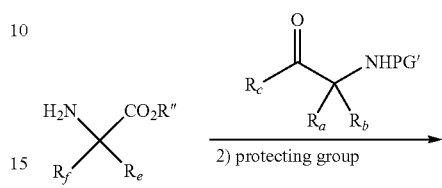

5-5

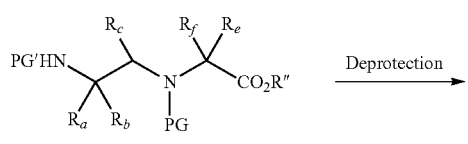

5-6

Deprotection

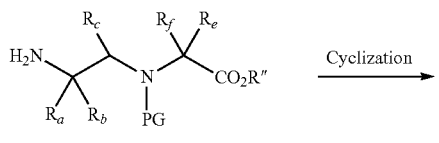

5-7

Cyclization

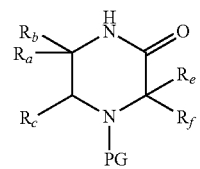

5-8

Scheme 6

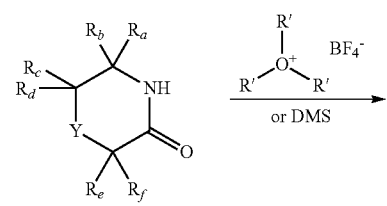

6-1

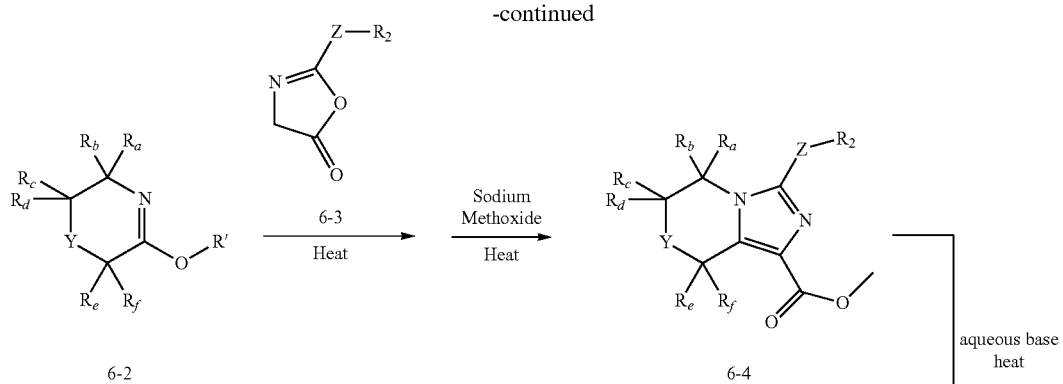

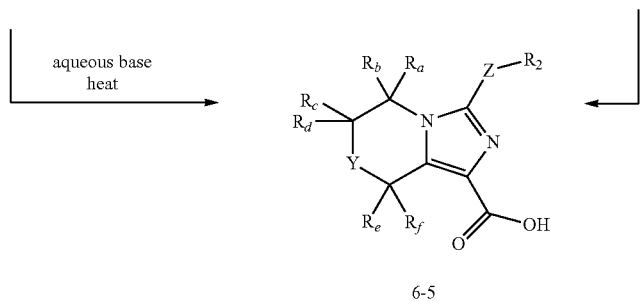

Intermediates of type 6-5 are prepared via scheme 6. The cyclic lactam 6-1, which is inclusive of intermediates 1-4, 2-4, 3-5, 4-2, 5-4 and 5-8, can be converted to the iminoether 6-2 using an alkylating agent such as a trialkyloxonium tetrafluoroborate or dimethylsulfate (DMS).

The intermediate 6-2 can then be transformed into the acid 6-5 by condensation of the imino ether with an oxalzolone (6-3) using heat followed by hydrolysis and cyclization by heating under basic conditions such as aqueous LiOH in methanol. Alternatively, the use of sodium methoxide in methanol in place of LiOH provides ester 6-4. Hydrolysis using LiOH provides acid 6-5.

Intermediate 6-5 can be converted (scheme 7) into products of the formula Ia by treatment with an appropriate amine in the presence of a coupling agents such as TBTU and a tertiary amine base, such as Hunig's base.

Scheme 7

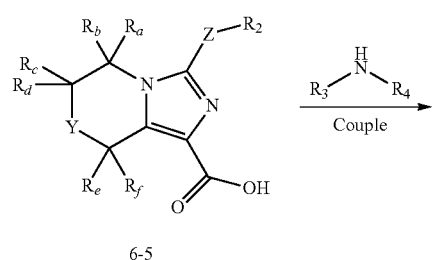

-continued

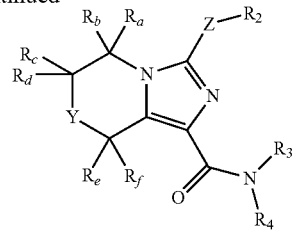

Ia

Intermediate 6-5 can also be used to complete the synthesis of the compounds of formulas Ib, Ic, Id and Ie as depicted in Scheme 8, below.

For example, intermediate 6-5 can be coupled with nucleophiles 8-1, 8-2, 8-3 and 8-4 in a single step by traditional peptide coupling conditions (e.g. TBTU; or EDCI, HOBt).

Cyclization of the coupled intermediates provides compounds of formulas Ib, Ic, Id and Ie. For example, cyclization of the amide generated in Method 1 with an ammonia source provides compounds of formula Ib.

Similarly cyclization of the amide generated in Method 2 under basic conditions in a polar aprotic solvent such as DMF provides the bicyclic oxazole compounds of formula Ic.

Alternatively, coupled intermediates generated in Method 3 may be cyclized by treatment with TBAF in an ethereal solvent such as THF providing substituted 1,2,4-oxadiazolyl compounds of formula Id.

Furthermore, coupled intermediates generated in Method 4 may be cyclized by treatment with Burgess Reagent in a polar aprotic solvent such as DMF at elevated temperatures, by, for instance, heating using microwave irradiation providing substituted 1,3,4-oxadiazolyl compounds of formula Ie.

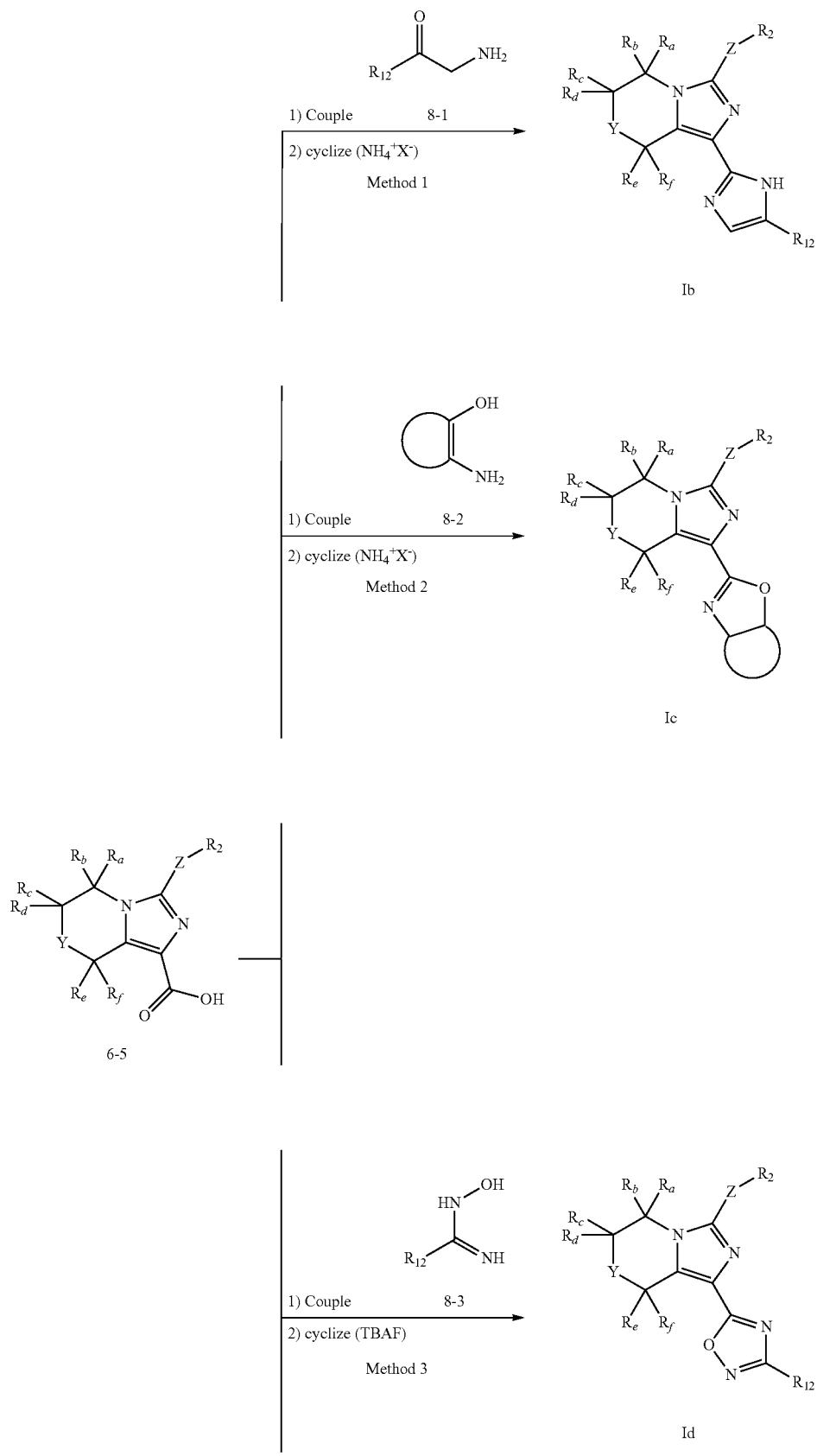

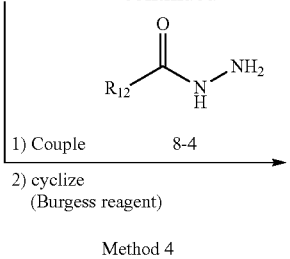

1) Couple    8-4
2) cyclize
   (Burgess reagent)

Method 4

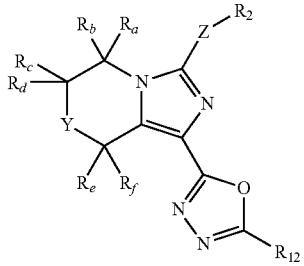

Ie

In instances where Y=—NR$_i$—, —NR$_i$CR$_g$R$_h$— or —CR$_g$R$_h$NR$_i$—, wherein R$_i$ is a protecting group for the nitrogen atom (PG), the protecting group of can be removed and the amine functionalized. The protecting group of the intermediate 9-1 is removed using conditions appropriate to the particular protecting group as is well known to those skilled in the art, to provide the compounds of formula If shown in scheme 9, below.

Scheme 9

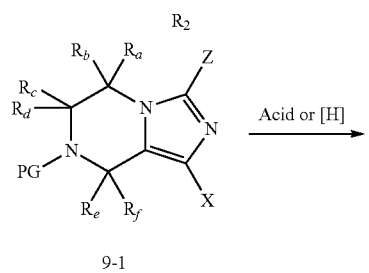

9-1

Acid or [H] →

-continued

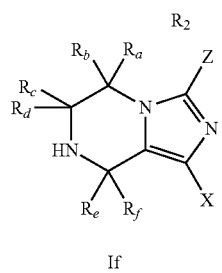

If

Treatment of a compound of formula If with an isothiocyanate or an isocyanate, for example, 2-fluorophenylisocyanate, or a carbamoyl- or thiocarbamoylchloride such as N,N-dimethylcarbamoylchloride provides compounds of formula Ig.

Scheme 10

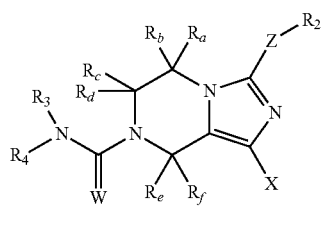

Ig

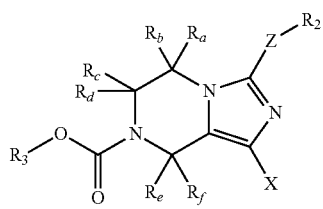

Ih

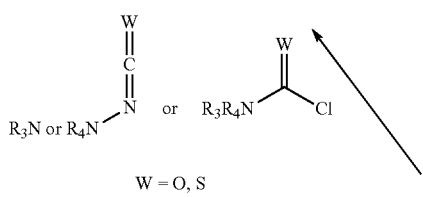

W = O, S

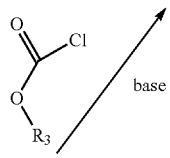

base

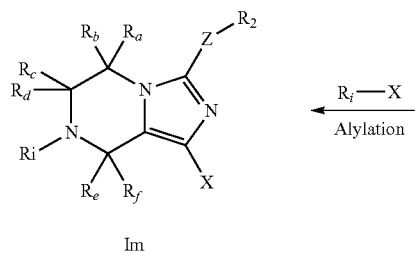 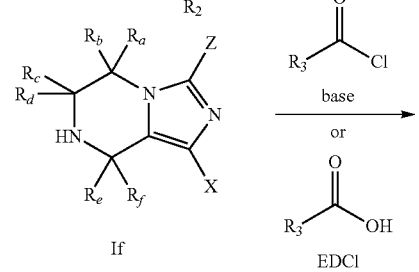 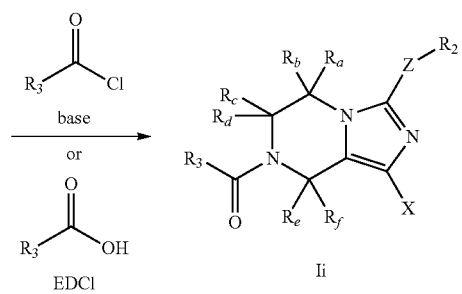

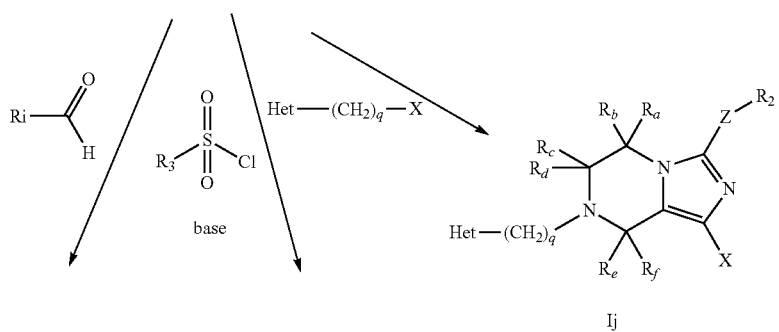

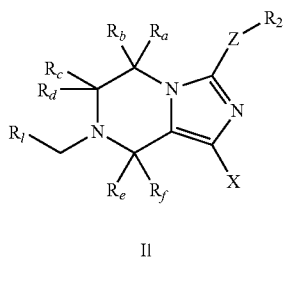 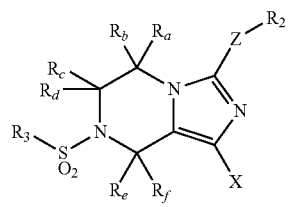

Alternatively, the amine If is acylated with a chloroformate derivative such as methyl chloroformate or an acid chloride, for example benzoyl chloride, or sulfonylated with a sulfonyl chloride such as methyl sulfonyl chloride using a base such as triethylamine to give compounds of formula Ih, Ii or Ik, respectively.

In a second alternative, amine If is treated with a carboxylic acid using a coupling reagent such as EDCI to provide compounds of formula Ii.

Reductive amination of If with an aldehyde, for example 4-(trifluoro-methoxy)-benzaldehyde, or ketone such as dihydro-2H-pyran-4(3H)-one in the presence of a hydride source, e.g. sodium triacetoxyborohydride gives compounds of formula Il.

Treatment of a compound If with an alkyl, alkenyl or alkynl halide such as methyl iodide, allyl bromide or benzyl bromide provides a compound of formula Im.

In still another alternative, compound If is treated with a halogenated heterocycle such as 2-chloropyrimidine to provide a compound of formula Ij.

Preparation of Intermediate A1:
2-(3,4-difluorophenyl)oxazol-5(4H)-one 198.2 [M+H]+. 1H-NMR (CDCl3) δ 7.85 (m, 1H), 7.78 (m, 1H), 7.30 (m, 1H), 4.45 (s, 2H).

Preparation of Intermediate A2:
2-(2,5-difluorophenyl)oxazol-5(4H)-one

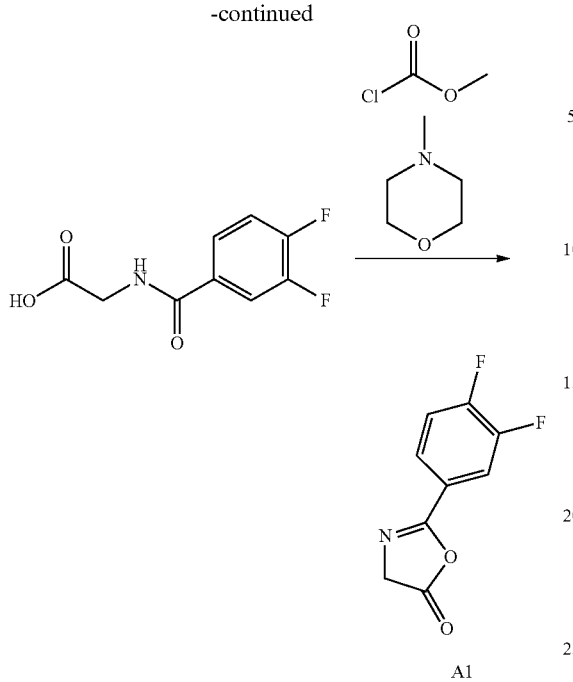

A1

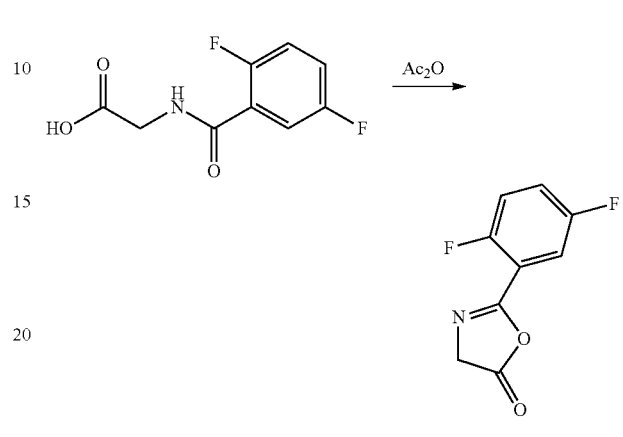

Step 1: Preparation of 2-(3,4-difluorobenzamido)acetic acid: Glycine (8.26 g, 110 mmol) was dissolved in 2M NaOH (125 ml, 250 mmol). The resulting colorless solution was cooled to 0° C. and 3,4-difluorobenzoyl chloride (12 mL, 95 mmol) in 60 mL of THF was added dropwise over 10 minutes. The reaction was stirred for 1 hour at 0° C. and allowed to warm to room temperature over 2 hours. The reaction was acidified to pH 1 with concentrated HCl while cooling in an ice bath. 100 mL of EtOAc was added and the mixture was poured into a separatory funnel and the layers separated. The aqueous layer was extracted with EtOAc (2×50 mL). The combined organic layers were washed with water and brine (50 mL each), dried with sodium sulfate, filtered and concentrated in vacuo to about 30 mL whereupon a solid began to crystallize. The mixture was allowed to stand overnight. The solid residue was concentrated on a rotary evaporator to remove the remaining EtOAc and then dried in a vacuum oven at 40° C. to provide the desired product, 2-(3,4-difluorobenzamido)acetic acid as an off-white solid (20.73 grams, 96%). LCMS (+ESI) m/z 216.2 [M+H]+. 1H-NMR (CDCl3) δ 12.70 (br s, 1H), 9.00 (t, 1H), 7.90 (m, 1H), 7.75 (m, 1H), 7.55 (m, 1H), 3.90 (s, 2H).

Step 2: Preparation of 2-(3,4-difluorophenyl)oxazol-5 (4H)-one: To a solution of 2-(3,4-difluorobenzamido)acetic acid (5.18 g, 24.1 mmol) in THF (25 mL) in a 100 mL round-bottomed flask was added 4-methylmorpholine (2.44 g, 24.1 mmol) to give a colorless solution. The solution was cooled to −10° C. and methyl chloroformate (2.28 g, 24.1 mmol) was added slowly over the course of thirty minutes while maintaining the solution at −10° C. A white precipitate started to form almost immediately and the solution became increasingly orange in color. Once the addition of chloroformate was complete the solution was stirred at −10° C. for 1 hour and warmed to room temperature over the course of an hour. The solution was filtered through a glass frit and the remaining solid was washed thoroughly with THF until colorless. The combined filtrate was evaporated under reduced pressure to provide 2-(3,4-difluoro-phenyl)oxazol-5(4H)-one as a light orange solid (4.5 g, 95%). LCMS (+ESI) m/z Step 1: 2-(2,5-difluorobenzamido)acetic acid was prepared in the same manner as 2-(3,4-difluorobenzamido)acetic acid described above, except that 2,5-difluorobenzoyl chloride was used in place of 3,4-difluorobenzoyl chloride. LCMS (+ESI) m/z 216.2 [M+H]+. 1H-NMR (dmso d6) δ 12.69 (br s, 1H), 8.66 (bdd, 1H), 7.55-7.30 (m, 3H), 7.75 (m, 1H), 3.93 (d, 2H).

Step 2: A 100 mL round-bottomed flask was charged with 2-(2,5-difluorobenzamido)acetic acid (1.7 g, 7.9 mmol) and acetic anhydride (7.46 mL, 79 mmol). The resulting suspension was heated to 100° C. for 20 minutes (during which time the solids had all dissolved) and cooled to room temperature. The mixture was concentrated in vacuo and azeotroped with toluene and dried under vacuum for a weekend. This yielded an orange-colored oil that was used without further purification. An analytical sample was obtained by trituration with tert-butyl methyl ether. 1H-NMR (CDCl3) δ 7.34 (m, 1H), 7.19-7.04 (m, 2H), 4.38 (d, 2H).

Preparation of Intermed. A3:
2-(2-fluoro-5-chlorophenyl)oxazol-5(4H)-one

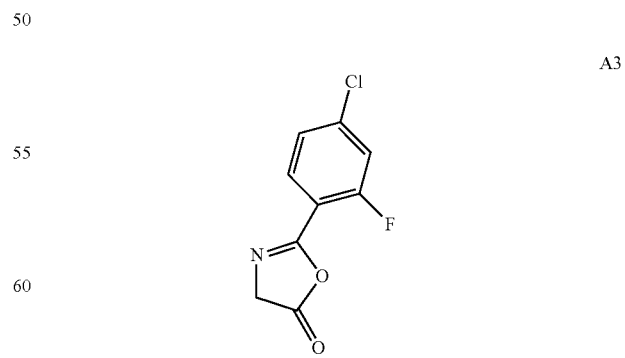

The title compound was prepared according to the procedure described for the preparation of Intermediate A1, using 2-(2-fluoro-5-chlorobenzamido)acetic acid in place of 2-(3, 4-difluoro-benzamido)acetic acid. $^1$H-NMR (CDCl$_3$) δ 7.32-7.26 (m, 2H), 7.24-7.18 (m, 1H) 4.47 (d, 2H).

Preparation of Intermediate B1: 3-phenyl-6,7,8,9-tetrahydro-5H-imidazo[1,5-a]azepine-1-carboxylic acid

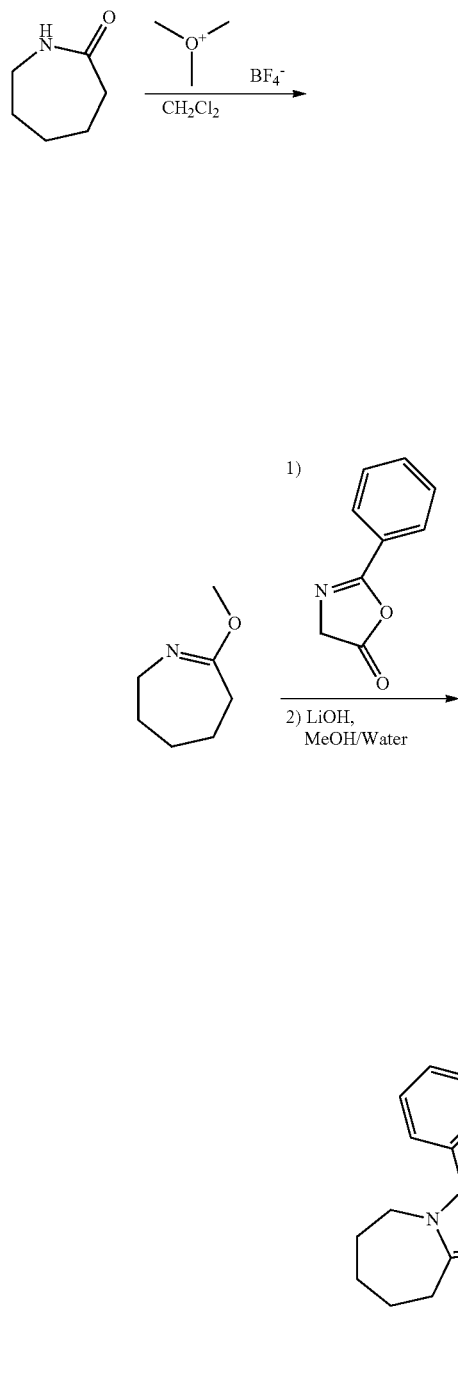

Preparation of trimethyloxonium tetrafluoroborate (adapted from T. J. Curphey, Org. Synth., Coll. Vol. 6, p. 1019 (1988) with slight modification as follows):

An oven-dried 500 mL 3-neck round-bottomed flask (marked with a line marked at about 190 mL), equipped with a N$_2$ inlet, 60 mL pressure-equalized dropping funnel, magnetic stirrer bar and rubber septum was placed under a blanket of dry nitrogen gas. DCM (80 mL) was added, followed by boron trifluoride diethyl etherate (33.3 mL, 270 mmol) and the mixture was cooled in a dry ice-acetone bath. Dimethyl ether was condensed into the DCM solution via a needle (through the rubber septum) that remained just below the surface until the total volume of the liquid reached the 190 mL mark. The mixture was stirred vigorously while epichlorohydrin (24.1 mL, 307 mmol) was added drop wise over approximately 15 minutes (the mixture became very thick and required occasion manual swirling to ensure good stirring). The bath was removed and the mixture was stirred vigorously overnight. The resulting solid was collected by filtration through an oven dried, medium frit glass Buchner funnel under a stream of N$_2$ and the flask and filter were rinsed with DCM (2×100 mL). The trimethyloxonium tetrafluoroborate product was isolated as a free-flowing white solid (29.4 g, 98%) after drying under nitrogen and was stored under nitrogen in an oven-dried glass bottle in a freezer.

Step 1: Preparation of (E)-7-methoxy-3,4,5,6-tetrahydro-2H-azepine: To a solution of azepan-2-one (1.13 g, 10.0 mmol) in DCM (10 mL) in a 40 mL screw cap vial was added freshly prepared trimethyloxonium tetrafluoroborate (1.57 g, 10.59 mmol). The resulting suspension was shaken overnight. The reaction was quenched by the addition of saturated aqueous NaHCO$_3$ (5 ml) (caution: vigorous CO$_2$ evolution). More aqueous sodium hydrogen carbonate was added until the aqueous layer reached pH 8. The organic layer was removed and the aqueous layer extracted with DCM (5 mL). Combined organic layers were dried over anhydrous sodium sulfate, filtered and evaporated under reduced pressure to yield (E)-7-methoxy-3,4,5,6-tetrahydro-2H-azepine (1.2 g, 95%) as a clear oil. LCMS (+ESI) m/z 128.2 [M+H]$^+$. $^1$H-NMR (CDCl$_3$) δ 3.60 (s, 3H), 3.45 (m, 2H), 2.40 (m, 2H), 1.80 (m, 2H), 1.60-1.50 (m, 4H).

Step 2: Preparation of 3-phenyl-6,7,8,9-tetrahydro-5H-imidazo[1,5-a]azepine-1-carboxylic acid: (E)-7-methoxy-3,4,5,6-tetrahydro-2H-azepine (0.395 g, 3.10 mmol) and 2-phenyloxazol-5(4H)-one (0.5 g, 3.10 mmol) were dissolved together in THF (2 mL) and DCE (2 mL) in a 5 mL microwave vial to give a orange solution. The vial was sealed and the solution was heated to 150° C. for 5 minutes. LCMS showed two peaks of the same mass (tautomers of the condensation product, R$_f$ 0.78 and 0.83 minutes, respectively). The reaction was concentrated and the residue diluted with MeOH (1 mL) and a solution of lithium hydroxide monohydrate (0.391 g, 9.31 mmol) in water (0.5 mL). The reaction was subjected to microwave irradiation and heated at 120° C. for 5 minutes. LCMS showed a single, new peak (R$_f$ 0.53 same molecular weight) corresponding to the desired product. The reaction was concentrated to remove MeOH and then diluted with water (1 mL). The solution was acidified to pH 2 with 5M HCl and extracted with of DCM (3×2 mL). The combined organic layers were filter, dried over anhydrous sodium sulfate and evaporated under reduced pressure to provide 3-phenyl-6,7,8,9-tetrahydro-5H-imidazo[1,5-a]azepine-1-carboxylic acid (421 mg, 59%) as a brown oil that was used without further purification. LCMS (+ESI) m/z 257.1 [M+H]$^+$.

The intermediates listed in Table 1 were prepared using the procedure described for the synthesis of Intermediate B1, starting from the listed oxazolone intermediates.

TABLE 1

| Intermediate | Structure | Chemical Name | m/z | Oxazolone |
|---|---|---|---|---|
| B2 | 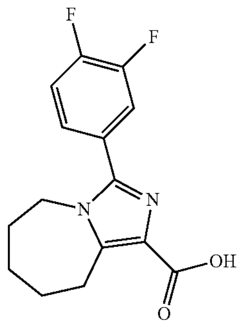 [SMILES: O=C(O)c1nc(-c2ccc(F)c(F)c2)n2c1CCCCC2] | 3-(3,4-difluorophenyl)-6,7,8,9-tetrahydro-5H-imidazo[1,5-a]azepine-1-carboxylic acid | 293.2 [M + H]⁺ | A1 |
| B3 | 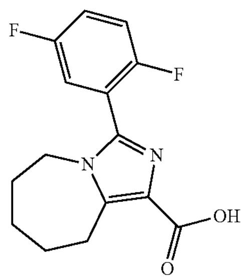 [SMILES: O=C(O)c1nc(-c2cc(F)ccc2F)n2c1CCCCC2] | 3-(2,5-difluorophenyl)-6,7,8,9-tetrahydro-5H-imidazo[1,5-a]azepine-1-carboxylic acid | 293.1 [M + H]⁺ | A2 |

Preparation of Intermediate C1: 3-(3,4-difluorophenyl)-5,6,7,8-tetrahydroimidazo[1,5-a]pyridine-1-carboxylic acid

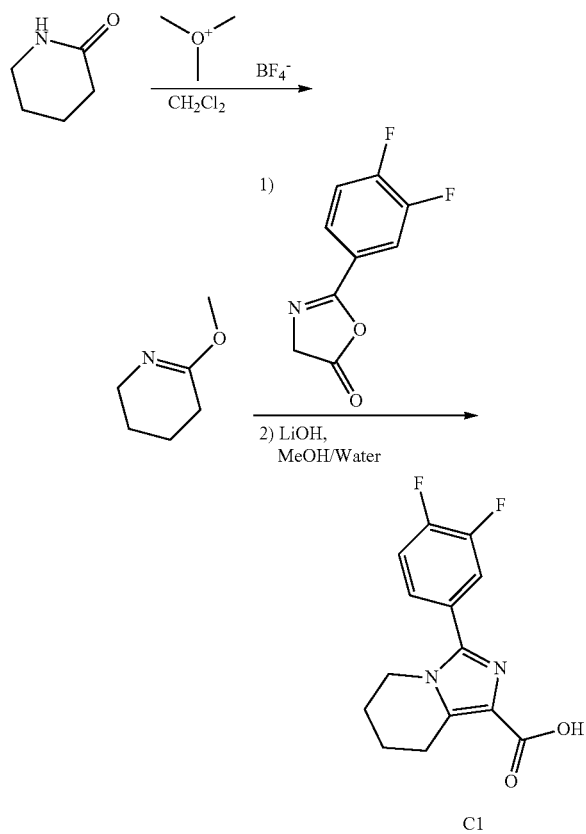

Step 1: Preparation of 6-methoxy-2,3,4,5-tetrahydropyridine

Piperidin-2-one (2.077 g, 20.95 mmol) was dissolved in DCM (10 mL) in a 40 mL screw-cap vial. Trimethyloxonium tetrafluoroborate (3.25 g, 22.00 mmol) was added resulting in a suspension. The vial was capped and shaken for 2 hours, after which time the solid had dissolved. Saturated aqueous potassium carbonate (10 mL) was added followed by water (100 mL) and organic layer was separated. The aqueous layer was further extracted with DCM (2×10 mL). The combined organic extracts were dried, filtered and evaporated under reduced pressure to provide the title compound (2.146 g, 90%) as a clear, light yellow oil. LCMS (+ESI) m/z: 114.2 [M+H]⁺.

Step 2: Preparation of 3-(3,4-difluorophenyl)-5,6,7,8-tetrahydroimidazo-[1,5-a]pyridine-1-carboxylic acid 6-methoxy-2,3,4,5-tetrahydropyridine (0.431 g, 3.80 mmol) was dissolved in THF (5 mL) in a 40 mL screw-cap vial and 2-(3,4-difluorophenyl)oxazol-5(4H)-one (0.75 g, 3.80 mmol) in THF (5 mL) was added, producing an orange solution. The vial was capped and heated to 90° C. for 3 hours. THF was removed under reduced pressure and the residue was dissolved in MeOH (10 ml) and lithium hydroxide monohydrate (0.479 g, 11.41 mmol) in water (1 mL) was added. The reaction was heated to 90° C. for 3 hours. MeOH was removed by evaporation under reduced pressure. The remaining aqueous solution was diluted with water (5 mL) and acidified to pH 2 with 5M HCl. The solution was extracted with EtOAc (3×5 mL). The combined organic extracts were dried over anhydrous sodium sulfate, filtered and evaporated to yield the desired product as a brown oil (742 mg, 71%) that was used without further purification. LCMS (+ESI) m/z: 279.3 [M+H]⁺.

Preparation of Intermediate D1: 3-phenyl-5,6,8,9-tetrahydroimidazo-[1,5-d][1,4]oxazepine-1-carboxylic acid

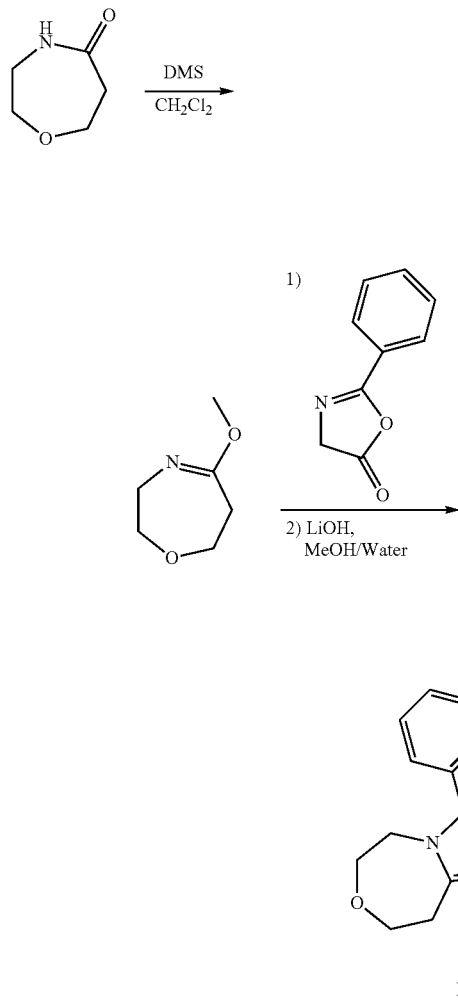

D1

Step 1: Preparation of (E)-5-methoxy-2,3,6,7-tetrahydro-1,4-oxazepine

To a solution of 1,4-oxazepan-5-one (0.091 g, 0.793 mmol) in DCM (2 mL) in a screw-cap vial was added dimethyl sulfate (0.1 g, 0.793 mmol) to give a colorless solution. The reaction was heated to 150° C. for 5 minutes. Potassium carbonate (200 mg) was added and the vial was capped and shaken. The reaction was filtered through a glass frit and solvent was removed under reduced pressure to give a clear oil (100 mg) that was used without further purification. LCMS (+ESI) m/z: 130.2 [M+H]$^+$.

Step 2: Preparation of 3-phenyl-5,6,8,9-tetrahydroimidazo[1,5-d][1,4]-oxazepine-1-carboxylic acid: (E)-5-methoxy-2,3,6,7-tetrahydro-1,4-oxazepine (50 mg, 0.387 mmol) was dissolved in THF (1 mL) in a screw-cap vial and 2-phenyloxazol-5(4H)-one (62.4 mg, 0.387 mmol) was added to give a orange solution. The reaction was heated to 150° C. for 5 minutes. LCMS shows two peaks of the corresponding product mass (tautomers of the condensation), $R_t$ 0.73 and 0.78 minutes. The reaction was concentrated under reduced pressure and the residue was dissolved in 1 mL MeOH and treated with lithium hydroxide monohydrate (81 mg, 1.936 mmol) and water (200 μL). The reaction was heated at 120° C. for 5 minutes using microwave irradiation to provide a new desired product (same MW as intermediate) with $R_t$=0.50 minutes. The reaction was concentrated to remove MeOH and then diluted with water (1 mL). The solution was acidified to pH2 with 5N HCl. The solution was extracted with DCM (3×2 mL). The combined organic extracts were dried and evaporated to provide the title compound as a brown oil (23 mg). Additional material was recovered by concentrating the aqueous layer and repeated extraction with DCM. The combined material (45 mg, 45%) was used without further purification. LCMS (+ESI) m/z: 130.2 [M+H]$^+$

Preparation of Intermediate D2: 3-(3,4-difluorophenyl)-5,6,8,9-tetrahydroimidazo[1,5-d][1,4]oxazepine-1-carboxylic acid

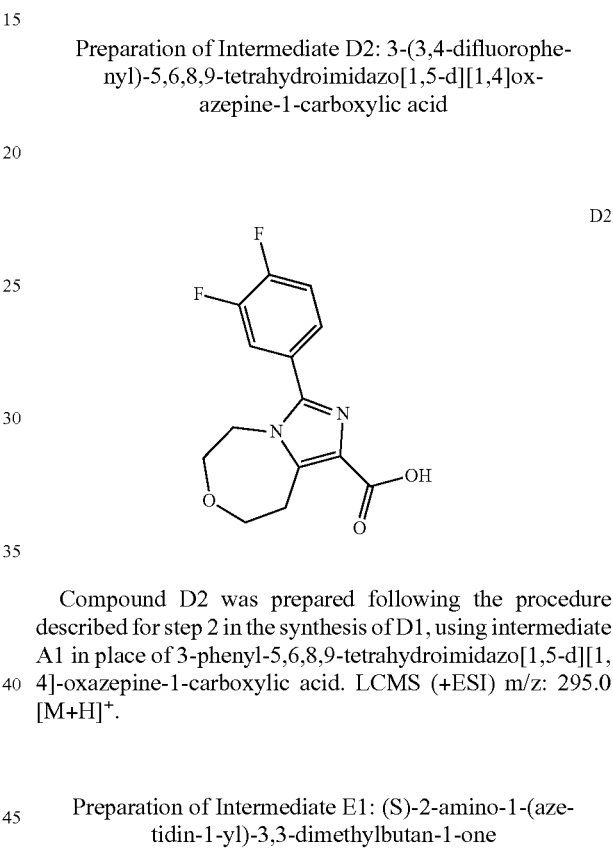

D2

Compound D2 was prepared following the procedure described for step 2 in the synthesis of D1, using intermediate A1 in place of 3-phenyl-5,6,8,9-tetrahydroimidazo[1,5-d][1,4]-oxazepine-1-carboxylic acid. LCMS (+ESI) m/z: 295.0 [M+H]$^+$.

Preparation of Intermediate E1: (S)-2-amino-1-(azetidin-1-yl)-3,3-dimethylbutan-1-one

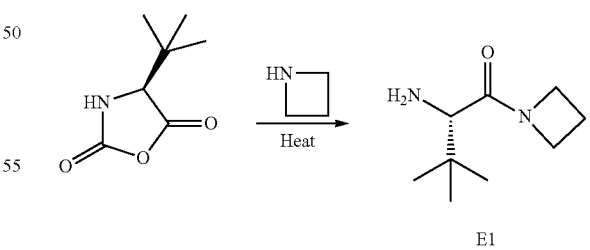

E1

(S)-4-tert-butyloxazolidine-2,5-dione (1.59 g, 10.12 mmol) and azetidine hydrochloride (0.946 g, 10.12 mmol) were combined in ethanol (5 mL) in a 2 mL microwave vial. The vial was capped and subjected to microwave irradiation at 150° C. for 10 min. The reaction was concentrated under reduced pressure and azeotroped with twice with toluene (5 mL) to provide the desired (S)-2-amino-1-(azetidin-1-yl)-3, 3-dimethylbutan-1-one as a brown oil (1.7 g, 99%) that was used without further purification. LCMS (+ESI) m/z: 171.1 [M+H]+.

Preparation of Intermediate F1: 3-(3,4-Difluorophenyl)-5,6,7,9-tetrahydroimidazo[5,1-c][1,4]-oxazepine-1-carboxylate

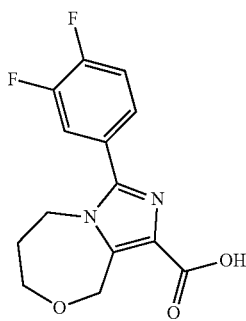

F1

Step 1: Preparation of 3-N-Boc-aminopropan-1-ol: To a stirred solution of 3-amino-1-propanol (19.75 g, 263 mmol) in 100 mL of water was added a solution of di-tert-butyl dicarbonate (54.6 g, 250 mmol) in 100 mL of THF dropwise over about 1 hour and the mixture stirred overnight. The solution was evaporated to a volume of about 100 mL and diluted with 100 mL of DCM. The layers were separated and the aqueous layer was extracted with 2×100 mL of DCM. The combined DCM extracts were washed with 100 mL each water and brine, dried over MgSO$_4$, filtered and concentrated in vacuo to yield an oil. The oil was further dried in a vacuum oven at 40° C. for 4 hours to provide 41.46 g (94%) of the title compound as a clear, colorless oil. $^1$H-NMR (CDCl$_3$) δ 4.79 (bs, 1H), 3.67 (t, 2H), 3.29 (t, 2H), 2.96 (bs, 1H) 1.67 (pentet, 2H), 1.45 (s, 9H).

Step 2: Preparation of 2-(3-N-Boc-amino-1-propoxy)acetic acid: The product from Step 1 above (14.95 g, 85 mmol), toluene (125 mL), tertabutylammonium bromide (1.38 g, 4.3 mmol) and 50% aqueous NaOH (45 mL, 853 mmol) were added to a 500 mL 3-N round-bottom flask fitted with a mechanical stirrer, a pressure-equalized dropping funnel and thermometer. Stirring was initiated and the mixture was cooled in an ice bath to <10° C. To the stirred solution was added a solution of tert-butyl bromoacetate (13.9 mL, 18.3 mmol) in 25 mL of toluene such that the internal temperature remained below 10° C. The mixture was stirred for 2 hours at this temperature and then ice bath was removed and the mixture stirred overnight. The layers were separated and the aqueous layer was extracted with 25 mL toluene. The aqueous phase was cooled with stirring in an ice bath and the pH of the solution was adjusted to 3 by the careful dropwise addition of concentrated aqueous HCl. Ethyl acetate (100 mL) was added and the layers were separated. The pH of the aqueous layer was readjusted to 3 by the addition of 1N aqueous HCl and the mixture was extracted with 100 mL EtOAc. This process was repeated and the combined organics were washed with 100 mL brine, dried over MgSO$_4$, filtered and concentrated in vacuo. The residue was dried in a vacuum oven at 40° C. overnight. The 2-(3-N-Boc-amino-1-propoxy)acetic acid (14.12 g, 71%) was obtained as a clear, thick oil. LCMS (+ESI) m/z: 179.1 [M+H-56]+ $^1$H-NMR (CD$_3$OD) δ 4.92 (bs, 2H), 3.57 (t, 2H), 3.16 (t, 2H), 1.75 (pentet, 2H), 1.44 (s, 9H).

Step 3: Preparation of Methyl 2-(3-amino-1-propoxy)acetate hydrochloride: The product from step 2 above (14.10 g, 60.4 mmol) was dissolved in 75 mL MeOH and cooled in an ice bath. Thionyl chloride (11.0 mL, 151 mmol) was added dropwise and the solution was stirred overnight during which time the ice bath melted. The reaction mixture was concentrated in vacuo to give 11.1 g of a thick oil that was used without further purification. $^1$H-NMR (DMSO d6) δ 8.08 (bs, 3H), 4.11 (s, 2H), 3.65 (s, 3H), 3.53 (t, 2H), 2.83 (m, 2H), 1.87-1.77 (m, 2H).

Step 4: Preparation of 1,4-Oxazepine-3-one: The crude product from step 3 (11.1 g, 60.4 mmol) above was dissolved in 200 mL of MeOH and carefully treated with K$_2$CO$_3$. The resulting suspension was heated to reflux for 90 minutes and then cooled to room temperature. Celite was added and the mixture was vacuum filtered. The filtrate was concentrated in vacuo to a volume of approximately 30 mL and 50 mL of water and 250 mL DCM were added. The layers were separated and the DCM layer was dried over MgSO$_4$, filtered and concentrated in vacuo to give the title compound as a light yellow oil that solidified on standing. $^1$H-NMR (CDCl$_3$) δ 6.15 (bs, 1H), 4.13 (s, 2H), 3.82 (t, 2H), 3.34-3.27 (m, 2H), 1.96-1.88 (m, 2H).

Step 5: Preparation of 3-Methoxy-2,5,6,7-tetrahydro-1,4-oxazepine: The product from step 4 (1.06 g, 9.2 mmol) was dissolved in 11 mL of DCM and the stirred solution was treated with trimethyloxonium tetrafluoroborate (1.70 g, 11.5 mmol) and the mixture was stirred for 4 hours. The reaction was quenched by addition of 1.70 mL saturated aqueous K$_2$CO$_3$ and the mixture was vigorously stirred for 15 minutes. The precipitate was removed by filtration and the filtrate concentrated in vacuo to provide 3-methoxy-2,5,6,7-tetrahydro-1,4-oxazepine (0.94 g, 80%) as a clear oil that was used without further purification.

Step 6: Preparation of Methyl 3-(3,4-Difluorophenyl)-5,6,7,9-tetrahydroimidazo[5,1-c][1,4]-oxazepine-1-carboxylate: The product from step 5 above (123 mg, 0.95 mmol) was suspended in 4 mL of toluene and the mixture heated to 90° C. The reaction mixture was treated with intermediate A1 (188 mg, 0.95 mmol) in four equal portions over the course of 30 minutes. The mixture was stirred at 90° C. for an additional 30 minutes and then mixture was cooled to room temperature and concentrated in vacuo. The residue was dissolved in 20 mL MeOH and sodium methoxide (77 mg, 1.43 mmol) was added. The mixture was heated to reflux for 45 minutes and then cooled to room temperature and 0.100 mL concentrated aqueous HCl and 2 mL toluene were added. The mixture was then concentrated in vacuo and the residue purified by normal phase column chromatography (ISCO RediSep 12, gradient elution, 40% to 100% EtOAc-hexanes) to give 163 mg (56%) of the title compound as a yellow solid. LCMS (+ESI) m/z: 309.1 [M+H]+ $^1$H-NMR (CDCl$_3$) δ 7.46-7.38 (m, 1H), 7.33-7.25 (m, 2H), 5.16 (s, 2H), 4.30-4.22 (m, 2H), 4.07 (dd, 2H), 3.92 (s, 3H), 2.03-1.96 (m, 2H).

Step 7: Preparation of intermediate F1: 3-(3,4-Difluorophenyl)-5,6,7,9-tetrahydroimidazo[5,1-c][1,4]-oxazepine-1-carboxylate: The product from step 6 above (155 mg, 0.50 mmol) was suspended in 4 mL of 25% aqueous methanol and treated with lithium hydroxide monohydrate (63 mg, 1.50 mmol) and the mixture was heated to reflux for 30 minutes. After cooling to room temperature, the mixture was concentrated in vacuo. The residue was dissolved in 2 mL of water and cooled in an ice bath. 1M aqueous H$_3$PO$_4$ was added until a pH of 1 was reached and the mixture extracted with 3×10 mL of 3:1 CHCl$_3$:iPrOH. The combined organics were dried over MgSO$_4$, filtered and concentrated in vacuo. The residue was dried in a vacuum oven overnight to provide 136 mg (92%) of the title compound as a light yellow solid. LCMS (+ESI) m/z: 295.1 [M+H]$^{+1}$ $^1$H-NMR (DMSO d6) δ 12.42 (bs, 1H) 7.72-7.55 (m, 2H), 7.47-7.38 (m, 1H), 5.03 (s, 2H), 4.30-4.20 (m, 2H), 3.94 (dd, 2H), 1.93-1.82 (m, 2H).

Intermediates listed in Table 2 were prepared using the procedure described for the synthesis of Intermediate F2, starting from the listed oxazolone intermediates described above.

TABLE 2

| Intermediate | Structure | Chemical Name | m/z | Oxazolone |
|---|---|---|---|---|
| F2 | 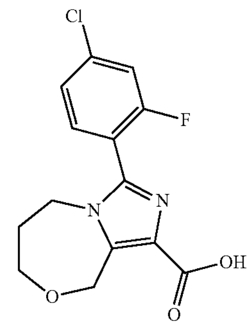 [SMILES: O=C(O)c1nc(-c2ccc(Cl)cc2F)n2c1COCCC2] | 3-(2-Fluoro-4-chlorophenyl)-5,6,7,9-tetrahydroimidazo[5,1-c][1,4]-oxazepine-1-carboxylate | 311.2 [M + H]$^+$ | A3 |
| F3 | 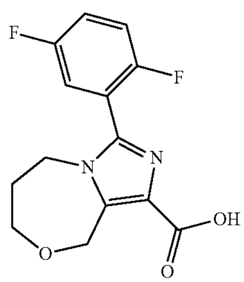 [SMILES: O=C(O)c1nc(-c2cc(F)ccc2F)n2c1COCCC2] | 3-(2,5-Difluorophenyl)-5,6,7,9-tetrahydroimidazo[5,1-c][1,4]-oxazepine-1-carboxylate | 295.1 [M + H]$^+$ | A2 |

Preparation of Intermediate G1: (R,S)-8-(tert-Butoxycarbonyl)-3-(3,4-difluorophenyl)-7-methyl-6,7,8,9-tetrahydro-5H-imidazo[1,5-a][1,4]diazepine-1-carboxylic acid

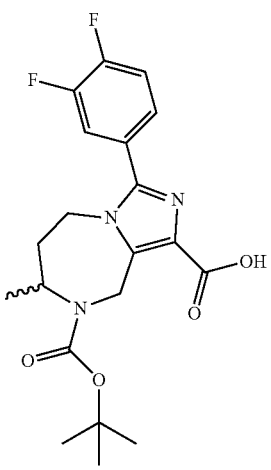

G1

Step 1: Preparation of (R,S)-2-(tert-Butoxycarbonyl(1-cyanopropan-2-yl)amino)acetic acid: Glycine (1.88 g, 25.0 mmol) was dissolved in 25 mL of water and treated in portions with K$_2$CO$_3$ (6.88 g, 27.5 mmol). After the cessation of bubbling, 2-butenenitrile (2.04 mL, 25.0 mmol) was added and the mixture was stirred for 20 minutes and then heated in an oil bath to 70° C. for 3 hours. The reaction mixture was cooled to room temperature and a solution of di-tert-butyl dicarbonate (5.46 g, 25.0 mmol) in 25 mL of THF was added and the mixture was stirred for 48 hours. The mixture was concentrated in vacuo to remove the THF and the remaining aqueous layer was cooled in an ice bath and the pH was adjusted to 2 by the addition of 5M aqueous HCL. 50 mL of EtOAc was added and the layers were separated. The pH of the aqueous phase was readjusted to 2 by the addition of 1M aqueous phosphoric acid and then extracted with 25 mL of EtOAc. The combined organic phases were washed with brine, dried over Na$_2$SO$_4$, filtered and concentrated in vacuo. The residue was placed in a vacuum oven at 40 C overnight. The title compound (5.24 g, 87%) was obtained as a thick oil. LCMS (+ESI) m/z: 243.1 [M+H]$^{+1}$ $^1$H-NMR (DMSO d6) δ 12.51 (bs, 1H) 4.45 (m, 1H), 3.87 (d, 2H), 3.63 (d, 2H), 1.44 (s, 4.5H), 1.41 (s, 4.5H), 1.22 (d, 3H).

Step 2: Preparation of (R,S)-2-((4-amino-butan-2-yl)(tert-butoxycarbonyl)amino)acetic acid: A Parr vessel was charged with a solution of the product of step 1 (5.10 g, 21.0 mmol) in 60 mL MeOH. The solution was purged with N$_2$ and PtO$_2$ (0.48 g, 2.1 mmol) was added. The mixture was hydrogenated (20-60 psi) overnight. The mixture was then filtered through a plug of Celite and the Celite pad was washed well with MeOH. The filtrate was concentrated in vacuo to a foam which was dried in a vacuum oven at 40° C. for 2 days. (R,S)-2-((4-amino-butan-2-yl)(tert-butoxy-carbonyl)amino) acetic acid (5.05 g, 97%) was obtained as a crusty solid. LCMS (+ESI) m/z: 247.0 [M+H]$^{+1}$ $^1$H-NMR (CD$_3$OD) δ 4.03 (m, 1H), 3.59 (d, 2H), 3.00 (m, 2H), 1.90-1.76 (m, 1H), 1.71-1.58 (m, 1H), 1.34 (s, 9H), 1.09 (d, 3H).

Step 3: Preparation of (R,S)-1-N-tert-Butoxycarbonyl-7-methyl-1,4-diazepin-3-one: The product from step 2 (5.04 g, 20.5 mmol) was suspended in 150 mL of DCM. The stirred suspension was treated with HOBt (0.78 g, 5.1 mmol) and then ethyl-dimethylaminopropylcarbodiimide hydrochloride (4.71 g, 24.6 mmol) was added in 4 equal portions over 1 hour and the mixture was stirred overnight. The mixture was concentrated in vacuo to remove the DCM and the residue was partitioned between saturated aqueous NaHCO$_3$ (50 mL) and 3×50 mL of EtOAc. The combined organic phases were washed with 25 mL each 1M HCl, saturated aqueous NaHCO$_3$, brine, dried over Na$_2$SO$_4$, filtered and concentrated in vacuo. The residue was purified by column chromatography (ISCO RediSep-40, gradient elution 0%-100% acetonitrile:EtOAc) to give 1.03 g (22%) of the title compound as a white solid. LCMS (+ESI) m/z: 230.1 [M+H]$^{+1}$ $^1$H-NMR (CD$_3$OD) δ 3.82 (d, 1H), 3.21 (dd, 1H), 3.09 (dd, 1H), 2.14 (dt, 1H), 1.82 (dt, 1H), 1.47 (s, 9H), 1.18 (d, 3H).

Step 4: Preparation of (R,S)-1-N-tert-Butoxycarbonyl-3-methoxy-7-methyl-1,4-diazepine: The product of step 3 (457 mg, 2.0 mmol) was dissolved in 4 mL of DCM and treated with trimethyloxonium tetratfluoroborate (311 mg, 2.1 mmol) and the mixture was stirred at room temperature overnight. The reaction was quenched by the addition of 3 mL of saturated aqueous NaHCO$_3$, and poured into 5 mL of DCM and 10 mL of saturated aqueous NaHCO$_3$. The layers were separated and the aqueous phase was extracted with 10 mL of DCM. The combined organic fractions were dried over Na$_2$SO$_4$, filtered and concentrated in vacuo to give 394 mg (81%) of the title compound as a yellow-orange oil that was used directly without further purification.

Step 5: Preparation of Intermediate G1: The product from step 4 (197 mg, 0.81 mmol) and intermediate A1 (160 mg, 0.81 mmol) were dissolved in 2 mL of acetonitrile and heated in a microwave to 140° C. for 10 minutes and at 150° C. for 5 minutes. After cooling to room temperature, the mixture was concentrated in vacuo. The residue was treated with 5 mL MeOH and concentrated in vacuo. The residue was dissolved in 6 mL MeOH (precipitate formed) and a solution of LiOH (102 mg, 2.44 mmol) in 2 mL water was added and the mixture was heated to 75° C. overnight. After cooling to room temperature, the mixture was concentrated in vacuo and the residue diluted with 10 mL water. The pH of the aqueous solution was carefully adjusted to 2 by the addition of 1 M aqueous phosphoric acid. The mixture was stirred for 10 minutes and the precipitate was collected by filtration and dried in a vacuum oven to provide the title compound (54 mg, 16%) as a white solid. LCMS (+ESI) m/z: 352.2 [M+H-56]$^{+1}$.

Preparation of Intermediate G2: (R,S)-8-(tert-Butoxycarbonyl)-3-(3,4-difluorophenyl)-6-methyl-6,7,8,9-tetrahydro-5H-imidazo[1,5-a][1,4]diazepine-1-carboxylic acid

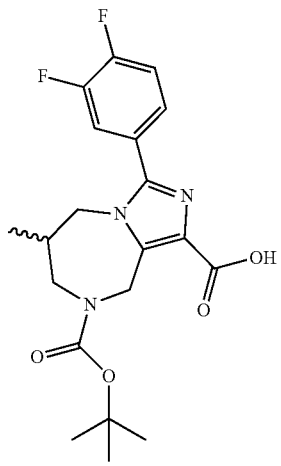

G2

The procedure described for the preparation of intermediate G1 was used, substituting methacrylonitrile for 2-butenenitrile in Step 1, to provide the title compound (98 mg, 17% overall yield). LCMS (+ESI) m/z: 408.2 [M+H]$^{+1}$ $_1$H-NMR (CD$_3$OD) δ 7.56-7.49 (m, 1H), 7.49-7.41 (m, 1H), 3.09 (dd, 1H), 7.39-7.32 (m, 1H), 5.19 (bs, 2H), 4.21 (bd, 1H), 4.08-4.00 (m, 1H), 2.17-2.06 (m, 1H), 1.43, (s, 9H), 0.87 (bd, 3H).

Preparation of Intermediate G3: 8-(tert-Butoxycarbonyl)-3-(3,4-difluorophenyl)-6,6-dimethyl-6,7,8,9-tetrahydro-5H-imidazo[1,5-a][1,4]diazepine-1-carboxylic acid

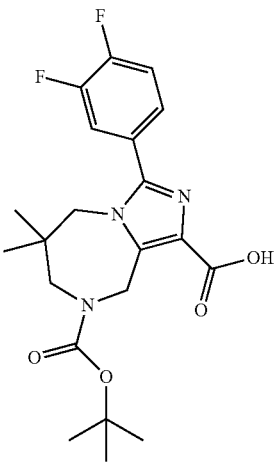

G3

Step 1: Preparation of 1-N-Boc-6,6-dimethyl-1,4-diazepin-3-one: 2,2-dimethyl-1,3-propanediamine (1.02 g, 10.0 mmol) was dissolved by stirring in 15 mL of MeOH. To this solution was added methyl 2-hydroxy-2-methoxy acetate (1.20 g, 10.0 mmol) followed by the addition of methanesulfonic acid (0.65 mL, 10.0 mol). The mixture was stirred at room temperature for 45 minutes and transferred to a Parr bottle, diluted with 25 mL MeOH and treated with 10% palladium on carbon (0.533 g, 0.5 mmol). The mixture was hydrogenated at 50 psi overnight. The mixture was then filtered through celite and the celite pad was washed with MeOH and the filtrate was concentrated in vacuo. The residue was redissolved in 40 mL MeOH and cooled in an ice bath to below 10° C. in an ice-water bath. Sodium methoxide (0.81 g, 15.0 mmol) was added and the mixture was heated to reflux for 2 hours and then cooled to less than 20° C. 0.54 mL water was added followed by the addition of di-tert-butyl dicarbonate (2.18 g, 10.0 mmol) and the mixture stirred overnight. Water (25 mL) was added and the mixture concentrated in vacuo to remove the MeOH. EtOAc (50 mL) was added and the mixture stirred until two clear phases resulted. The phases were separated and the aqueous phase was extracted twice with 25 mL EtOAc. The combined organic phases were washed with 1M aqueous phosphoric acid and brine, dried over sodium sulfate, filtered and concentrated in vacuo. The residue was purified by gradient elution (ISCO RediSep 40, 100% EtOAc to 20% acetonitrile:EtOAc) to give the product, 1-N-Boc-6,6-dimethyl-1,4-diazepin-3-one: 2,2-dimethyl-1,3-propanediamine as a white solid (0.93 g, 38%). LCMS (+ESI) m/z: 187.1 [M+H-56]$^{+1}$ $^1$H-NMR (CDCl$_3$) δ 6.48 (s, 0.4H), 6.22 (s, 0.6H), 4.14-3.98 (bd, 2H), 3.36-3.23 (bd, 2H), 2.98 (d, 2H), 1.46 (s, 9H), 0.94 (s, 6H).

Step 2: Preparation of 1-N-tert-Butoxycarbonyl-3-methoxy-6,6-dimethyl-1,4-diazepine: The product of step 1 (485 mg, 2.0 mmol) was dissolved in 6 mL of DCM and treated with trimethyloxonium tetratfluoroborate (311 mg, 2.1 mmol) and the mixture was stirred at room temperature overnight. The reaction was quenched by the addition of 0.4 mL of saturated aqueous $K_2CO_3$, and poured into 10 mL of DCM and 10 mL of saturated aqueous $NaHCO_3$ The layers were separated and the aqueous phase was extracted with 10 mL of DCM. The combined organic fractions were dried over $Na_2SO_4$, filtered and concentrated in vacuo to give 436 mg (85%) of the title compound as a yellow-orange oil that was used directly.

Step 3: Preparation of Methyl 8-(tert-Butoxycarbonyl)-3-(3,4-difluorophenyl)-6,6-dimethyl-6,7,8,9-tetrahydro-5H-imidazo[1,5-a][1,4]diazepine-1-carboxylate: The product from step 2 (436 mg, 1.70 mmol) was suspended in 8 mL of toluene and heated to 80° C. Intermediate A1 (201 mg, 1.02 mmol) was added and stirring continued at 80° C. for 30 minutes. A second portion of intermediate A1 (201 mg, 1.02 mmol) was added and heating continued for an additional 60 minutes. The mixture was cooled to room temperature and concentrated in vacuo. The residue was dissolved in 20 mL MeOH and treated with sodium methoxide (220 mg, 4.08 mmol) and the mixture heated to 65° C. for 3 hours and then allowed to cool to room temperature overnight. The reaction mixture was treated carefully with 0.36 mL of concentrated aqueous HCl and 10 mL of toluene and the whole concentrated in vacuo. The residue was purified by column chromatography (ISCO RediSep 24 gradient 50% to 100% EtOAc:hexanes) to give 390 mg (53%) of the title compound as a light yellow foam. LCMS (+ESI) m/z: 436.2 $[MH]^{+1}$, 380.1 $[MH-56]^{+1}$ $^1$H-NMR ($CDCl_3$) δ 7.20 (m, 1H), 7.14-7.05 (m, 2H), 5.13-4.56 (bs, 2H), 4.31-4.18 (dd, 2H), 3.69 (s, 3H), 3.39-3.04 (bs, 2H), 1.28 (s, 9H), 0.68 (s, 6H).

Step 4: Preparation of Intermediate G3: 8-(tert-Butoxycarbonyl)-3-(3,4-difluorophenyl)-6,6-dimethyl-6,7,8,9-tetrahydro-5H-imidazo[1,5-a][1,4]diazepine-1-carboxylic acid: The product from step 3 above (145 mg, 0.33 mmol) was dissolved in 2.6 mL MeOH and treated 4M aqueous sodium hydroxide (1.0 mL, 4.0 mmol) and the mixture was heated to 50° C. for 60 minutes. After cooling to room temperature, the mixture was concentrated in vacuo. The residue was dissolved in 5 mL water and cooled in an ice bath. 1M aqueous $H_3PO_4$ was added until a pH of 1 was reached and then the mixture was extracted three times with 15 mL 4:1 $CHCl_3$:iPrOH. The combined organics were dried over $MgSO_4$, filtered and concentrated in vacuo. The residue was dried in a vacuum oven overnight to provide 136 mg (97%) methyl 8-(tert-butoxy-carbonyl)-3-(3,4-difluorophenyl)-6,6-dimethyl-6,7,8,9-tetrahydro-5H-imidazo[1,5-a][1,4]diazepine-1-carboxylate as an off-white solid. LCMS (+ESI) m/z: 422.2 $[MH]^{+1}$, 366.2 $[MH-56]^{+1}$ $^1$H-NMR (DMSO d6) δ 12.26 (bs, 1H), 7.64-7.52 (m, 2H), 7.35 (m, 1H), 5.21-4.61 (bs, 2H), 3.94 (bs, 2H), 3.47-3.24 (bs, 2H), 1.34 (s, 9H), 0.70 (bs, 6H).

EXAMPLES

The following compounds are non-limiting examples contemplated within the scope of the present invention and can be prepared by one or more of the above-described methods:

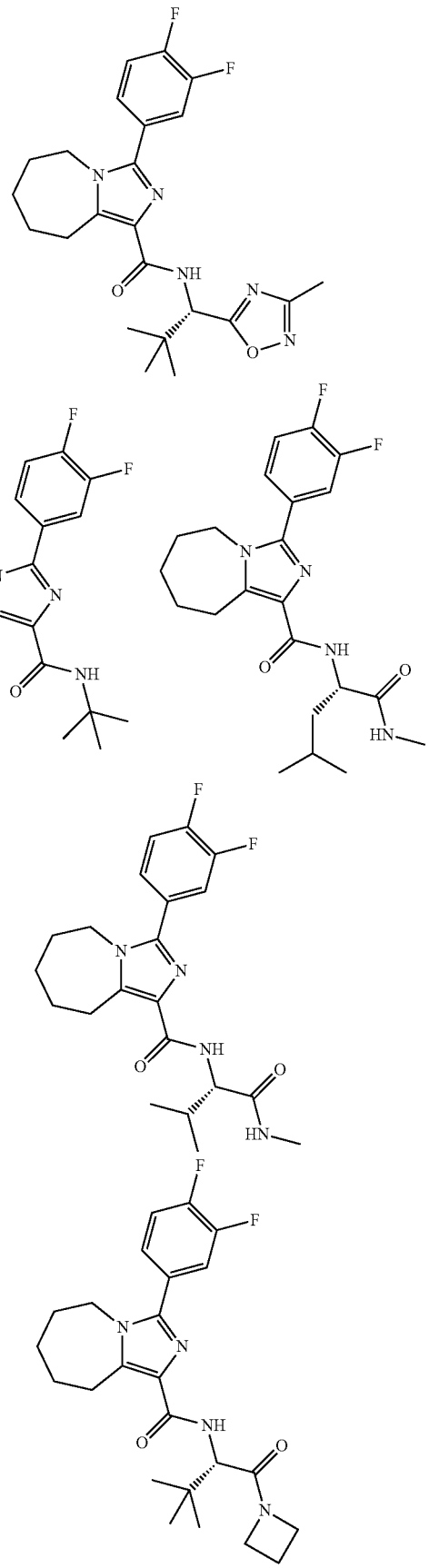

-continued
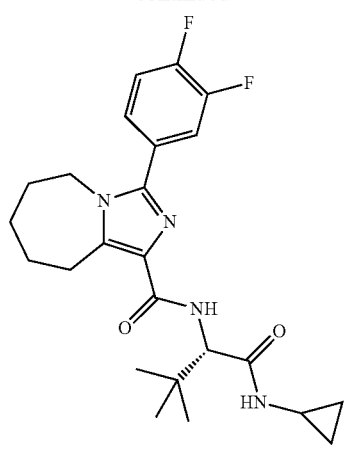
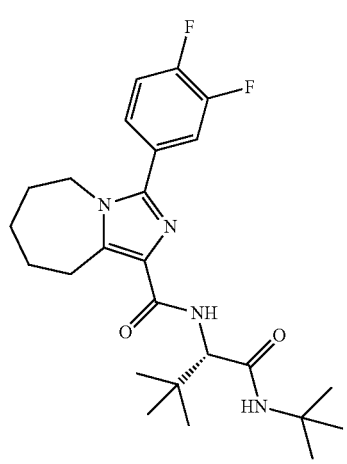
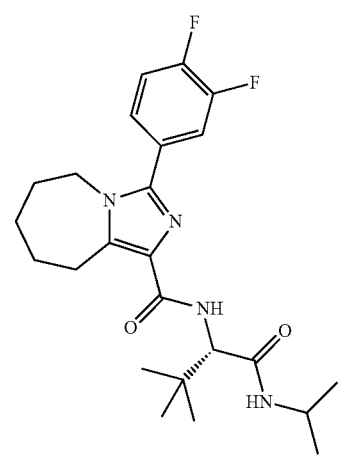
-continued
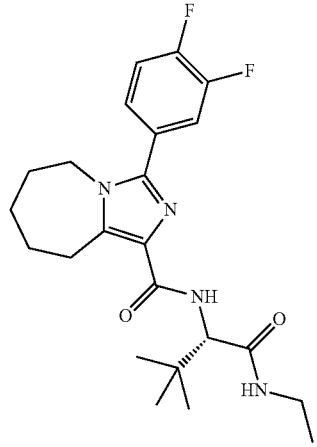
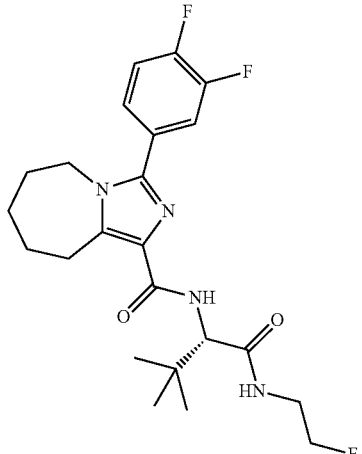
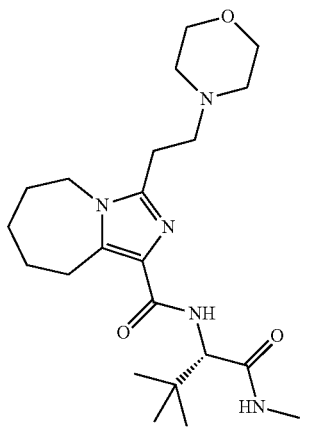
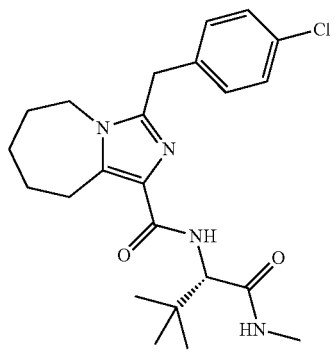

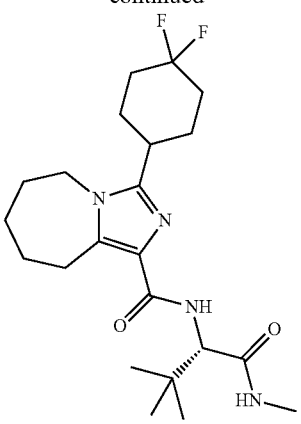
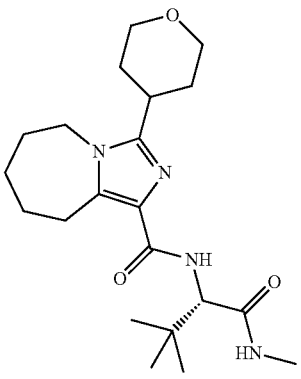
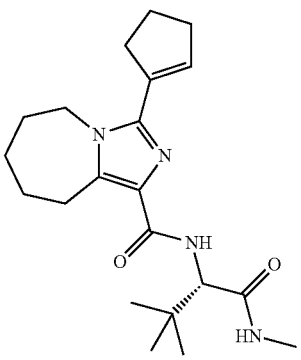
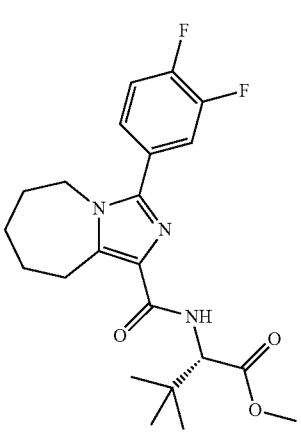
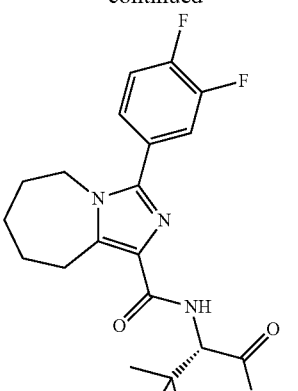
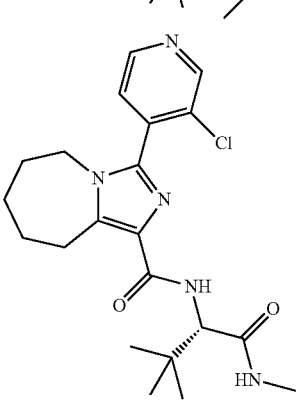
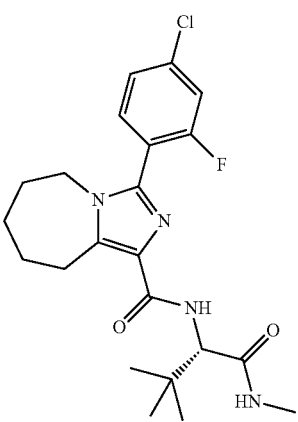
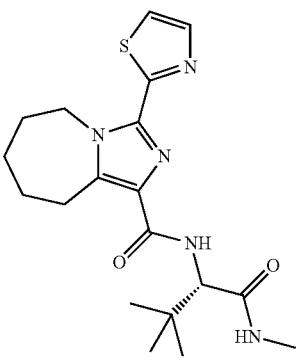

-continued
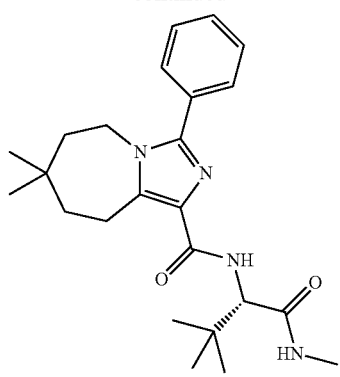
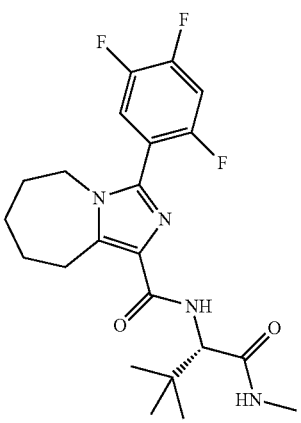
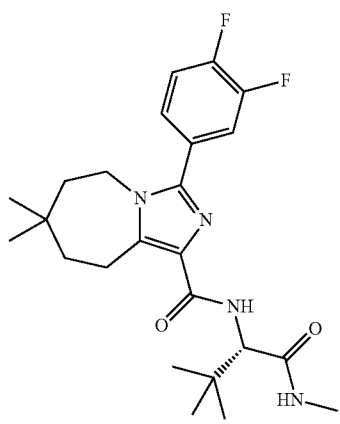
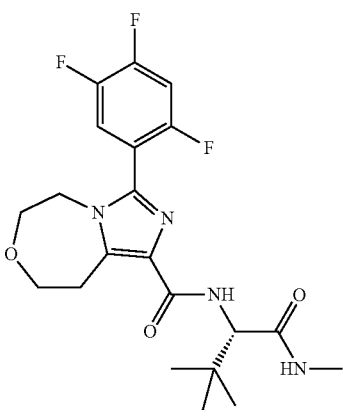
-continued
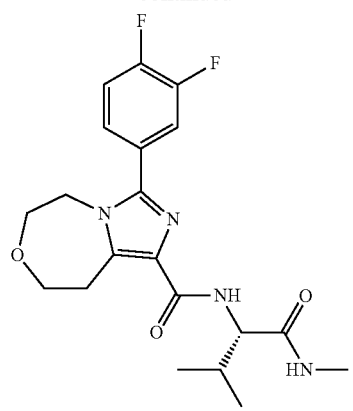
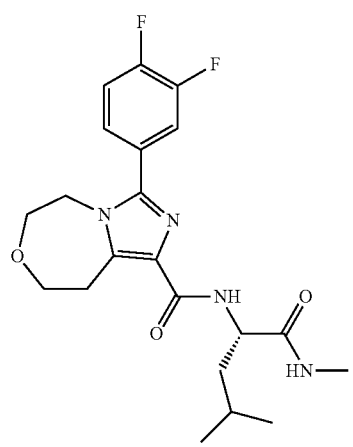
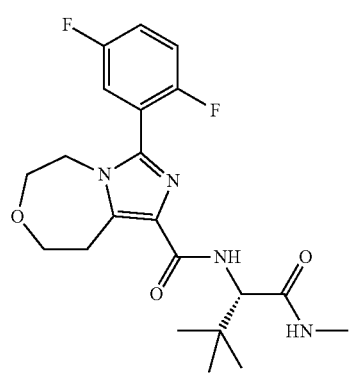
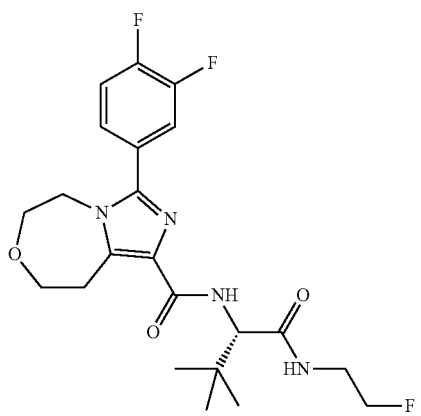

49
-continued
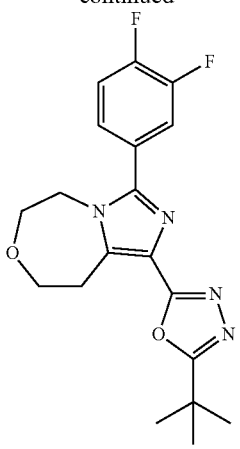
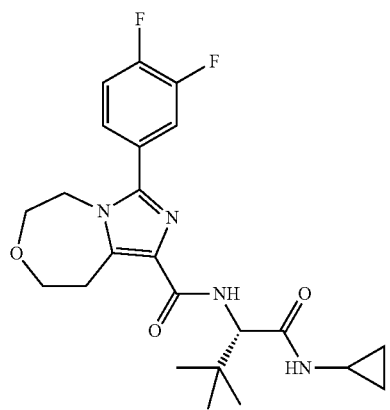
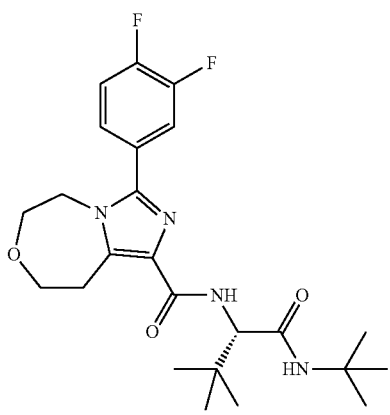
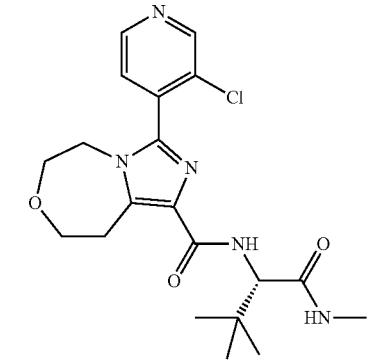
50
-continued
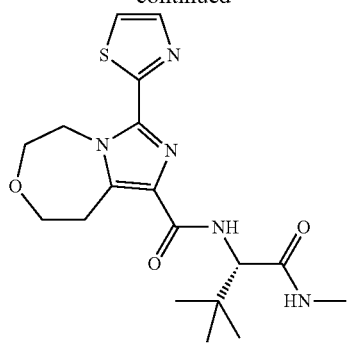
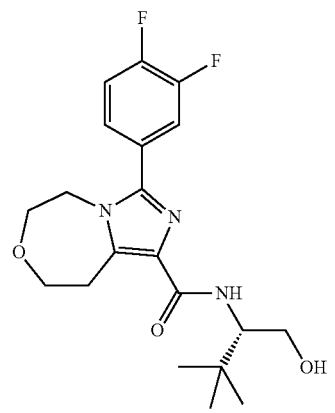
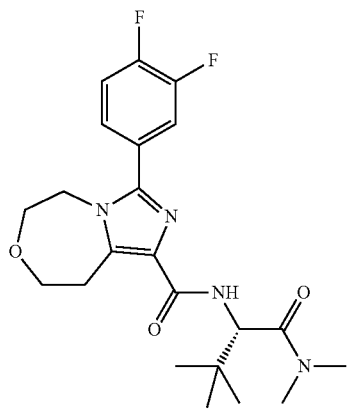
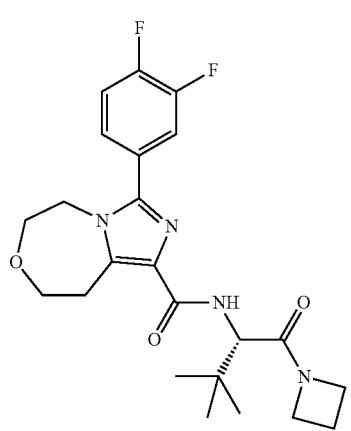

51
-continued
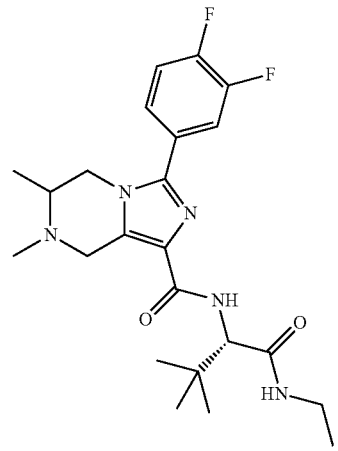
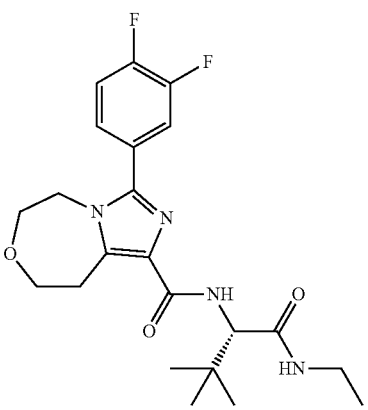
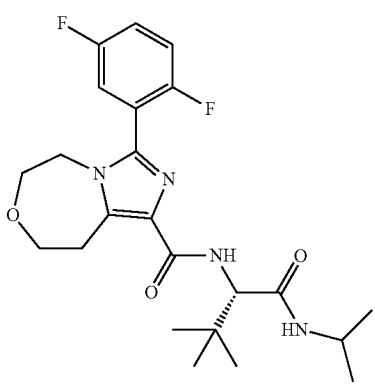
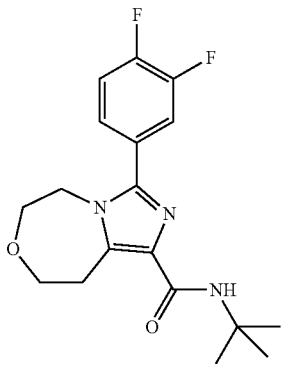
52
-continued
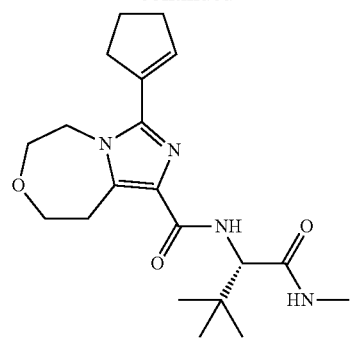
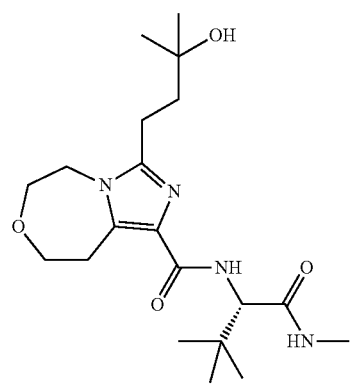
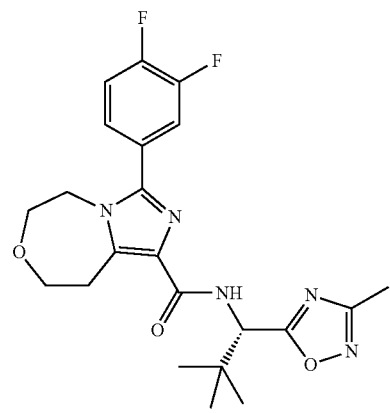
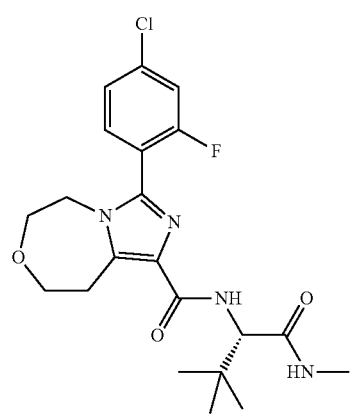

53
-continued
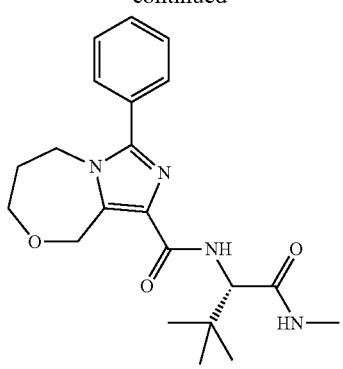
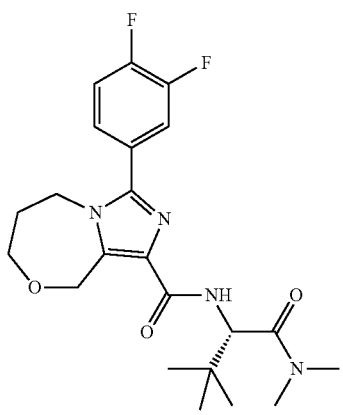
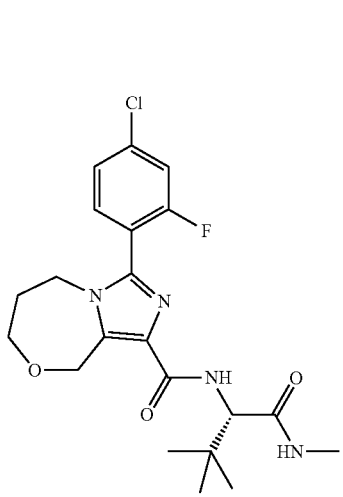
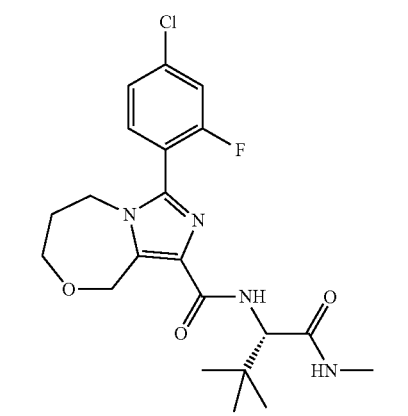
54
-continued
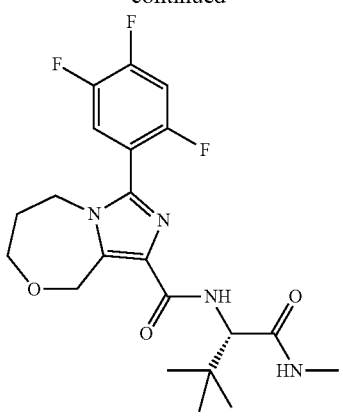
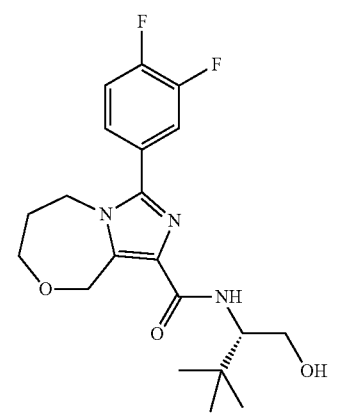
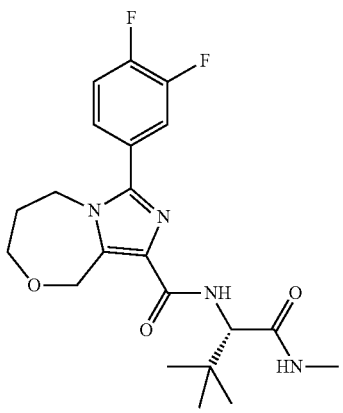
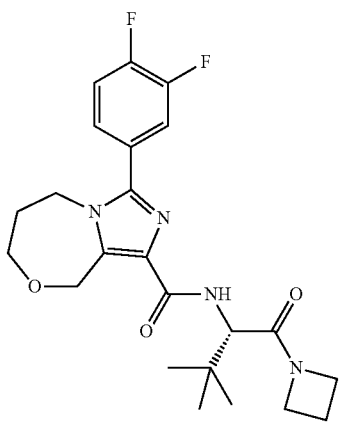

55
-continued
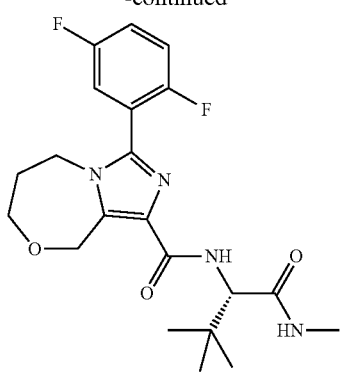
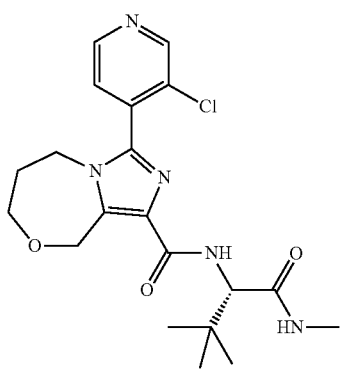
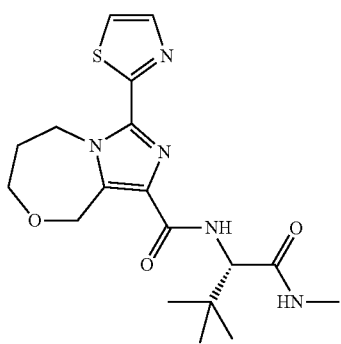
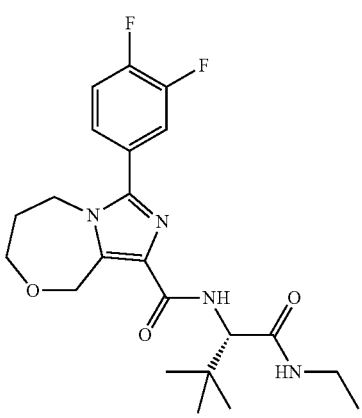
56
-continued
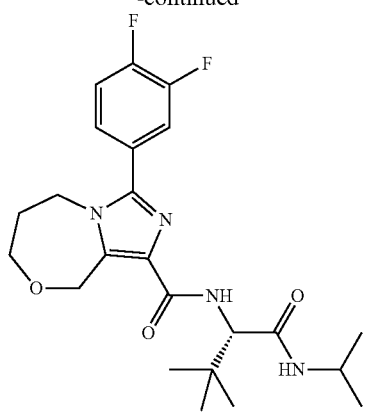
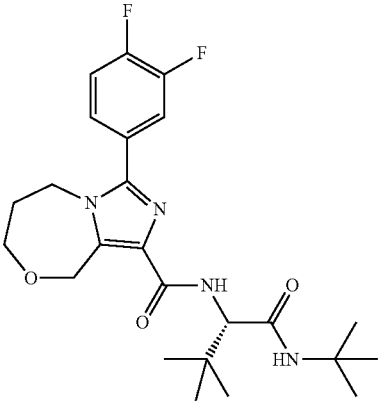
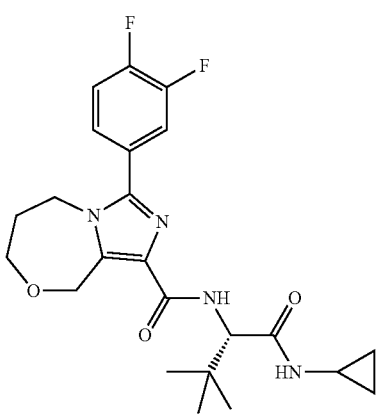
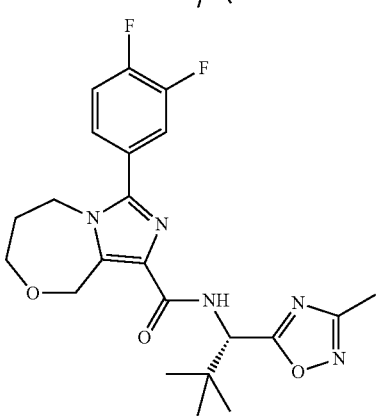

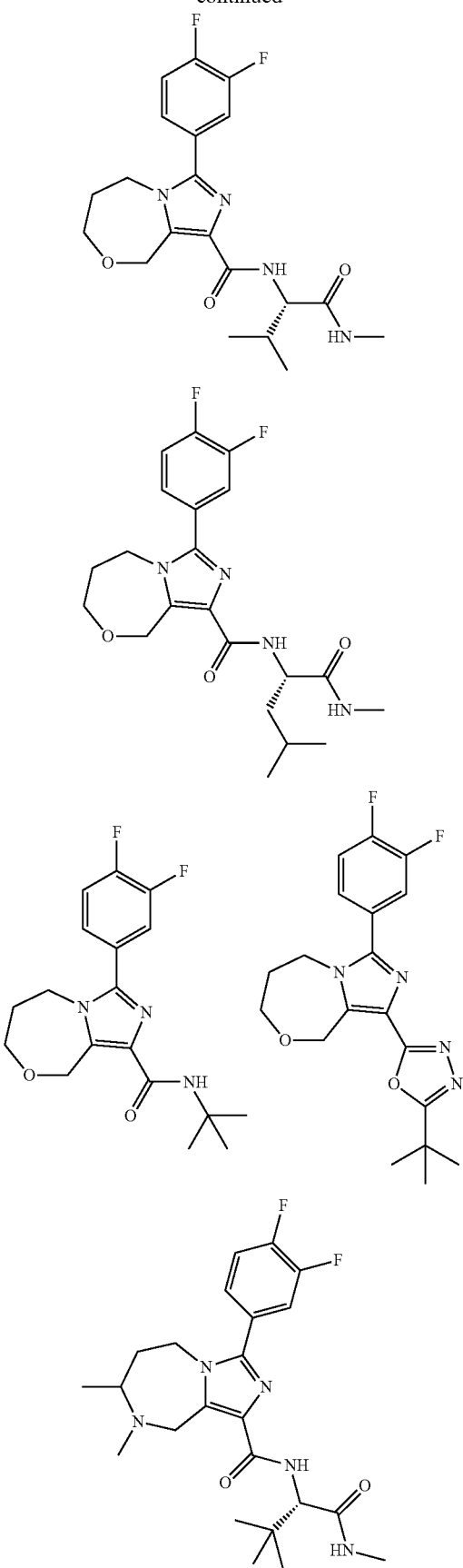
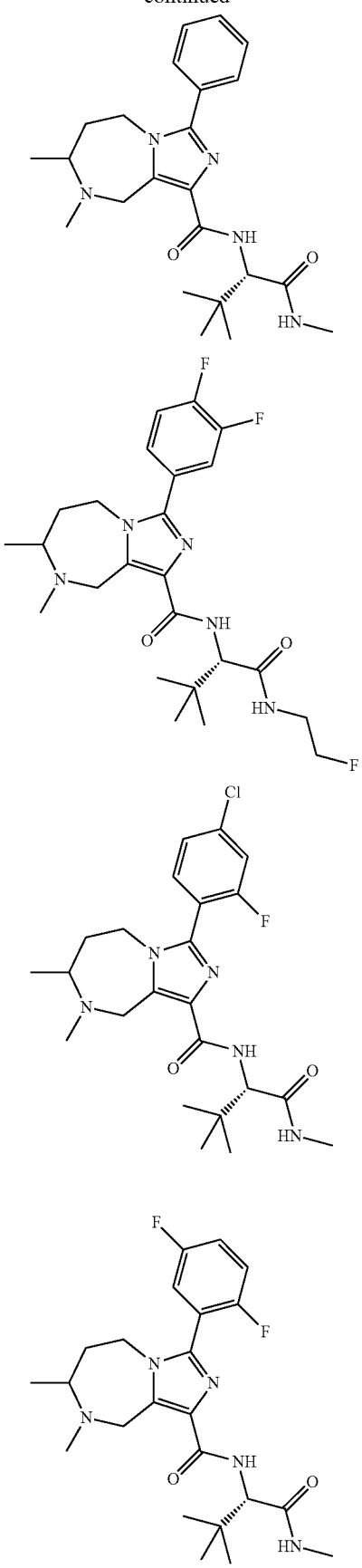

59
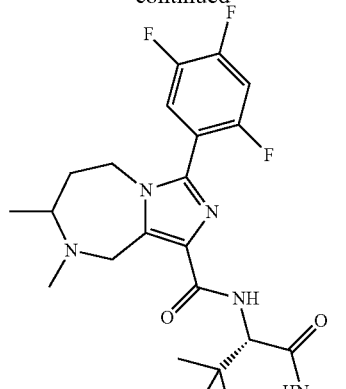
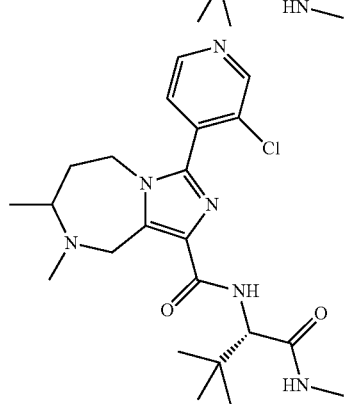
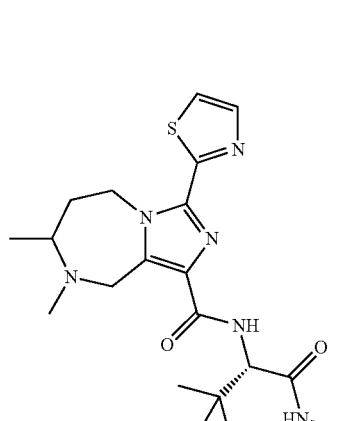
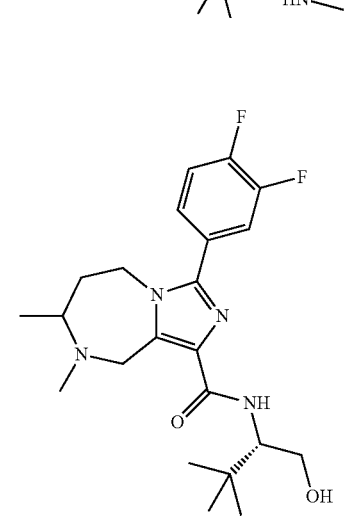
60
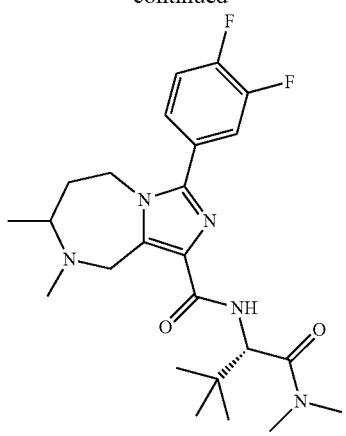
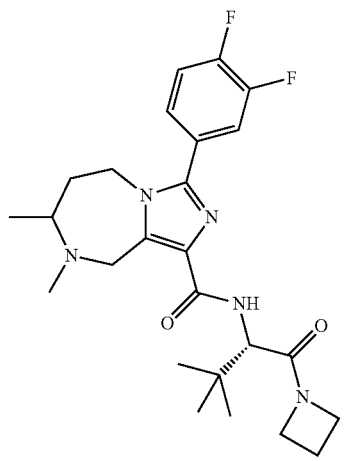
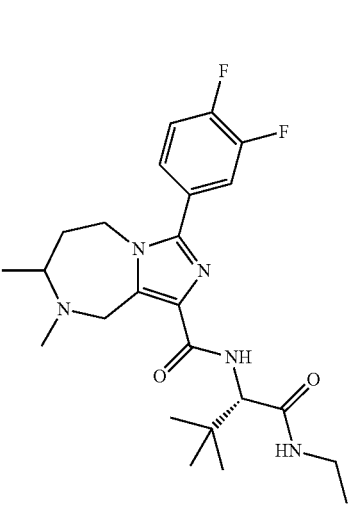

61
-continued
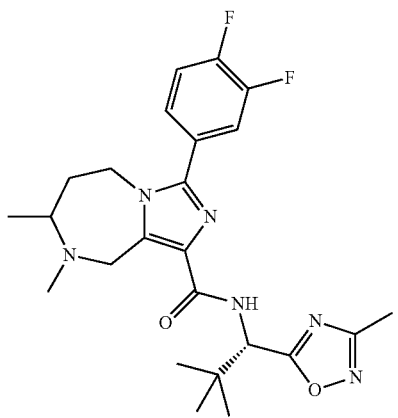
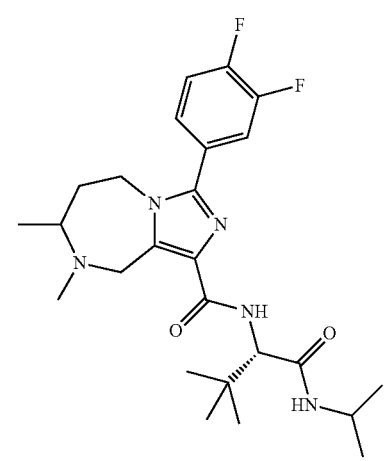
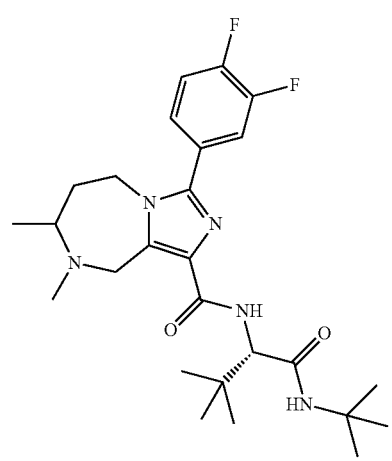
62
-continued
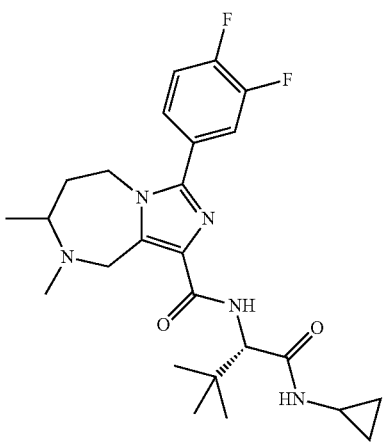
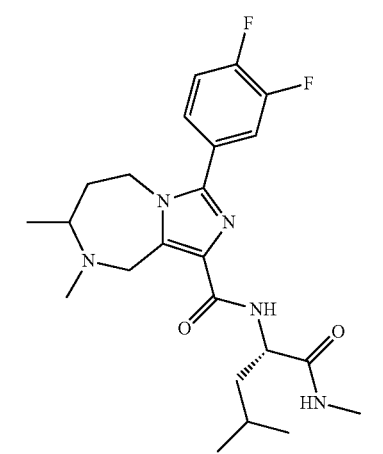
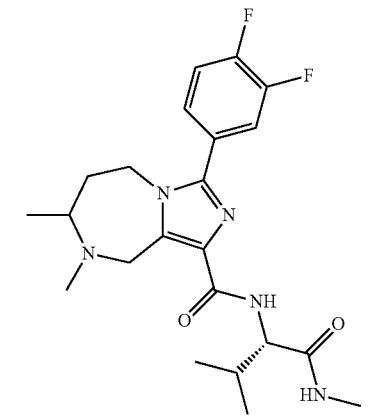
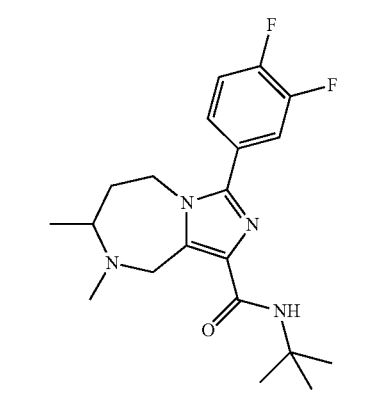

-continued
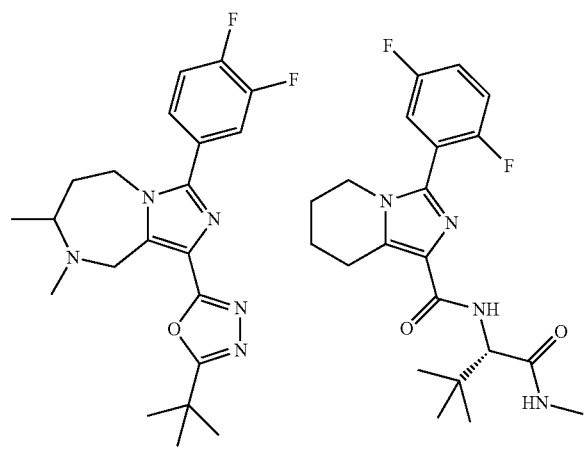
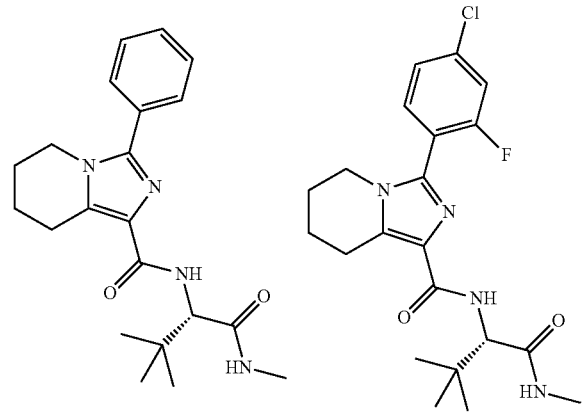
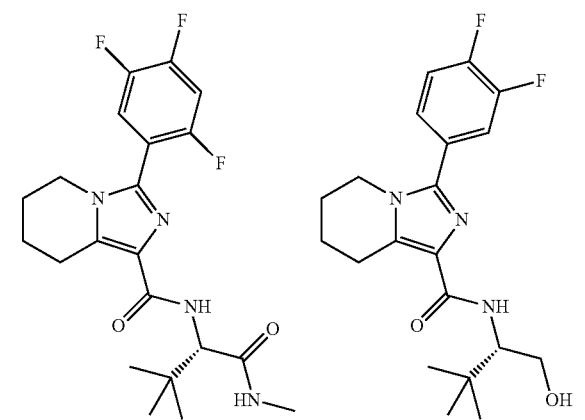
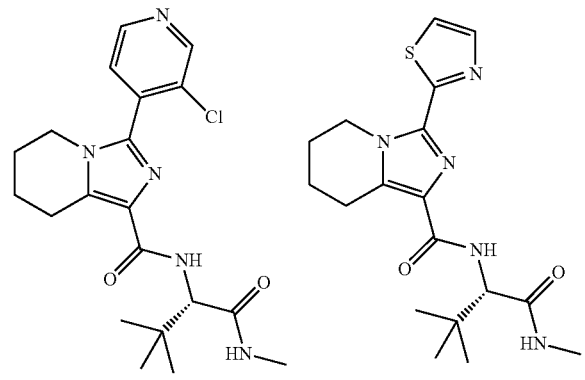
-continued
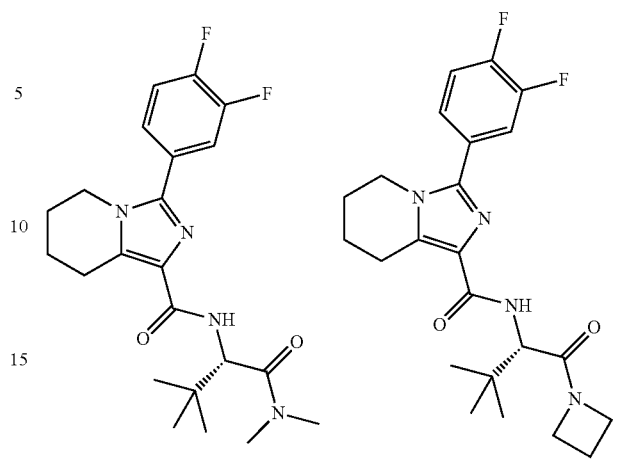
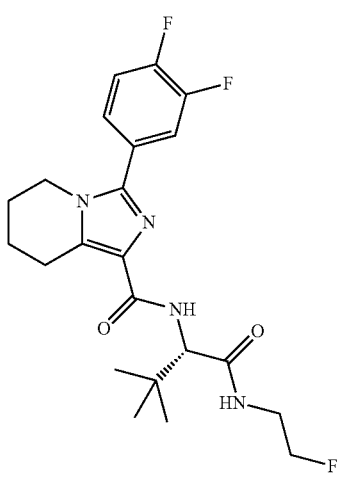
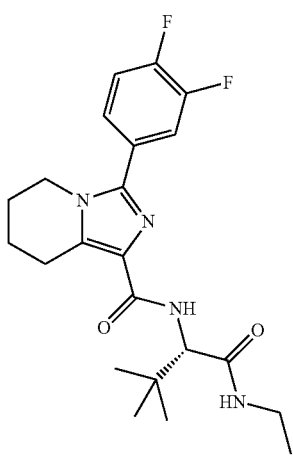

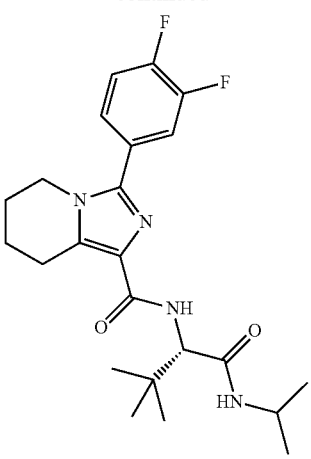
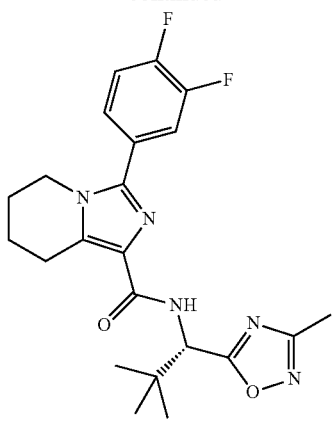
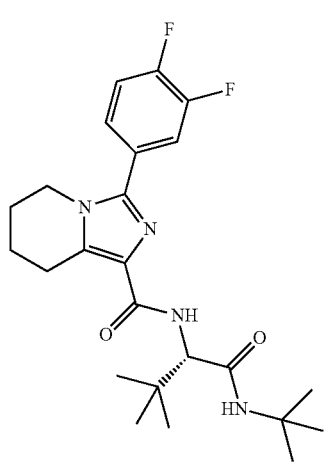
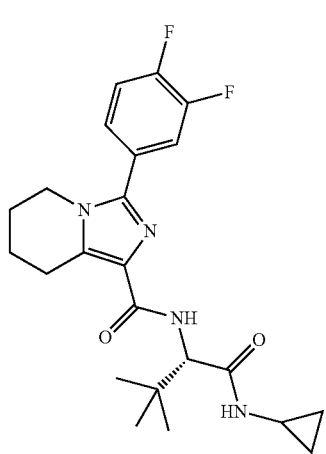
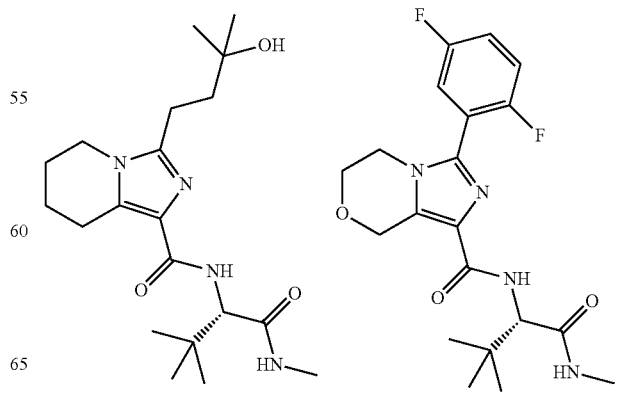

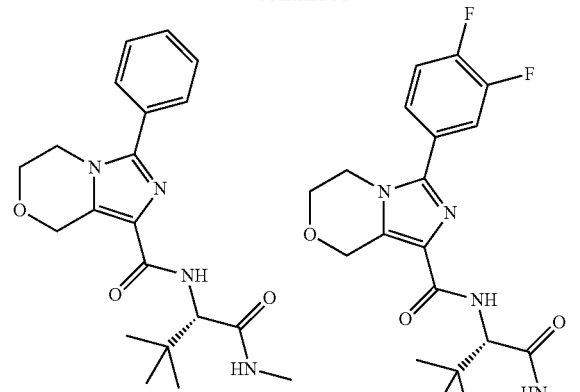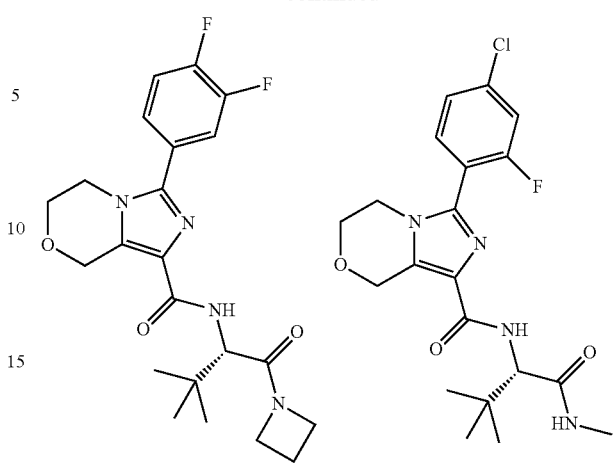

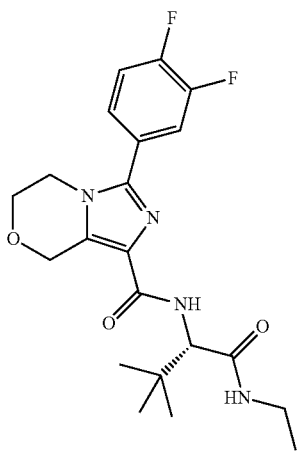
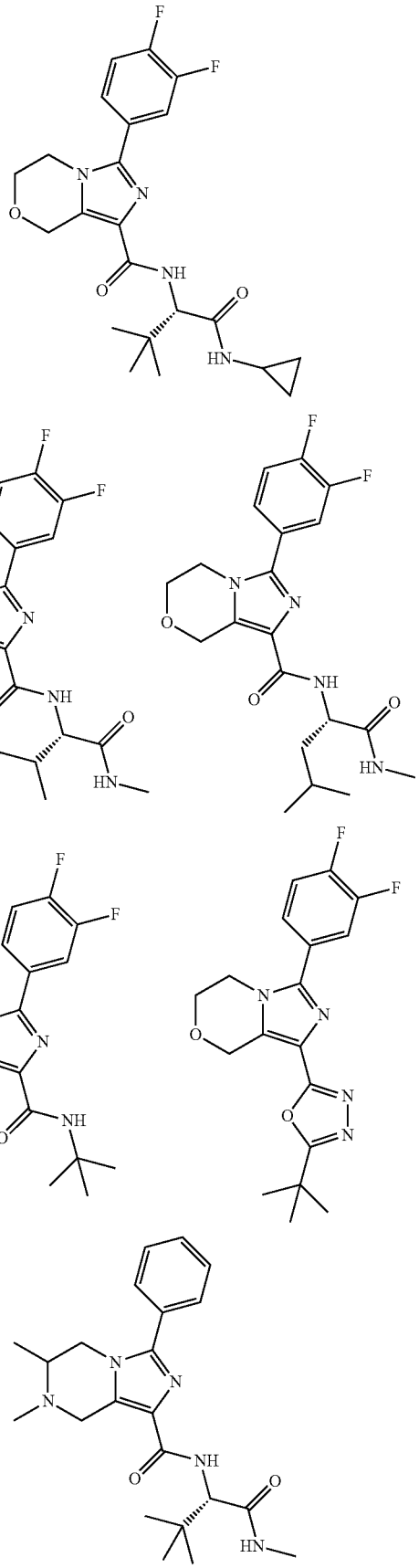

-continued
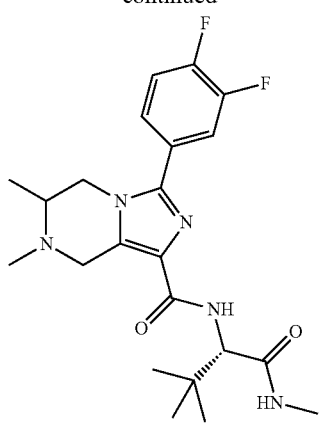
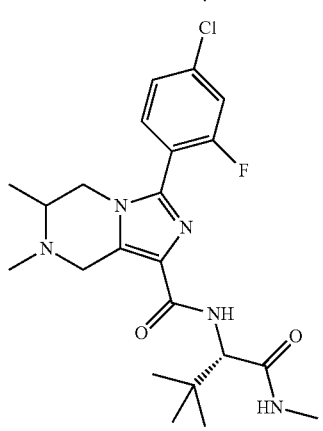
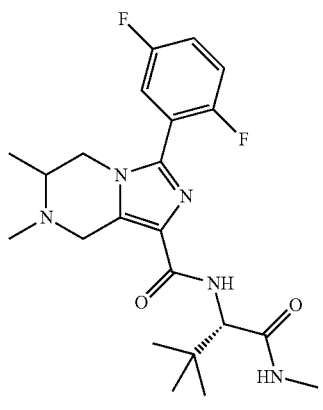
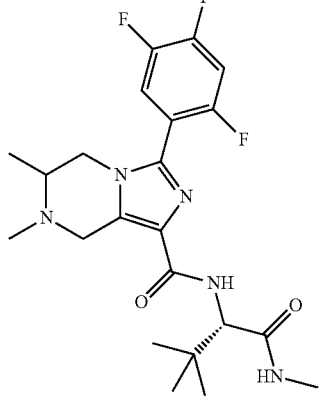
-continued
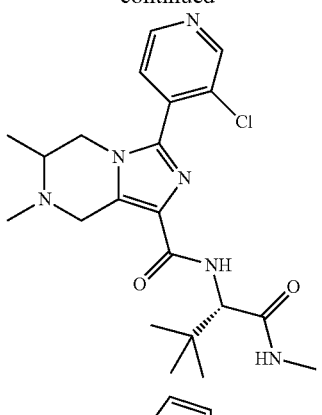
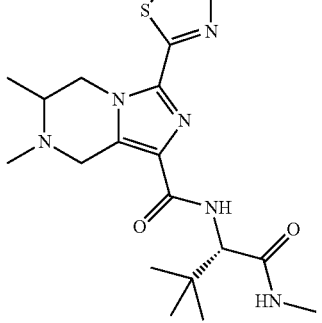
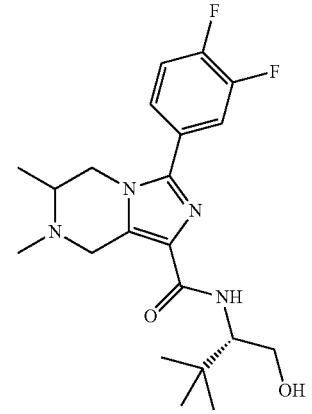
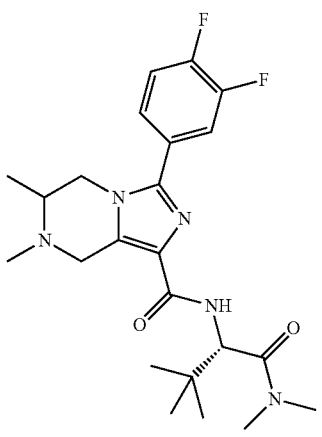

73
-continued
74
-continued
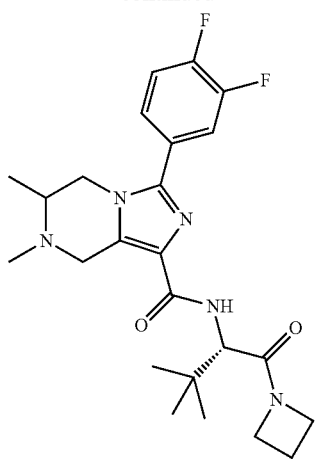
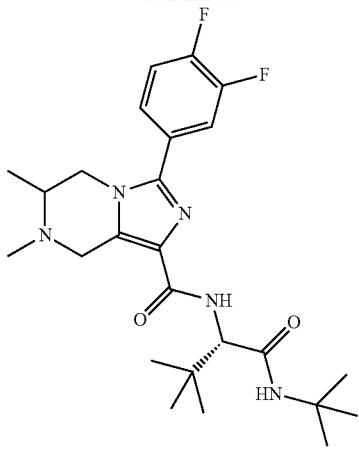
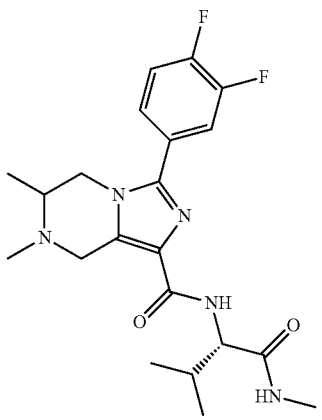

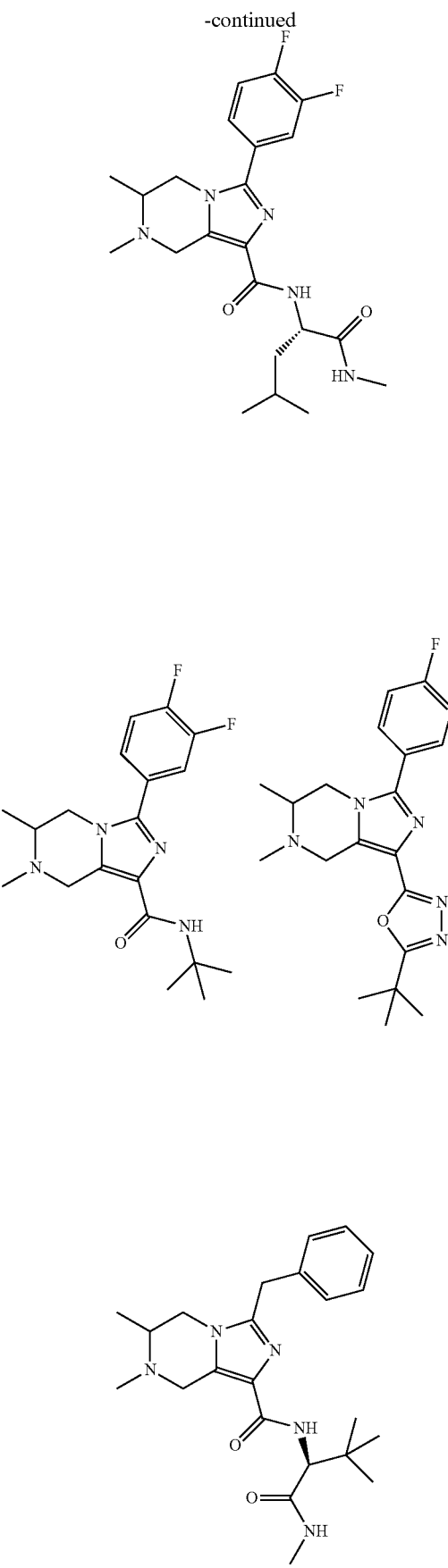

Example 1

Preparation of 1-1: (S)—N-(3,3-dimethyl-1-(methylamino)-1-oxobutan-2-yl)-3-phenyl-6,7,8,9-tetrahydro-5H-imidazo[1,5-a]azepine-1-carboxamide

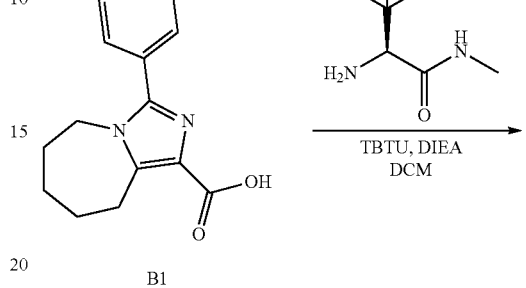

B1

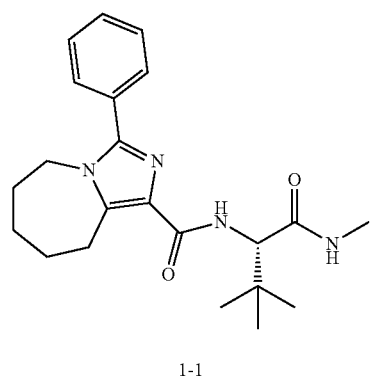

1-1

3-phenyl-6,7,8,9-tetrahydro-5H-imidazo[1,5-a]azepine-1-carboxylic acid (Intermediate B1) (100 mg, 0.390 mmol) was dissolved in DCM (10 mL) in a 40 mL screw-cap vial. (S)-2-amino-N,3,3-trimethylbutanamide (59.1 mg, 0.410 mmol) and DIEA (204 µl, 1.171 mmol) were added, followed by TBTU (132 mg, 0.410 mmol), and the reaction was stirred for 3 hours. LCMS showed complete consumption of starting material. The solution was extracted with saturated aqueous sodium bicarbonate (10 mL) and the organic layer was removed. The aqueous layer was extracted with DCM (10 ml). The combined organic extracts were dried with anhydrous sodium sulfate, filtered and evaporated under reduced pressure to a brown oil which was purified by flash chromatography (silica gel, 25% Hex/EtOAc to 100% EtOAc). Fractions were combined to yield the desired (S)—N-(3,3-dimethyl-1-(methylamino)-1-oxobutan-2-yl)-3-phenyl-6,7,8,9-tetrahydro-5H-imidazo[1,5-a]azepine-1-carboxamide as a white solid (133 mg, 89%). LCMS (+ESI) m/z 383.2 [MH]$^+$. $^1$H-NMR (CDCl$_3$) δ 7.90 (d, 1H), 7.45-7.55 (m, 5H), 5.90 (m, 1H), 4.30 (d, 1H), 4.05 (m, 2H), 3.40 (m, 2H), 2.80 (d, 3H), 1.90 (m, 2H), 1.80 (m, 2H), 1.65 (m, 2H), 1.10 (s, 9H).

The compounds listed in Table 3 were prepared using the procedure described for the synthesis of compound 1-1. These compounds were prepared by treating the appropriate intermediate described above with the appropriate amine. For example, compound 1-2 ((S)-3-(3,4-difluorophenyl)-N-(3,3-dimethyl-1-(methylamino)-1-oxobutan-2-yl)-6,7,8,9-tetrahydro-5H-imidazo[1,5-a]azepine-1-carboxamide) was prepared by reacting intermediate B2 with (S)-2-amino-N,3,3-trimethylbutanamide.

Similarly, compound 1-3: (S)-3-(2,5-difluorophenyl)-N-(3,3-dimethyl-1-(methyl-amino)-1-oxobutan-2-yl)-6,7,8,9-tetrahydro-5H-imidazo[1,5-a]azepine-1-carboxamide, was prepared by reacting intermediate B3 with (S)-2-amino-N,3,3-trimethylbutanamide.

Compound 1-4 is (S)—N-(1-(azetidin-1-yl)-3,3-dimethyl-1-oxobutan-2-yl)-3-phenyl-6,7,8,9-tetrahydro-5H-imidazo[1,5-a]azepine-1-carboxamide.

Compound 1-5 is (S)—N-(1-(azetidin-1-yl)-3,3-dimethyl-1-oxobutan-2-yl)-3-(2,5-difluorophenyl)-6,7,8,9-tetrahydro-5H-imidazo[1,5-a]azepine-1-carboxamide.

Compound 1-6 is (S)-3-(3,4-difluorophenyl)-N-(1-hydroxy-3,3-dimethylbutan-2-yl)-6,7,8,9-tetrahydro-5H-imidazo[1,5-a]azepine-1-carboxamide.

Compound 1-7 is (S)-3-(3,4-difluorophenyl)-N-(3,3-dimethyl-1-(methyl-amino)-1-oxobutan-2-yl)-5,6,7,8-tetrahydroimidazo[1,5-a]pyridine-1-carboxamide. This compound was prepared by reacting intermediate C1 with (S)-2-amino-N,3,3-trimethylbutanamide.

Compound 1-8 is (S)—N-(3,3-dimethyl-1-(methylamino)-1-oxobutan-2-yl)-3-phenyl-5,6,8,9-tetrahydroimidazo[1,5-d][1,4]oxazepine-1-carboxamide.

Compound 1-9 is (S)-3-(3,4-difluorophenyl)-N-(3,3-dimethyl-1-(methyl-amino)-1-oxobutan-2-yl)-5,6,8,9-tetrahydroimidazo[1,5-d][1,4]oxazepine-1-carboxamide. This compound was prepared by reacting intermediate D2 with (S)-2-amino-N,3,3-trimethylbutanamide.

1-10 is (S)-3-(3,4-difluorophenyl)-N-(3,3-dimethyl-1-(methylamino)-1-oxobutan-2-yl)-5,6,7,9-tetrahydroimidazo[5,1-c][1,4]oxazepine-1-carboxamide.

1-11 is (S)-3-(3,4-difluorophenyl)-N-(1-(2-hydroxyethylamino)-3,3-dimethyl-1-oxobutan-2-yl)-5,6,7,9-tetrahydroimidazo[5,1-c][1,4]oxazepine-1-carboxamide.

1-12 is (S)-3-(2,5-difluorophenyl)-N-(3,3-dimethyl-1-(methylamino)-1-oxobutan-2-yl)-5,6,7,9-tetrahydroimidazo[5,1-c][1,4]oxazepine-1-carboxamide.

1-13 is (S)-3-(4-chloro-2-fluorophenyl)-N-(3,3-dimethyl-1-(methylamino)-1-oxobutan-2-yl)-5,6,7,9-tetrahydroimidazo[5,1-c][1,4]oxazepine-1-carboxamide.

1-14 is N-((2S,3S)-1-amino-3-methyl-1-oxopentan-2-yl)-3-(3,4-difluorophenyl)-6,7,8,9-tetrahydro-5H-imidazo[1,5-a]azepine-1-carboxamide.

1-15 is 3-(3,4-difluorophenyl)-N-((1S,2S)-2-hydroxy-2,3-dihydro-1H-inden-1-yl)-6,7,8,9-tetrahydro-5H-imidazo[1,5-a]azepine-1-carboxamide.

1-16 is 3-(3,4-difluorophenyl)-N-((1R,2S)-2-hydroxy-2,3-dihydro-1H-inden-1-yl)-6,7,8,9-tetrahydro-5H-imidazo[1,5-a]azepine-1-carboxamide.

1-17 is 3-(3,4-difluorophenyl)-N-((1R,2R)-2-hydroxy-2,3-dihydro-1H-inden-1-yl)-6,7,8,9-tetrahydro-5H-imidazo[1,5-a]azepine-1-carboxamide.

1-18 is 3-(3,4-difluorophenyl)-N-((1S,2R)-2-hydroxy-2,3-dihydro-1H-inden-1-yl)-6,7,8,9-tetrahydro-5H-imidazo[1,5-a]azepine-1-carboxamide.

1-19 is 3-(3,4-difluorophenyl)-N-(2,3-dihydro-1H-inden-1-yl)-6,7,8,9-tetrahydro-5H-imidazo[1,5-a]azepine-1-carboxamide.

1-20 is (S)-3-(3,4-difluorophenyl)-N-(1,2,3,4-tetrahydronaphthalen-1-yl)-6,7,8,9-tetrahydro-5H-imidazo[1,5-a]azepine-1-carboxamide.

1-21 is (R)-3-(3,4-difluorophenyl)-N-(1,2,3,4-tetrahydronaphthalen-1-yl)-6,7,8,9-tetrahydro-5H-imidazo[1,5-a]azepine-1-carboxamide.

1-22 is (S)—N-(1-(2-fluoroethylamino)-3,3-dimethyl-1-oxobutan-2-yl)-3-phenyl-6,7,8,9-tetrahydro-5H-imidazo[1,5-a]azepine-1-carboxamide.

1-23 is (S)-methyl 2-(3-(3,4-difluorophenyl)-6,7,8,9-tetrahydro-5H-imidazo[1,5-a]azepine-1-carboxamido)-3,3-dimethylbutanoate.

1-24 is (S)-methyl 3,3-dimethyl-2-(3-phenyl-6,7,8,9-tetrahydro-5H-imidazo[1,5-a]azepine-1-carboxamido)butanoate.

TABLE 3

| Compound No. | Structure | m/z | $^1$H NMR |
|---|---|---|---|
| 1-2 | 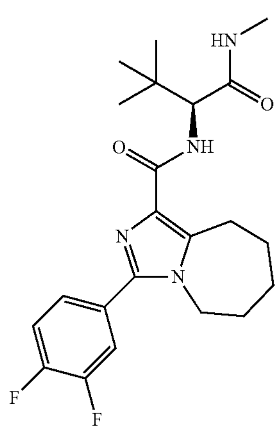 [SMILES: CNC(=O)[C@@H](NC(=O)c1nc(-c2ccc(F)c(F)c2)n2c1CCCCC2)C(C)(C)C] | 419.3 [M + H]$^+$ | (CDCl$_3$) δ 7.88 (bd, 1 H), 7.38 (ddd, 1 H), 7.32-7.24 (m, 2 H), 5.89 (bs, 1 H), 4.30 (d, 1 H), 4.03 (dd, 2 H), 3.50-3.22 (m, 2 H), 2.80 (d, 3 H), 1.93-1.81 (m, 2 H), 1.80-1.69 (m, 4 H), 1.08 (s, 9 H). |

TABLE 3-continued

| Compound No. | Structure | m/z | ¹H NMR |
|---|---|---|---|
| 1-3 | 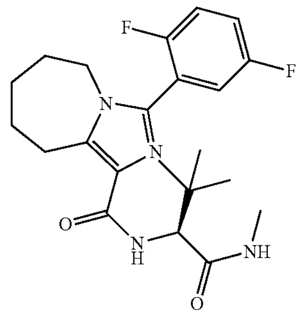 [SMILES: CNC(=O)[C@@H](NC(=O)c1nc(-c2cc(F)ccc2F)n2c1CCCCC2)C(C)(C)C] | 419.3 [M + H]⁺ | (CDCl3) δ 7.84 (d, 1 H), 7.31 (m, 1 H), 7.18-7.09 (m, 2 H), 5.18 (bs, 1 H), 4.28 (d, 1 H), 3.87 (dd, 2 H), 3.38 (m, 2 H), 2.81 (d, 3 H), 1.96-1.84 (m, 2 H), 1.83-1.69 (m, 4 H), 1.09 (s, 9 H). |
| 1-4 | 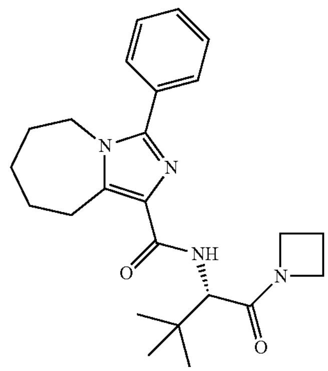 [SMILES: CC(C)(C)[C@H](NC(=O)c1nc(-c2ccccc2)n2c1CCCCC2)C(=O)N1CCC1] | 409.3 [M + H]⁺ | (CDCl3) δ 7.90 (d, 1 H), 7.60-7.40 (m, 5 H), 5.90 (m, 1 H), 4.50 (d, 1 H), 4.50 (dt, 1 H), 4.27 (dt, 1 H), 4.15-3.95 (m, 4 H), 3.40 (m, 2 H), 2.25 (m, 2 H), 1.95-1.70 (m, 6 H), 1.10 (s, 9 H). |
| 1-5 | 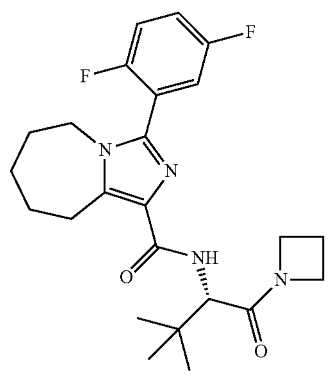 [SMILES: CC(C)(C)[C@H](NC(=O)c1nc(-c2cc(F)ccc2F)n2c1CCCCC2)C(=O)N1CCC1] | 445.2 [M + H]⁺ | |
| 1-6 | 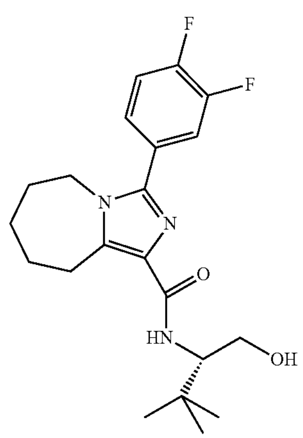 | 356.2 [M + H]⁺ | (CDCl3) δ 7.33 (m, 1 H), 7.13-7.24 (m, 5 H), 3.94 (m, 2 H), 3.85 (m, 2 H), 3.54 (dt, 1 H), 3.30 (m, 2 H), 1.80 (m, 2 H), 1.70 (m, 4 H,) 0.95 (s, 9 H). |

TABLE 3-continued

| Compound No. | Structure | m/z | ¹H NMR |
|---|---|---|---|
| 1-7 | 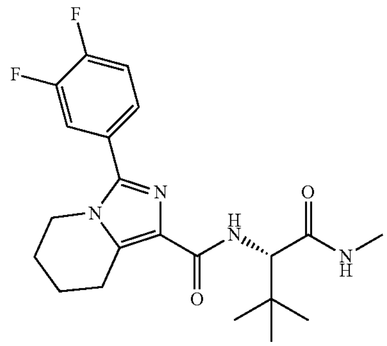 [SMILES: CNC(=O)[C@@H](NC(=O)c1nc(-c2ccc(F)c(F)c2)n2c1CCCC2)C(C)(C)C] | 405.2 [M + H]⁺ | (CDCl3) δ 7.23 (d, 1 H), 7.52 (ddd, 1 H), 7.41 (m, 1 H), 7.30-7.22 (m, 1 H), 5.95 (m, 1 H), 4.03 (m, 2 H), 3.32-3.14 (m, 2 H), 2.81 (d, 3 H), 2.04-1.84 (m, 4 H), 1.10 (s, 9 H). |
| 1-8 | 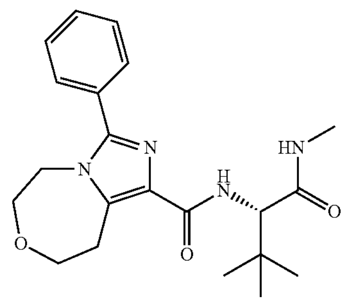 [SMILES: CNC(=O)[C@@H](NC(=O)c1nc(-c2ccccc2)n2c1CCOCC2)C(C)(C)C] | 385.2 [M + H]⁺ | (CDCl3) δ 7.58-7.40 (m, 6 H), 5.88 (m, 1 H), 4.31 (m, 1 H), 4.26 (m, 2 H), 3.96-3.76 (m, 3 H), 3.74-3.58 (m, 2 H), 2.81 (d, 3 H), 1.10 (s, 9 H). |
| 1-9 | 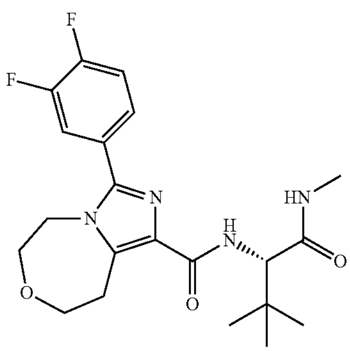 [SMILES: CNC(=O)[C@@H](NC(=O)c1nc(-c2ccc(F)c(F)c2)n2c1CCOCC2)C(C)(C)C] | 421.2 [M + H]⁺ | (CDCl3) δ 7.89 (d, 1 H), 7.38 (ddd, 1 H), 7.33-7.21 (m, 2 H), 5.82 (bs, 1 H), 4.28 (d, 1 H), 4.23 (dd, 2 H), 3.95-3.74 (m, 4 H), 3.73-3.57 (m, 2 H), 3.49-3.38 (m, 2 H), 2.82 (d, 3 H), 1.09 (s, 3 H). |
| 1-10 | 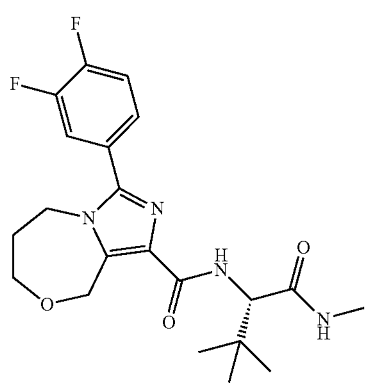 [SMILES: CNC(=O)[C@@H](NC(=O)c1nc(-c2ccc(F)c(F)c2)n2c1COCCC2)C(C)(C)C] | 421.3 [M + H]⁺ | (DMSO d6) δ 8.10 (dd, 1 H) 7.68-7.59 (m, 2 H), 7.59-7.48 (m, 1 H), 7.38 (m, 1 H), 5.02 (s, 2 H), 4.25 (d, 1 H), 4.16 (m, 2 H), 3.86 (m, 2 H), 2.52 (d, 3 H), 1.83-1.70 (m, 2 H), 0.85 (s, 9 H). |

TABLE 3-continued

| Compound No. | Structure | m/z | ¹H NMR |
|---|---|---|---|
| 1-11 | 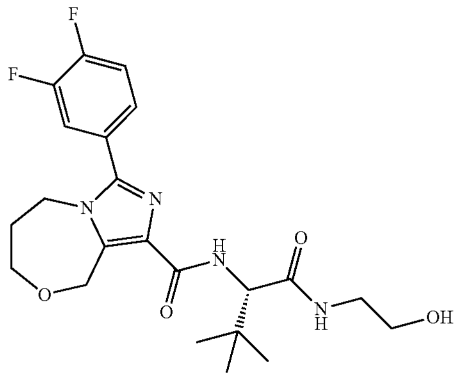 [SMILES: CC(C)(C)[C@H](NC(=O)c1nc(-c2ccc(F)c(F)c2)n2c1COCCC2)C(=O)NCCO] | 451.3 [M + H]⁺ | (DMSO d6) δ 8.27 (t, 1 H) 7.82-7.72 (m, 2 H), 7.72-7.62 (m, 1 H), 7.52 (m, 1 H), 5.15 (s, 2 H), 4.69 (t, 1 H), 4.42 (d, 1 H), 4.29 (m, 2 H), 3.99 (m, 2 H), 3.46 (q, 2 H), 3.29-3.11 (m, 2 H), 2.00-1.85 (m, 2 H), 0.99 (s, 9 H). |
| 1-12 | 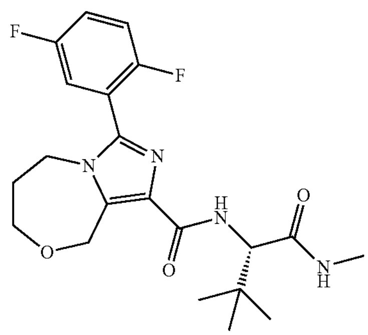 [SMILES: CNC(=O)[C@@H](NC(=O)c1nc(-c2cc(F)ccc2F)n2c1COCCC2)C(C)(C)C] | 421.3 [M + H]⁺ | (DMSO d6) δ 8.10 (m, 1 H) 7.59 (d, 1 H), 7.48-7.40 (m, 3 H), 5.04 (s, 2 H), 4.24 (d, 1 H), 4.06-3.98 (m, 2 H), 3.92-3.83 (m, 2 H), 2.52 (d, 3 H), 1.82-1.69 (m, 2 H), 0.85 (s, 9 H). |
| 1-13 | 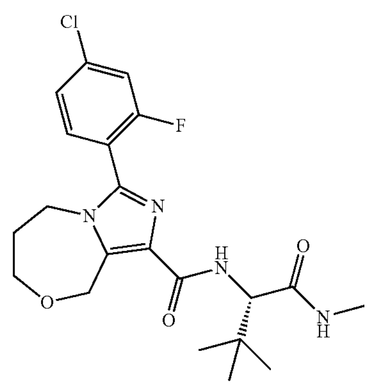 [SMILES: CNC(=O)[C@@H](NC(=O)c1nc(-c2ccc(Cl)cc2F)n2c1COCCC2)C(C)(C)C] | 437.3 [M + H]⁺ | (DMSO d6) δ 8.16 (m, 1 H) 7.73-7.60 (m, 3 H), 7.48 (dd, 1 H), 5.09 (s, 2 H), 4.30 (d, 1 H), 4.07 (m, 2 H), 3.93 (m, 2 H), 2.58 (d, 3 H), 1.86-1.76 (m, 2 H), 0.90 (s, 9 H). |
| 1-14 | 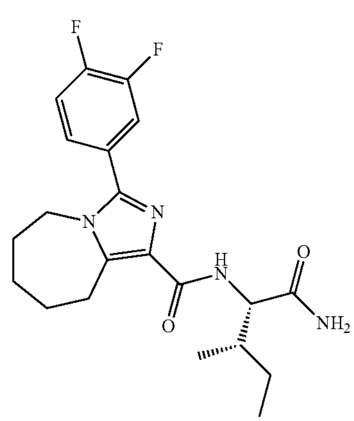 [SMILES: CC[C@H](C)[C@H](NC(=O)c1nc(-c2ccc(F)c(F)c2)n2c1CCCCC2)C(N)=O] | 405.2 [M + H]⁺ | (CDCl₃) δ 7.64 (s, 1 H), 7.43-7.35 (m, 1 H), 7.34-7.24 (m, 2 H), 6.15 (bs, 1 H), 5.36 (bs, 1 H), 4.44 (dd, 1 H), 4.04 (m, 2 H), 3.46-3.30 (m, 2 H), 2.20-2.09 (m, 1 H), 1.96-1.86 (m, 2 H), 1.84-1.72 (m, 4 H), 1.69-1.58 (m, 2 H), 1.30-1.17 (m, 1 H), 1.03 (d, 3 H), 0.95 (t, 3 H). |

TABLE 3-continued

| Compound No. | Structure | m/z | ¹H NMR |
|---|---|---|---|
| 1-15 | 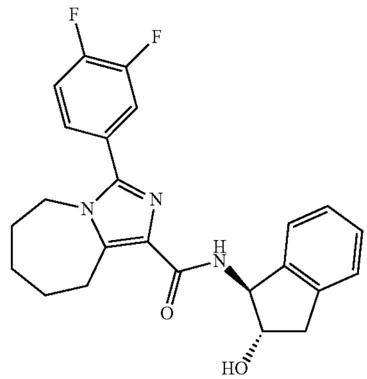 [SMILES: O=C(N[C@H]1c2ccccc2C[C@@H]1O)c1nc(-c2ccc(F)c(F)c2)n2c1CCCCC2] | 424.2 [M + H]⁺ | (CDCl₃) δ 7.82 (bs, 1 H), 7.46-7.25 (m, 7 H), 6.15 (bs, 1 H), 5.33 (t, 1 H), 4.58 (ddd, 1 H), 4.10 (m, 2 H), 3.48 (bs, 2 H), 3.39 (dd, 1 H), 3.04 (dd, 1 H), 2.03-1.91 (m, 2 H), 1.91-1.78 (m, 4 H). |
| 1-16 | 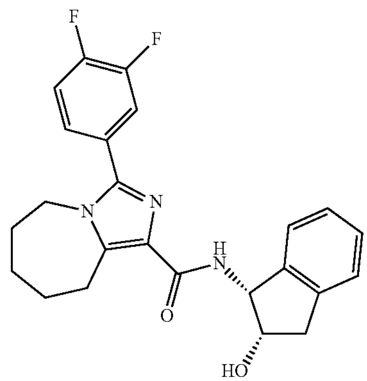 [SMILES: O=C(N[C@@H]1c2ccccc2C[C@@H]1O)c1nc(-c2ccc(F)c(F)c2)n2c1CCCCC2] | 424.2 [M + H]⁺ | (CDCl₃) δ 7.79 (bs, 1 H), 7.40-7.32 (m, 2 H), 7.31-7.20 (m, 5 H), 5.55 (m, 1 H), 4.74 (ddd, 1 H), 4.06 (m, 2 H), 3.47 (bs, 2 H), 3.22 (dd, 1 H), 3.05 (dd, 1 H), 1.96-1.87 (m, 2 H), 1.87-1.74 (m, 4 H). |
| 1-17 | 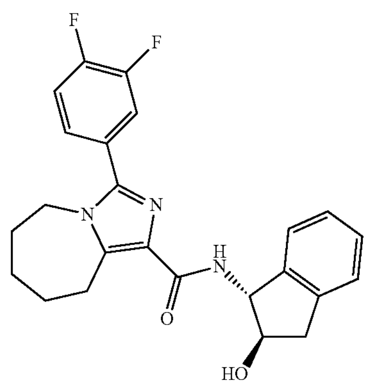 [SMILES: O=C(N[C@@H]1c2ccccc2C[C@H]1O)c1nc(-c2ccc(F)c(F)c2)n2c1CCCCC2] | 424.2 [M + H]⁺ | (CDCl₃) δ 7.79 (bs, 1 H), 7.36-7.25 (m, 2 H), 7.24-7.14 (m, 5 H), 5.21 (t, 1 H), 4.48 (m, 1 H), 3.99 (m, 2 H), 3.37 (bs, 2 H), 3.26 (dd, 1 H), 2.91 (dd, 1 H), 1.91-1.80 (m, 2 H), 1.80-1.66 (m, 4 H), 1.49 (bs, 1 H). |
| 1-18 | 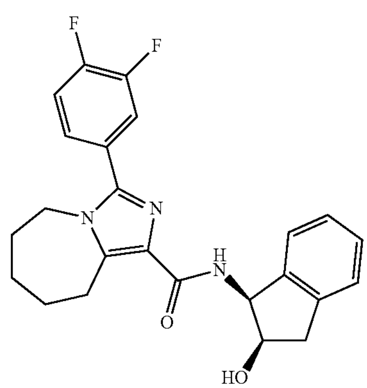 [SMILES: O=C(N[C@H]1c2ccccc2C[C@H]1O)c1nc(-c2ccc(F)c(F)c2)n2c1CCCCC2] | 424.2 [M + H]⁺ | (CDCl₃) δ 7.28 (bs, 1 H), 7.38-7.30 (m, 2 H), 7.30-7.18 (m, 5 H), 5.54 (m, 1 H), 4.73 (m, 1 H), 4.04 (m, 2 H), 3.45 (bs, 2 H), 3.21 (dd, 1 H), 3.03 (dd, 1 H), 1.96-1.86 (m, 2 H), 1.85-1.74 (m, 4 H). |

TABLE 3-continued

| Compound No. | Structure | m/z | ¹H NMR |
|---|---|---|---|
| 1-19 | 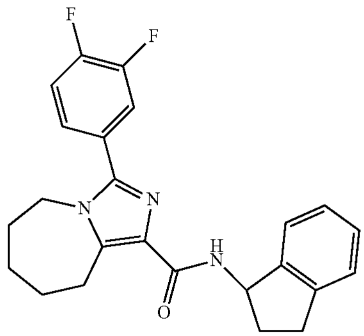 [SMILES: O=C(NC1CCc2ccccc21)c1nc(-c2ccc(F)c(F)c2)n2c1CCCCC2] | 408.2 [M + H]⁺ | (CDCl₃) δ 7.51 (bs, 1 H), 7.40-7.30 (m, 2 H), 7.30-7.17 (m, 5 H), 5.68 (dd, 1 H), 4.04 (m, 2 H), 3.48 (bs, 2 H), 3.04 (ddd, 1 H), 2.91 (ddd, 1 H), 2.70-2.60 (m, 1 H), 2.03-1.73 (m, 7 H). |
| 1-20 | 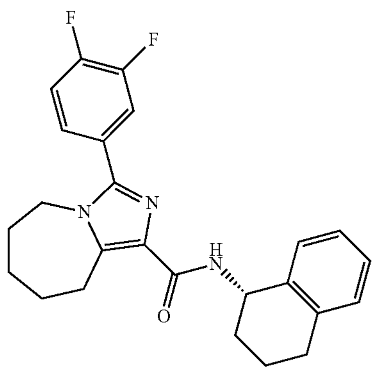 [SMILES: O=C(N[C@H]1CCCc2ccccc21)c1nc(-c2ccc(F)c(F)c2)n2c1CCCCC2] | 422.2 [M + H]⁺ | (CDCl₃) δ 7.53 (bs, 1 H), 7.39-7.30 (m, 2 H), 7.29-7.18 (m, 2 H), 7.18-7.08 (m, 3 H), 5.37 (m, 1 H), 4.03 (m, 2 H), 2.97 (bs, 2 H), 2.91-2.72 (, 2 H), 2.18-2.08 (m, 1 H), 2.00-1.75 (m, 9 H). |
| 1-21 | 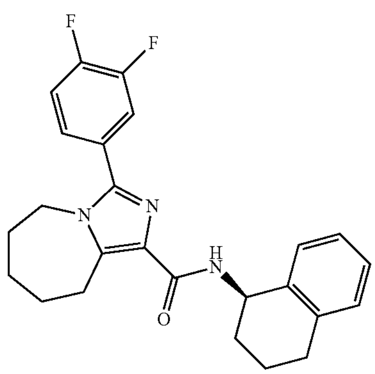 [SMILES: O=C(N[C@@H]1CCCc2ccccc21)c1nc(-c2ccc(F)c(F)c2)n2c1CCCCC2] | 422.2 [M + H]⁺ | (CDCl₃) δ 7.53 (bs, 1 H), 7.39-7.30 (m, 2 H), 7.29-7.18 (m, 2 H), 7.18-7.08 (m, 3 H), 5.37 (m, 1 H), 4.03 (m, 2 H), 2.97 (bs, 2 H), 2.91-2.72 (, 2 H), 2.18-2.08 (m, 1 H), 2.00-1.75 (m, 9 H). |
| 1-22 | 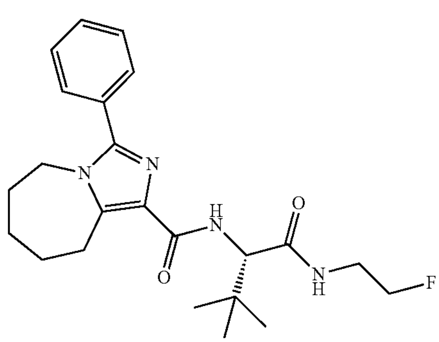 [SMILES: CC(C)(C)[C@H](NC(=O)c1nc(-c2ccccc2)n2c1CCCCC2)C(=O)NCCF] | 415.3 [M + H]⁺ | (CDCl₃) δ 7.69 (m, 1 H), 7.38-7.20 (m, 5 H), 6.08 (bs, 1 H), 4.32 (m, 1 H), 4.20 (m, 1 H), 4.14 (m, 1 H), 3.83 (bs, 2 H), 3.52-3.08 (m, 4 H), 1.72-1.62 (m, 2 H), 1.62-1.47 (m, 4 H), 0.89 (s, 9 H). |

TABLE 3-continued

| Compound No. | Structure | m/z | $^1$H NMR |
|---|---|---|---|
| 1-23 | 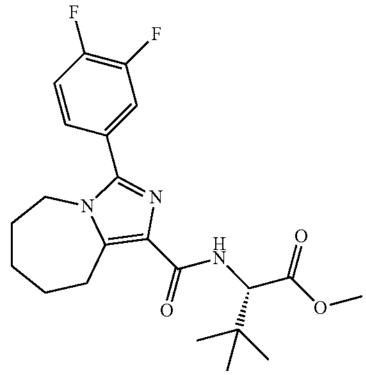 [SMILES: COC(=O)[C@@H](NC(=O)c1nc(-c2ccc(F)c(F)c2)n2c1CCCCC2)C(C)(C)C] | 420.3 [M + H]$^+$ | (CDCl$_3$) δ 7.69 (bd, 1 H), 7.34-7.29 (m, 1 H), 7.24-7.15 (m, 2 H), 4.52 (d, 1 H), 3.94 (m, 2 H), 3.65 (s, 3 H), 3.30 (bs, 2 H), 1.85-1.76 (m, 2 H), 1.75-1.61 (m, 4 H), 0.98 (s, 9 H). |
| 1-24 | 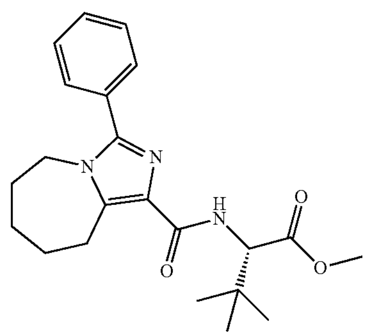 [SMILES: COC(=O)[C@@H](NC(=O)c1nc(-c2ccccc2)n2c1CCCCC2)C(C)(C)C] | 384.3 [M + H]$^+$ | (CDCl$_3$) δ 7.589 (bs, 1 H), 7.50-7.44 (m, 2 H), 7.44-7.35 (m, 3 H), 4.54 (d, 1 H), 3.96 (m, 2 H), 3.65 (s, 3 H), 3.32 (bs, 2 H), 1.84-1.75 (m, 2 H), 1.75-1.59 (m, 4 H), 0.99 (s, 9 H). |

Example 2

Preparation of 2-1: (S)-3-(3,4-difluorophenyl)-N-(3,3-dimethyl-1-(methylamino)-1-oxobutan-2-yl)-6,6,8-trimethyl-6,7,8,9-tetrahydro-5H-imidazo[1,5-a][1,4]diazepine-1-carboxamide

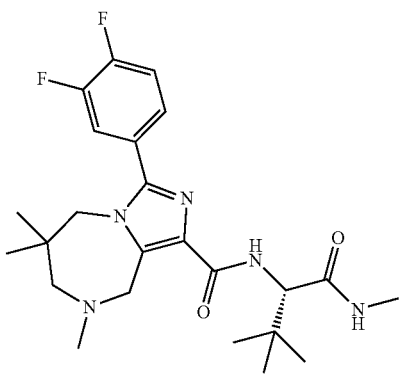

2-1

Step 1: Preparation of (S)-tert-butyl 3-(3,4-difluorophenyl)-1-(3,3-dimethyl-1-(methylamino)-1-oxobutan-2-ylcarbamoyl)-6,6-dimethyl-6,7-dihydro-5H-imidazo[1,5-a][1,4]diazepine-8(9H)-carboxylate Intermediate G3 (130 mg, 0.31 mmol) was dissolved with stirring in 3 mL of DMF and treated with DIEA (0.11 mL, 0.617 mmol) and the mixture stirred for 10 minutes. The solution was cooled in an ice-water bath and L-tert-leucine-N-methyl-amide (58 mg, 0.40 mmol) was added followed by TBTU (149 mg, 0.46 mmol) and stirring was continued for 1 hour. The ice bath was removed and the mixture stirred for an additional hour and then quenched by the addition of 10 mL water, followed by the addition of 10 mL EtOAc. The layers were separated and the aqueous phase was extracted with 10 mL EtOAc. The combined organic phases were washed with 10 mL each of saturated aqueous NaHCO$_3$, 1M aqueous HCl, water and brine, and then dried over Na$_2$SO$_4$, filtered and concentrated in vacuo. The residue was purified by column chromatography (ISCO RediSep-4, eluting with EtOAc) yielding 133 mg (79%) of the title compound as a waxy solid. LCMS (+ESI) m/z: 548.4 [MH]$^{+1}$, 392.3 [MH-56]$^{+1}$ $^1$H-NMR (DMSO d6) δ 7.89 (bs, 1H), 7.48-7.28 (m, 3H), 7.18-7.11 (m, 1H), 5.06-4.32 (bs, 2H), 4.09 (d, 1H), 3.75-3.55 (m, 2H), 3.25-2.96 (m, 2H), 2.35 (d, 3H), 1.08 (s, 9H), 0.69 (s, 9H), 0.50 (s, 3H), 0.45 (s, 3H).

Step 2: Preparation of (S)-3-(3,4-difluorophenyl)-N-(3,3-dimethyl-1-(methylamino)-1-oxobutan-2-yl)-6,6-dimethyl-6,7,8,9-tetrahydro-5H-imidazo[1,5-a][1,4]diazepine-1-carboxamide: The product from step 1 above (128 mg, 0.23 mmol) was dissolved in 2 mL of DCM and carefully treated with 2 mL of TFA. The mixture was stirred for 45 minutes and concentrated in vacuo. The residue was suspended in 5 mL of toluene and concentrated in vacuo. The residue was dried in a vacuum oven overnight to give the title compound (182 mg, 99%) as a poly-TFA salt. LCMS (+ESI) m/z: 448.3 [MH]$^{+1}$ Step 3: Preparation of (S)-3-(3,4-difluorophenyl)-N-(3,3-dimethyl-1-(methylamino)-1-oxobutan-2-yl)-6,6,8-trimethyl-6,7,8,9-tetrahydro-5H-imidazo[1,5-a][1,4]diazepine-1-carboxamide: The product from step 2 above (181 mg, 0.23 mmol) was dissolved in 2 mL of THF and treated sequentially with 37% aqueous formaldehyde (63 µL, 2.30 mmol) and potassium acetate (45 mg, 0.46 mmol) and the mixture stirred for 10 minutes. Sodium triacetoxyborohydride (146 mg, 0.69 mmol) was added and stirring continued for 1.5 hours. The reaction was quenced by the addition of 5 mL of saturated aqueous NaHCO$_3$ and 10 mL of DCM was added. The layers were separated and the aqueous layer was extracted with 10 mL of DCM. The combined organic phases were dried over Na$_2$SO$_4$, filtered and concentrated in vacuo. The residue was purified by column chromatography (ISCO RediSep-4, gradient elution 0%-20% EtOH:acetonitrile). The residue was lyophilized from aqueous acetonitrile to give 85 mg (9% yield) of (S)-3-(3,4-difluorophenyl)-N-(3,3-dimethyl-1-(methylamino)-1-oxobutan-2-yl)-6,6,8-trimethyl-6,7,8,9-tetrahydro-5H-imidazo[1,5-a][1,4]diazepine-1-carboxamide as a white powder. LCMS (+ESI) m/z: 462.3 [MH]$^{+1}$. $^1$H-NMR (DMSO d6) δ 8.07 (m, 1H), 7.64-7.48 (m, 3H), 7.35-7.28 (m, 1H), 5.06-4.32 (bs, 2H), 4.24 (d, 1H), 3.91-3.66 (m, 2H), 2.52 (d, 3H), 2.40-2.32 (m, 2H), 2.27 (s, 3H), 1.08 (s, 9H), 0.85 (s, 9H), 0.66 (s, 3H), 0.59 (s, 3H).

The compounds listed in Table 4 were prepared using the procedure described for the synthesis of compound 2-1.

These compounds were prepared by treating the appropriate intermediate described above with the appropriate amine. For example, compound 2-2 ((S)-3-(3,4-difluorophenyl)-N-(3,3-dimethyl-1-(methylamino)-1-oxobutan-2-yl)-6,7,8,9-tetrahydro-5H-imidazo[1,5-a]azepine-1-carboxamide) was prepared reacting intermediate G1 with (S)-2-amino-N,3,3-trimethylbutanamide.

Compound 2-3 is (S)-3-(3,4-difluorophenyl)-N-(3,3-dimethyl-1-(methylamino)-1-oxobutan-2-yl)-8-ethyl-6-methyl-6,7,8,9-tetrahydro-5H-imidazo[1,5-a][1,4]diazepine-1-carboxamide.

Compounds 2-4 and 2-5 are each (S)-3-(3,4-difluorophenyl)-N-(3,3-dimethyl-1-(methylamino)-1-oxobutan-2-yl)-7,8-dimethyl-6,7,8,9-tetrahydro-5H-imidazo[1,5-a][1,4]diazepine-1-carboxamide.

TABLE 4

| Compound # | Structure | m/z | $^1$H NMR |
|---|---|---|---|
| 2-2 Mixture of 2 diastereomers | 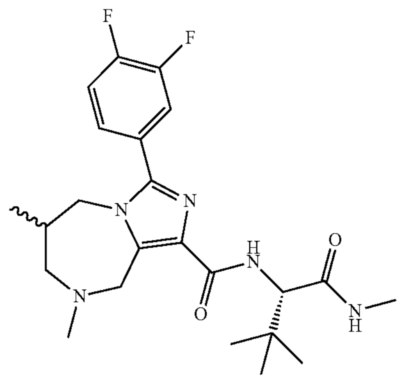 | 448.3 [M + H]$^+$ | (DMSO d6) δ 8.06 (m, 1 H), 7.68-7.48 (m, 3 H), 7.37-7.30 (m, 1 H), 4.24 (m, 1 H), 3.98-3.76 (m, 3 H), 2.74 (m, 1 H), 2.61-2.50 (m, 4 H), 2.17 (d, 3 H), 2.00 (m, 1 H), 0.85 (s, 4.5 H), 0.84 (s, 4.5 H), 0.72 (s, 1.5 H), 0.70 (s, 1.5 H), 0.69 (s, 1.5 H), 0.67 (s, 1.5 H). |
| 2-3 Mixture of 2 diastereomers | 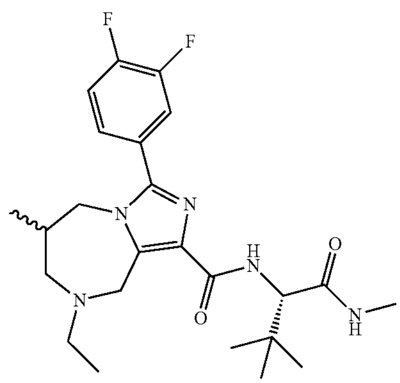 | 462.3 [M + H]$^+$ | (DMSO d6) δ 8.07 (m, 1 H), 7.69-7.48 (m, 3 H), 7.38-7.28 (m, 1 H), 4.26 (m, 1 H), 3.99-3.72 (m, 3 H), 2.96-2.78 (m, 1 H), 2.70-2.56 (m, 3 H), 2.56-2.50 (m, 3 H), 2.38-2.27 (m, 2 H), 2.00 (m, 1 H), 0.98-.090 (m, 3 H), 0.85 (s, 4.5 H), 0.84 (s, 4.5 H), 0.73 (s, 1.5 H), 0.71 (s, 1.5 H), 0.70 (s, 1.5 H), 0.68 (s, 1.5 H). |
| 2-4 Faster eluting diastereoisomer | 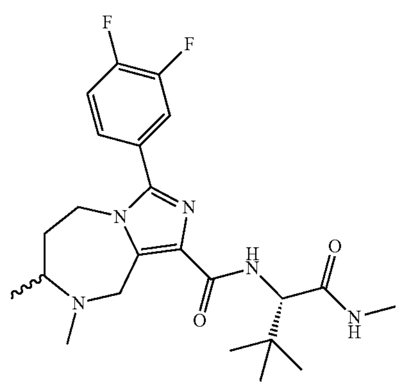 | 448.3 [M + H]$^+$ | (CDCl$_3$) δ 7.74 (d, 1 H), 7.35-7.27 (m, 1 H), 7.24-7.11 (m, 2 H), 5.70 (m, 1 H), 5.01-4.65 (m, 1 H), 4.25-4.14 (m, 2 H), 4.11-3.85 (m, 2 H), 2.72 (d, 3 H), 2.23 (bs, 3 H), 1.82-1.60 (m, 2 H), 1.18 (m, 3 H), 0.99 (s, 9 H) |

TABLE 4-continued
| Compound # | Structure | m/z | 1H NMR |
|---|---|---|---|
| 2-5 Slower eluting diastereoisomer | 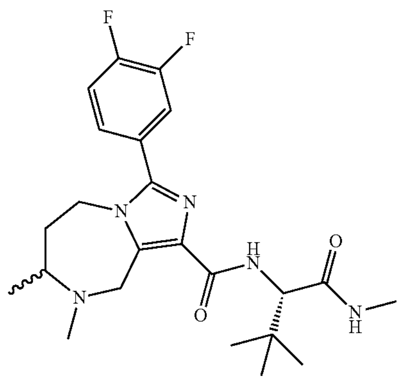 | 448.3 [M + H]+ | (CDCl3) δ 7.79 (d, 1 H), 7.35-7.27 (m, 1 H), 7.21-7.15 (m, 2 H), 5.72 (m, 1 H), 5.01-4.79 (m, 1 H), 4.21 (d, 1 H), 4.20-4.14 (m, 1 H), 4.04-3.84 (m, 2 H), 2.73 (d, 3 H), 2.17 (bs, 3 H), 1.74-1.56 (m, 2 H), 1.13 (d, 3 H), 0.98 (s, 9 H) |
Example 3
6,7,8,9-tetrahydro-5H-imidazo[1,5-d][1,4]diazepines
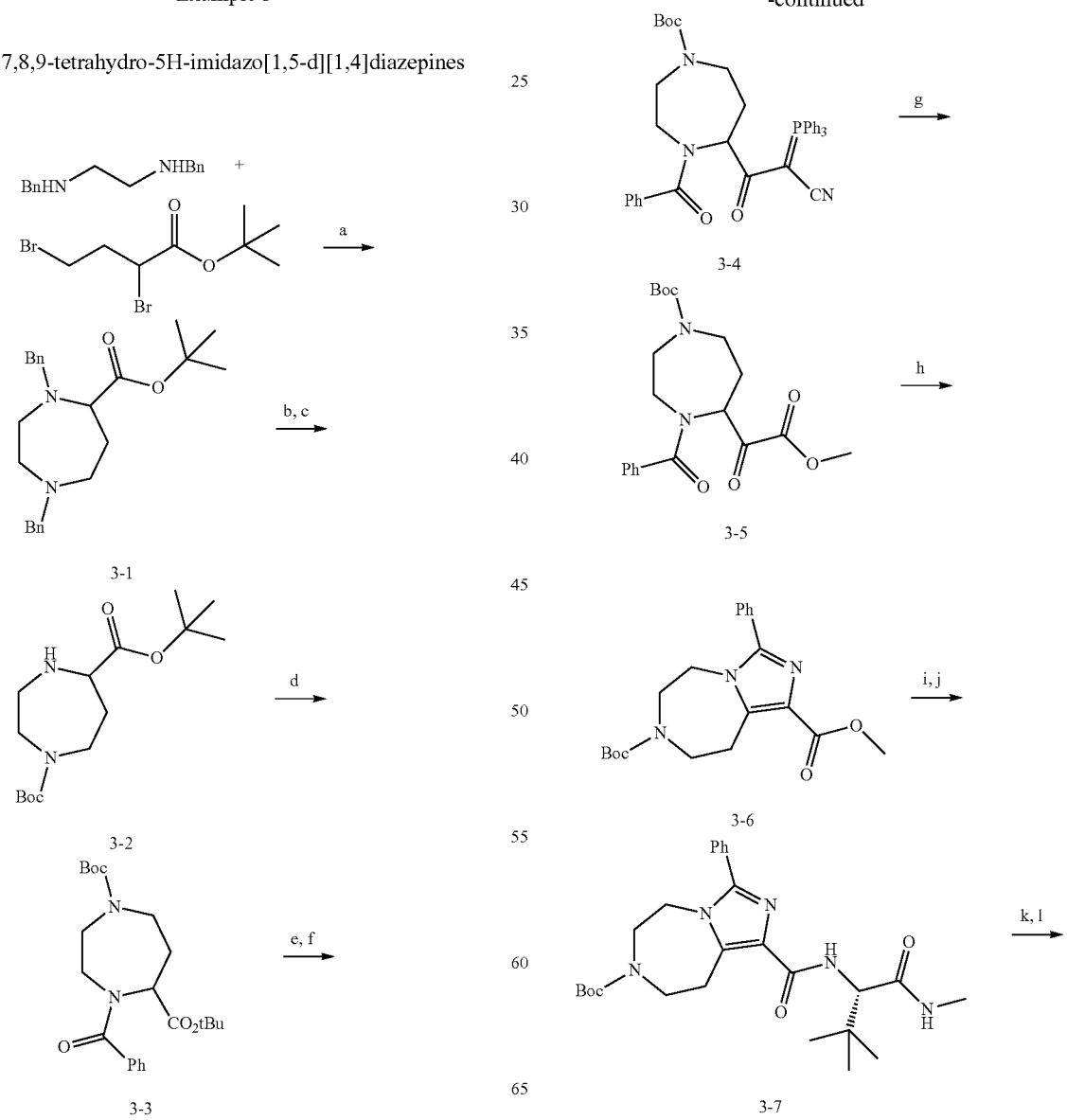

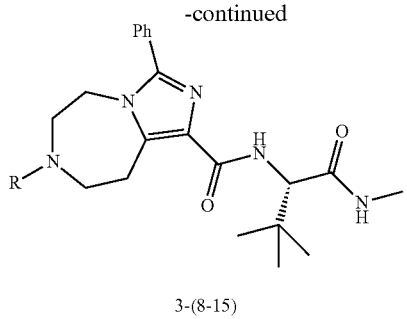

3-(8-15)

a) TEA, DCM; b) H$_2$, Pd/C, EtOH; c) Boc$_2$O, NaOH, dioxane/water; d) PhCOCl, TEA, DCM; e) LiOH, MeOH; f) Ph$_3$P=CHCN, EDCI, DMAP, DCM; g) dimethyl dioxirane, DCM, MeOH; h) NH$_3$, AcOH; i) LiOH, MeOH; j) L-tert-Leucine methylamide, TBTU, DIEA, DMF; k) TFA, DCM; l) RCHO, AcOH, Na(OAc)$_3$BH or RCOCl, TEA; or RSO$_2$Cl, TEA.

Preparation of (S)-tert-butyl 1-(3,3-dimethyl-1-(methylamino)-1-oxobutan-2-ylcarbamoyl)-3-phenyl-8,9-dihydro-5H-imidazo[1,5-d][1,4]diazepine-7(6H)-carboxylate (Compound 3-7)

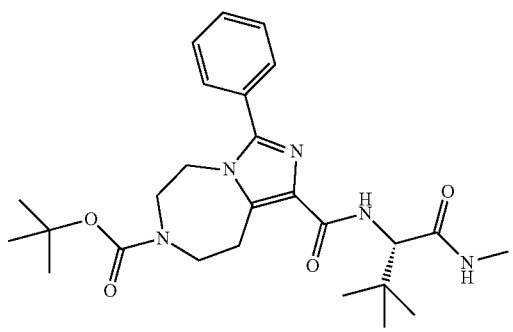

3-7

Step 1: Preparation of tert-butyl 1,4-dibenzyl-1,4-diazepane-5-carboxylate (Intermediate 3-1): To a 125 ml high pressure vessel was added dibenzylethylenediamine (3.72 g), tert-butyl 2,4-dibromobutanoate (5.03 g) and triethyl amine (4.60 g). DCM (20 ml) was added and heated at 60° C. overnight. The mixture was then diluted with DCM and extracted with saturated sodium bicarbonate. Crude product was purified by column chromatography (ISCO RediSep 12, gradient elution with 10-35% EtOAc/Hexanes) to give 3.42 g pure Intermediate 3-1 (60% yield as an oil).

Step 2: Preparation of di-tert-butyl 1,4-diazepane-1,5-dicarboxylate (Intermediate 3-2): A solution of Intermediate 3-1 (5.42 g) in EtOH (50 mL) was hydrogenated with palladium on carbon (1.42 g) under hydrogen (65 psi) for 5 h. After filtration to remove palladium catalyst, EtOH was evaporated. The crude intermediate (2.80 g) was dissolved in 1,4-dioxane, to which Boc$_2$O (3.10 g) and aqueous 1N NaOH (15 mL) was added. After stirring at room temperature for 1 hour, the mixture was diluted with diethyl ether and extracted with saturated sodium bicarbonate. The organic phase was dried over sodium sulfate and evaporated to give Intermediate 3-2 (4.21 g, 99% yield).

Step 3: Preparation of di-tert-butyl 4-benzoyl-1,4-diazepane-1,5-dicarboxylate (Intermediate 3-3): To a solution of Intermediate 3-2 (4.21 g) and TEA (2.0 g) in DCM (50 mL) was added benzoyl chloride (2.11 g) slowly. After stirring at room temperature for 1 hour and then the reaction was quenched with saturated sodium bicarbonate. The organic phase was dried over sodium sulfate and evaporated to dryness. Purification was achieved by chromatography on an ISCO column (RediSep 12, gradient elution with 10% to 70% EtOAc/Hex providing pure Intermediate 3-3 (2.82 g, 49% yield for the three steps).

Step 4: Preparation of 2-(4-benzoyl-1-(tert-butoxycarbonyl)-1,4-diazepan-5-yl)-1-cyano-2-oxoethanetriphenylphosphene (Intermediate 3-4): A solution of Intermediate 3-3 (2.82 g) and lithium hydroxide (1.68 g) in MeOH was heated at 65° C. for 2 hours. After evaporation of the MeOH, the residue was twice extracted with water (pH 2) and DCM. The combined organic phases were dried over sodium sulfate and evaporated to dryness to give the carboxylic acid intermediate (2.40 g, 99%). The carboxylic acid (2.40 g), triphenylphosphranyldine acetontirile and DMAP were dissolved in DCM (40 ml) at room temperature. EDCI was added in portions and stirred at room temperature overnight. The reaction was quenched with saturated sodium bicarbonate. The organic phase was separated and dried over sodium sulfate and the product was purified by column chromatography on an ISCO column (RediSep 12, gradient elution with 50-100% EtOAc/Hex) to give Intermediate 3-4 (3.50 g, 80% yield).

Step 5: Preparation of tert-butyl 4-benzoyl-5-(2-methoxy-2-oxoacetyl)-1,4-diazepane-1-carboxylate (Intermediate 3-5): To a solution of Intermediate 3-4 (1.26 g) in DCM and MeOH was added a solution of dimethyl dioxirane in acetone (30 mL), which is prepared freshly from Oxone (100 g). After stirring at room temperature for 1 hour, the reaction mixture was evaporated under reduced pressure. The residue was extracted between EtOAc and saturated sodium bicarbonate. The organic phase was dried over sodium sulfate and evaporated to dryness to give Intermediate 3-5 which was used in the next step without further purification.

Step 6: Preparation of 7-tert-butyl 1-methyl 3-phenyl-8,9-dihydro-5H-imidazo[1,5-d][1,4]diazepine-1,7(6H)-dicarboxylate (Intermediate 3-6): The product of the last step was dissolved in AcOH (30 mL) and 7N ammonia in MeOH (4.0 mL). The mixture was heated to reflux for 30 min and then evaporated to dryness. The residue was extracted between EtOAc and saturated sodium bicarbonate. The organic phase was then dried over sodium sulfate and evaporated to dryness. The residue was purified by HPLC chromatography on an ISCO column (RediSep 12, gradient elution with 50-80% EtOAc/hexanes) to give Intermediate 3-6 (0.20 g, 27% for two steps).

Step 7: Preparation of (S)-tert-butyl 1-(3,3-dimethyl-1-(methylamino)-1-oxobutan-2-ylcarbamoyl)-3-phenyl-8,9-dihydro-5H-imidazo[1,5-d][1,4]diazepine-7(6H)-carboxylate (Compound 3-7): A solution of Intermediate 3-6 (0.20 g) and lithium hydroxide (0.13 g) in MeOH was heated at 65° C. for 2 hours. After evaporation of MeOH, the residue was extracted with water (pH 2) and ethyl acetate twice. The combined organic phase was dried over sodium sulfate and evaporated to dryness to give a carboxylic acid intermediate (167 mg, 87%). To a solution of this intermediate (167 mg), DIEA (0.3 mL) and L-tert-Leucine methyl amide (101 mg) in DMF (5 mL) was added TBTU (179 mg). After stirring at room temperature overnight, DMF was evaporated under vacuum. The reaction was extracted between saturated sodium bicarbonate and ethyl acetate. The organic phase was then dried over sodium sulfate and evaporated to dryness. Purification was achieved by chromatography (ISCO RediSep 12 column), eluting with a gradient of 70-100% EtOAc/hexanes to give compound 3-7 (156 mg, 67%). Calculated MW 483.6: Observed LCMS m/z: 484.2.

The preparation of 6,7,8,9-tetrahydro-5H-imidazo[1,5-d][1,4]diazepine compounds 3-8 to 3-15 are described in the following paragraphs. The structure and the observed molecular ion mass for each of these compounds is shown in Table 5 below.

TABLE 5

| Compound No. | Structure | m/z | Name |
|---|---|---|---|
| 3-8 | 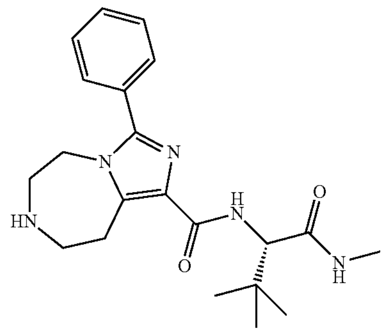 [SMILES: CNC(=O)[C@@H](NC(=O)c1nc(-c2ccccc2)n2c1CCNCC2)C(C)(C)C] | 384.1 [M + H]+ | (S)-N-(3,3-dimethyl-1-(methylamino)-1-oxobutan-2-yl)-3-phenyl-6,7,8,9-tetrahydro-5H-imidazo[1,5-d][1,4]diazepine-1-carboxamide |
| 3-9 | 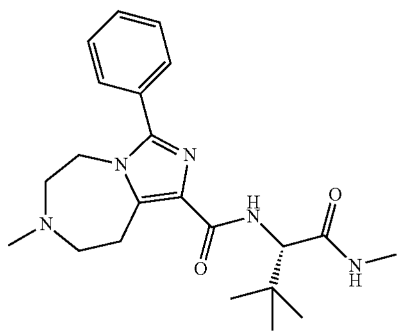 | 398.2 [M + H]+ | (S)-N-(3,3-dimethyl-1-(methylamino)-1-oxobutan-2-yl)-7-methyl-3-phenyl-6,7,8,9-tetrahydro-5H-imidazo[1,5-d][1,4]diazepine-1-carboxamide |
| 3-10 | 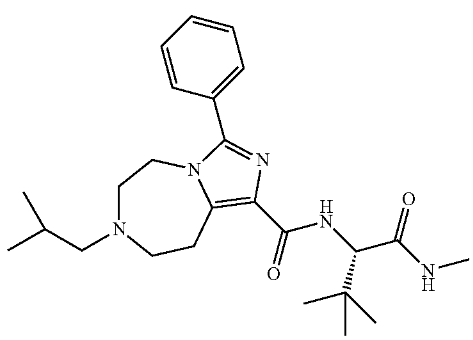 [SMILES: CNC(=O)[C@@H](NC(=O)c1nc(-c2ccccc2)n2c1CCN(CC(C)C)CC2)C(C)(C)C] | 440.2 [M + H]+ | (S)-N-(3,3-dimethyl-1-(methylamino)-1-oxobutan-2-yl)-7-isobutyl-3-phenyl-6,7,8,9-tetrahydro-5H-imidazo[1,5-d][1,4]diazepine-1-carboxamide |
| 3-11 | 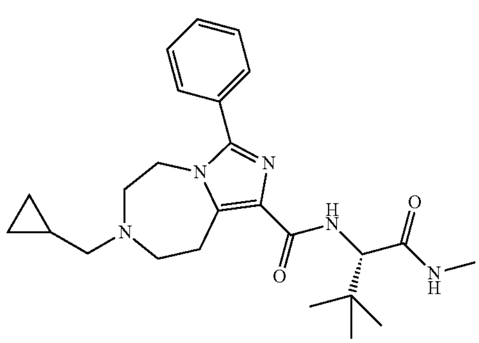 [SMILES: CNC(=O)[C@@H](NC(=O)c1nc(-c2ccccc2)n2c1CCN(CC1CC1)CC2)C(C)(C)C] | 438.2 [M + H]+ | (S)-7-(cyclopropylmethyl)-N-(3,3-dimethyl-1-(methylamino)-1-oxobutan-2-yl)-3-phenyl-6,7,8,9-tetrahydro-5H-imidazo[1,5-d][1,4]diazepine-1-carboxamide |

TABLE 5-continued

| Compound No. | Structure | m/z | Name |
|---|---|---|---|
| 3-12 | 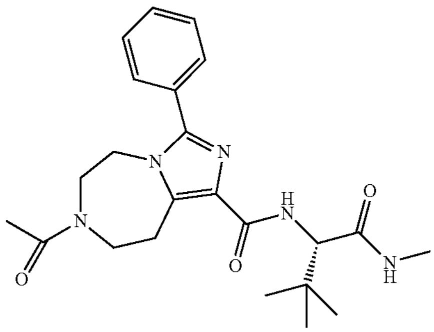 [SMILES: CNC(=O)[C@@H](NC(=O)c1nc(-c2ccccc2)n2c1CCN(C(C)=O)CC2)C(C)(C)C] | 426.2 [M + H]⁺ | (S)-7-acetyl-N-(3,3-dimethyl-1-(methylamino)-1-oxobutan-2-yl)-3-phenyl-6,7,8,9-tetrahydro-5H-imidazo[1,5-d][1,4]diazepine-1-carboxamide |
| 3-13 | 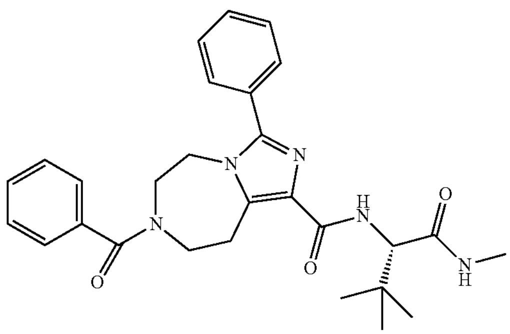 | 448.2 [M + H]⁺ | (S)-7-benzoyl-N-(3,3-dimethyl-1-(methylamino)-1-oxobutan-2-yl)-3-phenyl-6,7,8,9-tetrahydro-5H-imidazo[1,5-d][1,4]diazepine-1-carboxamide |
| 3-14 | 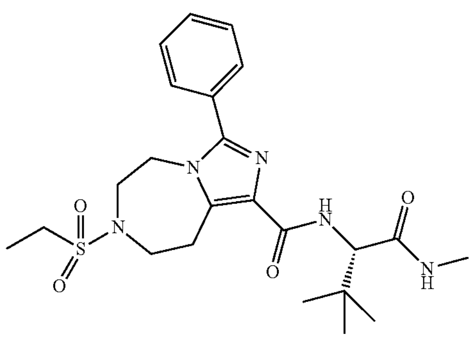 [SMILES: CCS(=O)(=O)N1CCc2c(C(=O)N[C@H](C(=O)NC)C(C)(C)C)nc(-c3ccccc3)n2CC1] | 476.2 [M + H]⁺ | (S)-N-(3,3-dimethyl-1-(methylamino)-1-oxobutan-2-yl)-7-(ethylsulfonyl)-3-phenyl-6,7,8,9-tetrahydro-5H-imidazo[1,5-d][1,4]diazepine-1-carboxamide |
| 3-15 | 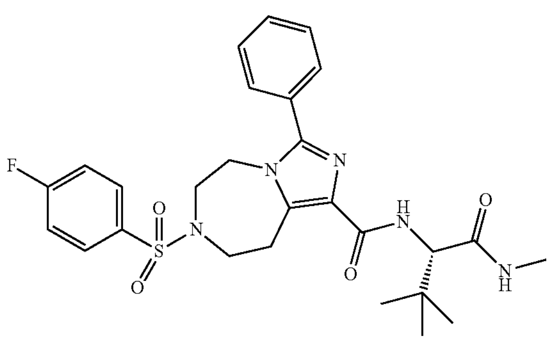 [SMILES: CNC(=O)[C@@H](NC(=O)c1nc(-c2ccccc2)n2c1CCN(S(=O)(=O)c1ccc(F)cc1)CC2)C(C)(C)C] | 542.2 [M + H]⁺ | (S)-N-(3,3-dimethyl-1-(methylamino)-1-oxobutan-2-yl)-7-(4-fluorophenylsulfonyl)-3-phenyl-6,7,8,9-tetrahydro-5H-imidazo[1,5-d][1,4]diazepine-1-carboxamide |

Preparation of Compound 3-8

A solution of compound 3-7 (156 mg) in DCM and TFA was stirred at room temperature for 30 min. After evaporation of solvents, the residue was extracted between saturated sodium bicarbonate and DCM. The organic phase was then dried over sodium sulfate and evaporated to dryness to give compound 3-8 (120 mg, 92%).

Preparation of Compound 3-9

To a solution of compound 3-8 (5 mg), paraformaldehyde (30%, 15 uL) and acetic acid (2 uL) in THF was added sodium triacetoxyborohydride (6 mg). After stirring at room temperature for 2 hours, the THF was removed by evaporation. The residue was extracted between saturated sodium bicarbonate and EtOAc. The organic phase was then dried over sodium sulfate and evaporated to give compound 3-9 (7 mg).

Preparation of Compound 3-10

Compound 3-10 was prepared following the procedure for the synthesis of compound 3-9 replacing formaldehyde with isobutyraldehyde.

Preparation of Compound 3-11

Compound 3-11 was prepared following the procedure described above for the synthesis of compound 3-9, except that formaldehyde was replaced with cyclopropyl carboxaldehyde.

Preparation of (Compound 3-12)

To a solution of compound 3-8 (5 mg) and TEA (5 μL) in DCM was added acetylchloride (3 uL). After stirring at room temperature for 1 hour, the reaction was quenched with aqueous sodium bicarbonate. The organic phase was separated and dried over sodium sulfate. Evaporation under mild vacuum gave compound 3-12 (5 mg).

Preparation of Compound 3-13

Compound 3-13 was prepared following the above-described procedure for the synthesis of compound 3-12 except that acetylchloride was replaced with benzoyl chloride.

Preparation of Compound 3-14

Compound 3-14 was prepared following the above-described procedure for the synthesis of compound 3-12 except that acetylchloride was replaced with ethanesulfonyl chloride.

Preparation Compound 3-15

Compound 3-15 was prepared following the procedure for the synthesis of compound 3-12 replacing acetylchloride with 4-fluorophenylsulfonyl chloride.

Example 4

Preparation of 2-(3-(3,4-difluorophenyl)-6,7,8,9-tetrahydro-5H-imidazo[1,5-a]azepin-1-yl)-5-methyl-1,3,4-oxadiazole (Compound 4-1)

To a solution of 3-(3,4-difluorophenyl)-6,7,8,9-tetrahydro-5H-imidazo[1,5-a]azepine-1-carboxylic acid (100 mg, 0.342 mmol) in DCM (5 mL) was added acetylhydrazide (26.6 mg, 0.359 mmol), and N-ethyl-N-isopropylpropan-2-amine (133 mg, 1.026 mmol). TBTU (115 mg, 0.359 mmol) was added and the reaction was stirred for 3 hours.

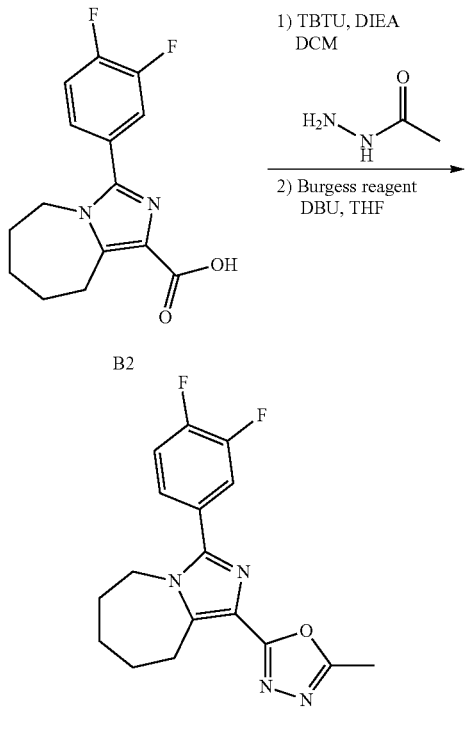

LCMS analysis showed that the reaction was complete. The solution was extracted with saturated sodium hydrogen carbonate (2 mL) and the organic layer was removed. The aqueous layer was extracted with DCM (5 mL). The combined organic extracts were dried over anhydrous sodium sulfate, filtered and evaporated under reduced pressure. The residue was dissolved in THF (2 mL) and placed in a 2 mL microwave vial. Methyl N-(triethylammoniumsulphonyl) carbamate (Burgess reagent) (244 mg, 1.026 mmol) and DBU (5.16 μl, 0.034 mmol) were added. The reaction was heated to 160° C. for 10 minutes. The solution was then extracted with saturated sodium hydrogen carbonate (2 mL) and the organic layer removed. The aqueous layer was extracted with 2 mL EtOAc (2 ml) and the combined organic extracts were dried over anhydrous sodium sulfate, filtered and evaporated under reduced pressure. The residue was purified by preparative LC/MS. The appropriate fractions were combined and dried to yield (19 mg, 17%) of 2-(3-(3,4-difluorophenyl)-6,7,8,9-tetrahydro-5H-imidazo[1,5-a]azepin-1-yl)-5-methyl-1,3,4-oxadiazole as an orange solid. LCMS (+ESI) m/z: 331.2 [M+H]$^+$. $^1$H-NMR (CDCl$_3$) δ 7.33 (ddd, 1H), 7.24-7.16 (m, 2H), 4.02 (m, 2H), 3.31 (bs, 2H), 2.52 (s, 3H), 1.91-1.81 (m, 2H), 1.80-1.68 (m, 4H).

Example 5

Screening Methods

The ability of compounds to act as agonists or inverse agonists at human CB2 and CB1 receptors (hCB2, hCB1, respectively) and at the rat CB2 receptor (rCB2) was determined by measuring changes in intracellular cAMP levels. Chinese Hamster Ovary (CHO-K1) cell lines stably expressing hCB2 (Genebank: X74328) or hCB1 (Genebank: X54937) were purchased from Euroscreen (Gosselies, Belgium). The rat CB2 receptor was expressed from genomic DNA (provided by M. Abood, California Pacific Medical Center) in CHO-K1 cells from expression plasmid vector, pcDNA3.1.

Cell lines were grown in suspension in EX-CELL 302 CHO Serum-free medium (Sigma, cat #14324C) supplemented with 1% Fetal Bovine Serum, glutamine and non-essential amino-acids under 0.4 mg/mL G418 selection.

Receptor mediated responses were determined by measuring changes in intracellular cAMP using LANCE cAMP detection kit (cat #AD0264, Perkin Elmer, Wellesley, Mass.) based on time-resolved fluorescence resonance energy transfer (TR-FRET). Changes in cAMP were determined in cells pre-incubated with IBMX (isobutyl methylxanthine) and pre-stimulated with NKH-477 (a water soluble forskolin derivative, cat #1603, Tocris, Ellisville, Mo.) to increase basal cAMP levels as detailed below.

On the day of the experiment, cells were spun at low speed for 5 min at room temperature. The supernatant was removed and cells were resuspended in stimulation buffer (Hanks Buffered Salt Solution/5 mM HEPES, containing 0.5 mM IBMX (cat #17018, Sigma) and 0.02% BSA (Perkin-Elmer, cat #CR84-100)). Cell clumps were removed by filtering through cell strainer 40 μm (BD Falcon, Discovery Labware, Bedford, Mass.) and diluted to $2 \times 10^5$ cells/mL. Antibody supplied with the LANCE cAMP immunoassay kit was then added according to the manufacturer's instructions. An aliquot of cells was taken for un-induced controls. To the remaining cells was added NKH-477 (a water soluble forskolin derivative, Tocris cat #1603) to a final concentration of 2-8 μM. Cells were then incubated for 30 min at room temperature prior to adding to Proxiplates containing test compounds (final DMSO concentration was less than 0.5%) with a Multidrop bulk dispenser, followed by a sixty minute incubation at room temperature. The response was stopped by addition of the detection mix supplied with the LANCE kit. The reagents were allowed to equilibrate for three hours prior to reading on an Envision multi-mode detector (Perkin-Elmer). TR-FRET was measured using a 330-380 nm excitation filter, a 665 nm emission filter, dichroic mirror 380 nm and Z=1 mm. Cyclic AMP concentrations in each well were back-calculated from a cAMP standard curve run concurrently during each assay. Each plate contained 16 wells of forskolin stimulated cells and 16 wells of forskolin plus CP55,940-treated cells. Cells were treated with 1 μM CP55,940 (Tocris cat. #0949). Concentrations of cAMP were expressed as a percent of the difference of these two groups of wells. Concentration-response data including $EC_{50}$ (the concentration of compound producing 50% of the maximal response) and intrinsic activity (the percent maximal activation compared to full activation by CP55,940) were determined using a four-parameter non-linear regression algorithm (Xlfit equation 251, IDBS). Results are shown in Table 6, below.

All the compounds tested, except 3-9, 3-11, 3-12, 3-13 and 4-1, were agonists with an $EC_{50}$ of <10 μM at the hCB1 receptors or the hCB2 receptor, or both. Compounds 3-9, 3-11, 3-12, 3-14 and 4-1 exhibited $EC_{50}$ values above 10 μM in both the human CB1 and human CB2 receptor binding assays.

TABLE 6

| CB | $EC_{50}$ | COMPOUND NUMBER. |
|---|---|---|
| hCB2 | 0.1 nM-10 nM | 1-1, 1-2, 1-3, 1-4, 1-5, 1-6, 1-7, 1-9, 1-12, 1-13, 1-14, 1-15, 1-18, 1-19, 1-20, 1-21, 1-22, 1-23, 1-24, 2-2 |
| | >10 nM-100 nM | 1-8, 1-10, 1-11, 1-16, 1-17, 2-1, 2-3, 2-4, 2-5 |
| | >100 nM-100 μM | 3-8, 3-13, 3-15 |
| hCB1 | 0.1 nM-10 nM | 1-2, 1-3, 1-5, 1-7, 1-12, 1-13, 1-14, 1-23, 1-24 |
| | >10 nM-100 nM | 1-1, 1-4, 1-9, 1-10, 1-16, 1-17, 1-18, 1-22, 2-2, 2-3 |
| | >100 nM-100 μM | 1-6, 1-8, 1-11, 1-15, 1-19, 1-20, 1-21, 2-1, 2-4, 2-5, 3-10, 3-13, 3-15 |

Compounds 3-11 and 3-15 exhibited $EC_{50}$ values for the rat CB2 receptor in the range 0.1-10 nM, whereas compounds 3-8, 3-10 and 3-14 each exhibited rat CB2 receptor $EC_{50}$ values in the range 10-100 nM.

$EC_{50}$ values at the rat CB2 receptor for compounds 3-9, 3-12 and 4-1 were above the detectable range (i.e. >10 μM) in this assay.

Example 6

Anti-Hyperalgesia in an Inflammatory Pain Model

The anti-hyperalgesic effects of test compounds in the Complete Freund's Adjuvant (CFA) model of inflammatory pain can be examined as described below. Male Sprague-Dawley rats (Hsd:Sprague-Dawley®™SD®™, Harlan, Indianapolis, Ind.) weighing about 200 grams, are housed three per cage. Animals have free access to food and water and are maintained on a 12 hour light/dark schedule for the entire duration of the experiment. Approximately 12 hours prior to behavioral testing, animals are placed on wire mesh bottom cages with free access to water but no access to food. Test compounds are prepared in 50% PEG-400 (Sigma-Aldrich, cat. P3265). Indomethacin (Fluka, cat 57413) is suspended in 0.5% methylcellulose (Sigma-Aldrich, cat. 274429). Groups of eight animals are anesthetized with 2-3% isoflurane and local inflammation induced by either 50 μl or 100 CFA (Sigma-Aldrich, cat F5881, *Mycobacterium tuberculosis* 1 mg/ml) injected subcutaneously into the plantar surface of the left paw.

Assessment of mechanical hyperalgesia: Baseline and post-treatment withdrawal thresholds to a noxious mechanical stimulus is measured using the Randall-Selitto paw pressure apparatus (Ugo Basile Analgesymeter, model 7200). This apparatus generates a linearly increasing mechanical force. The stimulus is applied to the plantar surface of the hind paws by a dome-shaped plastic tip placed between the third and fourth metatarsus. To avoid tissue damage, a cut-off pressure was set at 390 grams. Mechanical thresholds are defined as the force in grams at the first pain behavior, which includes paw withdrawal, struggle, and/or vocalization. Indomethacin (30 mg/kg, p.o.) can be used as the positive control. Mechanical hyperalgesia is measured using the Randall-Selitto paw pressure device before CFA injection and after intraperitoneal (i.p.) compound administration over a 24-hour period. The mean and standard error of the mean (SEM) are determined for the injured and normal paws for each treatment group.

Example 7

Inhibition of Acetic Acid-Induced Writhing in Mice

This test identifies compounds which exhibit analgesic activity against visceral pain or pain associated with activation of low pH-sensitive nociceptors [see Barber and Gottschlich (1986) Med. Res. Rev. 12: 525-562; Ramabadran and Bansinath (1986) Pharm. Res. 3: 263-270]. Intraperitoneal administration of dilute acetic acid solution causes a writhing behavior in mice. A writhe is defined as a contraction of the abdominal muscles accompanied by an extension of the forelimbs and elongation of the body. The number of writhes observed in the presence and absence of test compounds is counted to determine the analgesic activity of the compounds.

Male ICR mice, 20-40 grams in weight, were weighed and placed in individual observation chambers (usually a 4000 ml beaker) with a fine layer of rodent bedding at the bottom. To determine the activity and potency of test compounds, different doses of the compound solution or vehicle were injected subcutaneously in the back of the neck 30 minutes prior to administration of acetic acid solution. After administration of the compound or vehicle control, mice were returned to their individual observation chambers awaiting the intraperitoneal administration of acetic acid solution. Thirty minutes later, 10 ml/kg of a 0.6% (v/v) acetic acid solution was then injected into the right lower quadrant of the abdomen. Immediately after the injection, the mouse was returned to its observation chamber and the recording of the number of writhes is begun immediately. The number of writhes was counted over a 15-min period starting from the time of acetic acid injection. Raw data were analyzed using a one-way ANOVA followed by Dunnett's post-tests.

For dose-response analysis, raw data were converted to % maximum possible effect (% MPE) using the formula: % MPE=((Wc−Wv)/(0−Wv))×100, where Wc is the number of writhes in compound-treated mice and Wv is the mean number of writhes in vehicle-treated mice. The dose which elicited 50% attenuation of hypersensitivity (ED50) was determined using linear regression analysis. (Tallarida & Murray, 1987).

The MPEs determined in the above-described model for each of the compounds 1-1, 1-2, 1-3 and 1-9, when administered at a dose of 10 mg/kg were all greater than fifty percent.

Example 8

CFA Model of Acute Inflammation

The anti-hyperalgesic effects of test compounds in the Complete Freund's Adjuvant (CFA) model of inflammatory pain were examined as described below. Male Sprague-Dawley rats (Hsd:Sprague-Dawley®™SD®™, Harlan, Indianapolis, Ind.) weighing about 200 grams, were housed three per cage. Test compound and ibuprofen (Sigma, cat 11892) were each prepared in a mixture of 1:1:18 ethanol:cremophor EL:water. Groups of six animals were subjected to local inflammation induced by 0.1 mL CFA (Sigma-Aldrich, cat F5881, *Mycobacterium tuberculosis* 1 mg/ml) injected subcutaneously into the plantar surface of the left paw.

Assessment of thermal hyperalgesia: Paw withdrawal latencies (PWLs) in response to a noxious thermal stimulus (Model #37370, Ugo Basile, Cat #55370) were obtained before and 24 hours after intraplantar administration of CFA. Rats were placed in plexi-glass chambers (10×21×14 cm) on top of a glass platform (un-heated) and allowed to acclimate for approximately 15 min before testing. Each rat received 3 trials separated by approx. 3 min each and these scores were averaged to provide the final PWL. The mean and standard error of the mean (SEM) were determined for the injured paw in each treatment group. Significant reductions in PWLs (i.e., increased sensitivity to a noxious stimulus) were interpreted as the presence of thermal hyperalgesia. To avoid tissue damage, a cut-off latency of 20 seconds was employed. These behavioral assessments were carried-out under blinded conditions (i.e., compound preparation and animal dosing was performed by someone other than the person carrying out the behavioral assessments). Ibuprofen (100 mg/kg, p.o.) was used as the positive control. The mean and SEM were determined for the injured and normal paws for each treatment group. CFA produces a significant increase in sensitivity to noxious thermal stimuli as PWLs decreased from a pre-CFA baseline of 10.3±0.3 sec to a value of 4.3±0.2 sec (p≤0.05, paired t-test). Compound 1-10 produced a significant reversal of CFA-induced thermal hyperalgesia following oral (p.o.) administration, as shown in Table 7. Compound 1-10 at a dose of 3 mg/kg produced a significant increase in PWLs (p<0.01, Bonferroni post-test) that persisted for at least 4 hours post-dosing.

TABLE 7

Attenuation of CFA-induced Thermal Hyperalgesia

| Time (hr) | Attenuation (sec.) by Vehicle alone (p.o.) | Attenuation (sec.) by Ibuprofen (100 mg/kg, p.o.) | Attenuation (sec.) by Compound 1-10 (3 mg/kg, p.o.) |
|---|---|---|---|
| 1 hr | 4.3 ± 0.2 | 7.6 ± 0.7 *** | 6.5 ± 0.5 ** |
| 4 hr | 4.3 ± 0.2 | 7.7 ± 0.6 *** | 6.3 ± 0.3 * |

Values are reported as mean PWLs ± SEM.
A control "Naïve" group without pretreatment registered a PWL of 10.3 ± 0.3 sec.
*, , * denote p < 0.001, 0.01 and 0.05, respectively v. Vehicle (Bonferroni tests).

Example 9

Spinal Nerve Ligation (SNL) Model

The SNL model (Kim and Chung 1992) is used to induce chronic neuropathic pain in rats. Rats are anesthetized with isoflurane, the left L5 transverse process is removed, and the L5 and L6 spinal nerves are tightly ligated with 6-0 silk suture. The wound is then closed with internal sutures and external staples. Following at least seven days post SNL, baseline, post-injury and post-treatment values for non-noxious mechanical sensitivity are evaluated using eight Semmes-Weinstein filaments (Stoelting, Wood Dale, Ill., USA) with varying stiffness (0.4, 0.7, 1.2, 2.0, 3.6, 5.5, 8.5, and 15 g) according to the up-down method (Chaplan et al. 1994). Animals are placed on a perforated metallic platform and allowed to acclimate to their surroundings for a minimum of thirty minutes before testing. The mean and standard error of the mean (SEM) are determined for the injured paw in each treatment group. Since this stimulus is normally not considered painful, significant injury-induced increases in responsiveness in this test are interpreted as a measure of mechanical allodynia. The dose which elicits 50% attenuation of mechanical hypersensitivity ($ED_{50}$) is determined using linear regression analysis.

The texts of the references and U.S. patents cited in this specification are herein incorporated by reference in their entireties. In the event that a definition of a term as incorporated by reference differs from the meaning defined herein, then the meaning provided herein is intended. The examples provided herein are for illustration purposes only and are not to be interpreted as limiting the scope of the invention, the full scope of which will be immediately recognized by those of skill in the art.

What is claimed is:

1. A compound having the structure of formula I:

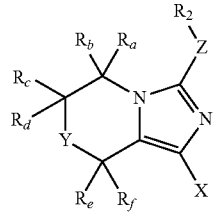

or a pharmaceutically acceptable salt, acid salt, or stereoisomer thereof, wherein:

X is selected from the group consisting of —(CO)$R_1$ and 5-, 6-, 7-, 8-, 9- and 10-membered heterocyclyl;

Y is selected from the group consisting of —$OCR_gR_h$— and —$CR_gR_hO$—;

Z is selected from the group consisting of a bond, —$(CH_2)_p$—, —CH=CH—, —C≡C—, —CONH—; —NHCO— and —CO—;

$R_a$, $R_b$, $R_c$, $R_d$, $R_e$, $R_f$, $R_g$ and $R_h$ are each independently —H or $C_1$-$C_8$ alkyl, $R_1$ is selected from the group consisting of $C_1$-$C_8$ alkyl, $C_2$-$C_8$ alkenyl, aryl, —$NR_5R_6$,

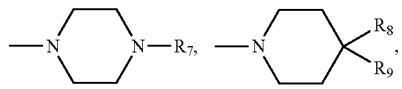

5-, 6-, 7-, 8-, 9- and 10-membered heterocyclyl; wherein the alkyl, alkenyl, aryl and heterocyclyl of $R_1$ are each optionally substituted with one to three substituents independently selected from the group consisting of $C_1$-$C_6$ alkyl, $C_2$-$C_6$ alkenyl, $C_3$-$C_6$ cycloalkyl, $C_1$-$C_6$ alkoxy, aryl, 5-, 6-, and 7-membered heterocyclyl, halo, —OH, —$NH_2$, —CN and —$NO_2$;

$R_2$ is selected from the group consisting of —H, halo, $C_1$-$C_6$ alkyl, $C_2$-$C_6$ alkenyl, $C_2$-$C_6$ alkynyl, $C_3$-$C_{10}$ cycloalkyl, $C_3$-$C_8$ cycloalkenyl, $C_1$-$C_4$ alkoxy, aryl, 5-, 6-, 7-, 8-, 9- and 10-membered heterocyclyl; wherein the alkyl, alkenyl, alkynyl, cycloalkyl, cycloalkenyl, aryl and heterocyclyl of $R_2$ are optionally substituted with one to five substituents independently selected from the group consisting of $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, $C_4$-$C_8$ cycloalkenyl, halo, —OH, —$NH_2$, (A)(A')(A")(A''')aryl, (A)(A')(A")(A''')heterocyclyl, $NR_{14}R_{15}$, $(CH_2)_pNR_{14}R_{15}$, —CN, —$NO_2$, oxo, —$COOR_{14}$, $SOR_{14}$, $SO_2R_{14}$, $SO_2NR_{14}R_{15}$, $NR_{15}SO_2R_{16}$, $COR_{14}$, $CONR_{14}R_{15}$ and $NR_{15}COR_{16}$; wherein (A), (A'), (A") and (A''') are each an independently selected from the group consisting of —H, halo and $C_1$-$C_6$ alkyl and each heterocyclyl of (A)(A')(A")(A''')heterocyclyl is independently selected from the group consisting of 5-, 6-, 7-, 8-, 9- and 10-membered heterocyclyl;

$R_3$ and $R_4$ are each independently selected from the group consisting of —H, $C_1$-$C_6$ alkyl, $C_3$-$C_6$ alkenyl, $C_3$-$C_6$ alkynyl, $C_3$-$C_8$ cycloalkyl, $C_3$-$C_8$ cycloalkenyl, aryl, 5-, 6-, 7- and 8-membered heterocyclyl;

$R_5$ is selected from the group consisting of —H, $C_1$-$C_8$ alkyl and $C_1$-$C_6$ haloalkyl; wherein the alkyl and haloalkyl of $R_5$ are optionally substituted with one to four substituents independently selected from the group consisting of $C_1$-$C_6$ alkoxy, —OH, —$NH_2$, oxo and —CN;

$R_6$ is selected from the group consisting of —H, —$CR_{10}R_{11}R_{12}$, —$CR_{10}R_{11}COR_{13}$, $C_1$-$C_8$ alkyl, $C_3$-$C_{10}$ cycloalkyl, aryl, 5-, 6-, 7-, 8-, 9- and 10-membered heterocyclyl; wherein the alkyl, cycloalkyl, aryl, and heterocyclyl of $R_6$ are optionally substituted with one to three substituents independently selected from the group consisting of $C_1$-$C_6$ alkyl, aryl, halo, —OH, $C_1$-$C_6$ alkoxy, $C_1$-$C_6$ hydroxyalkyl, —$COR_{13}$, —$SO_2R_{11}$, —$SO_2NR_8R_9$, —$NH_2$, —CN and —$NO_2$; alternatively, $R_5$ and $R_6$ taken together with the nitrogen atom to which they are bonded form a heterocyclyl selected from the group consisting of 5-, 6-, 7-, 8-, 9- and 10-membered heterocyclyl, which heterocyclyl substituent of $R_6$ is optionally substituted with one to two substituents independently selected from the group consisting of —$CONR_1R_2$ and oxo;

$R_7$ is selected from the group consisting of —H, $C_1$-$C_6$ alkyl, $C_1$-$C_6$ haloalkyl, —$COR_3$, —$COOR_3$, —$SO_2R_3$, 5-, 6- and 7-membered heterocyclyl;

$R_8$ and $R_9$ are independently selected from the group consisting of —H, $C_1$-$C_6$ alkyl, $C_1$-$C_6$ haloalkyl, $C_1$-$C_6$ alkoxy, $C_2$-$C_6$ alkenyl, $C_3$-$C_6$ cycloalkyl, $C_3$-$C_6$ cycloalkenyl, $(CH_2)_p$aryl, $(CH_2)_p$-linked 5-, 6-, 7-, 8-, 9- and 10-membered heterocyclyl, halo, —OH, —$CONH_2$, —$NH_2$, —CN and —$NO_2$; alternatively: $R_8$ and $R_9$, taken together with the nitrogen atom to which they are bonded form a heterocyclyl ring which is optionally substituted with one to three substituents selected from the group consisting of $C_1$-$C_6$ alkyl, halo, oxo and aryl;

$R_{10}$ is selected from the group consisting of —H and $C_1$-$C_6$ alkyl;

$R_{11}$ is selected from the group consisting of —H, $C_1$-$C_8$ alkyl, $C_2$-$C_6$ alkenyl, $C_2$-$C_6$ alkynyl, $C_3$-$C_{10}$ cycloalkyl, $(CH_2)_p$aryl, $(CH_2)_p$-linked 5-, 6-, 7-, 8-, 9- and 10-membered heterocyclyl; wherein the alkyl, alkenyl, alkynyl, cycloalkyl, aryl and heterocyclyl of $R_{11}$ are optionally substituted with one to three substituents independently selected from the group consisting of $C_1$-$C_4$ alkyl, $C_3$-$C_6$ cycloalkyl, aryl, and 5-, 6-, 7-, 8-, 9- and 10-membered heterocyclyl, halo, —OH, $C_1$-$C_6$ alkoxy, —$NH_2$, -guanidino, —CN, —$NO_2$, oxo, —$COOR_{10}$, —$CONR_8R_9$, —$SO_2NR_8R_9$, —$SR_{10}$, —$SOR_4$ and —$SO_2R_4$;

$R_{12}$ is selected from the group consisting of —H, $C_1$-$C_6$ alkyl and $C_1$-$C_6$ hydroxyalkyl;

$R_{13}$ is selected from the group consisting of —$NR_8R_9$ and —$OR_{10}$;

$R_{14}$, $R_{15}$ and $R_{16}$ are each independently selected from the group consisting of —H, and $C_1$-$C_6$ alkyl; alternatively, $R_{14}$ and $R_{15}$ taken together with the nitrogen atom to which they are bonded form a heterocyclyl selected from the group consisting of 5-, 6-, 7-, 8-, 9- and 10-membered heterocyclyl;

p is an integer from 1 to 6;

provided that:

when Z is a bond, or —CO—, then $R_2$ is not —H.

2. The compound according to claim 1, wherein Z is selected from the group consisting of a bond, —$(CH_2)_p$— and —CO—; and X is —(CO)$R_1$.

3. The compound according to any of claim 1 or 2, wherein Z is selected from the group consisting of a bond and —$(CH_2)_p$—; and $R_1$ is selected from the group consisting of —$NR_5R_6$,

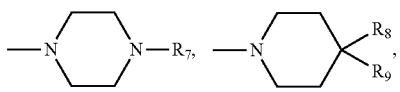

7-, 8-, 9- and 10-membered heterocyclyl; wherein the 7-, 8-, 9- or 10-membered heterocyclyl of $R_1$ is optionally substituted with one to three substituents independently selected from the group consisting of $C_1$-$C_6$ alkyl, halo, —OH, —NH$_2$, —CN and —NO$_2$.

4. The compound according to any of claim 1 or 2, wherein Z is a bond and $R_1$ is —NR$_5$R$_6$; wherein $R_5$ is —H;

$R_6$ is selected from the group consisting of —CR$_{10}$R$_{11}$R$_{12}$ and —CR$_{10}$R$_{11}$COR$_{13}$;

$R_{10}$ is —H;

$R_{11}$ is selected from the group consisting of —H, $C_1$-$C_8$ alkyl, $C_3$-$C_{10}$ cycloalkyl, aryl, 5-, 6-, 7-, 8-, 9- and 10-membered heterocyclyl; wherein the alkyl, cycloalkyl, aryl and heterocyclyl of $R_{11}$ are optionally substituted with one to three substituents independently selected from the group consisting of $C_1$-$C_4$ alkyl, $C_3$-$C_6$ cycloalkyl, aryl, 5-, 6-, 7-, 8-, 9- and 10-membered heterocyclyl, halo, —OH, $C_1$-$C_6$ alkoxy, —NH$_2$, —CN, —NO$_2$, oxo, —COOR$_{10}$, and —CONR$_8$R$_9$;

$R_{12}$ is selected from the group consisting of $C_1$-$C_6$ alkyl and $C_1$-$C_6$ hydroxyalkyl; and $R_{13}$ is —NR$_8$R$_9$.

5. A pharmaceutical composition comprising a compound according to any of claim 1 or 2, and a pharmaceutically acceptable diluent, excipient or carrier.

6. A method of inhibition or treatment of a cannabinoid receptor-associated disease or condition in a mammal, wherein the cannabinoid receptor-associated disease or condition is selected from pain and pruritis, the method comprising administering to the mammal an effective amount of a compound according to claim 1.

7. The method according to claim 6, wherein the cannabinoid receptor-associated disease or condition is pain.

8. The method according to claim 7, wherein the pain is inflammatory pain, visceral pain, somatic pain, neuropathic pain or hyperalgesia.

9. A compound or a pharmaceutically acceptable salt, acid salt, or stereoisomer thereof, selected from the group consisting of:

- (S)—N-(3,3-dimethyl-1-(methylamino)-1-oxobutan-2-yl)-3-phenyl-5,6,8,9-tetrahydroimidazo[1,5-d][1,4]oxazepine-1-carboxamide;
- (S)-3-(3,4-difluorophenyl)-N-(3,3-dimethyl-1-(methylamino)-1-oxobutan-2-yl)-5,6,8,9-tetrahydroimidazo[1,5-d][1,4]oxazepine-1-carboxamide;
- (S)-3-(3,4-difluorophenyl)-N-(3,3-dimethyl-1-(methylamino)-1-oxobutan-2-yl)-5,6,7,9-tetrahydroimidazo[5,1-c][1,4]oxazepine-1-carboxamide;
- (S)-3-(3,4-difluorophenyl)-N-(1-(2-hydroxyethylamino)-3,3-dimethyl-1-oxobutan-2-yl)-5,6,7,9-tetrahydroimidazo[5,1-c][1,4]oxazepine-1-carboxamide;
- (S)-3-(2,5-difluorophenyl)-N-(3,3-dimethyl-1-(methylamino)-1-oxobutan-2-yl)-5,6,7,9-tetrahydroimidazo[5,1-c][1,4]oxazepine-1-carboxamide; and
- (S)-3-(4-chloro-2-fluorophenyl)-N-(3,3-dimethyl-1-(methylamino)-1-oxobutan-2-yl)-5,6,7,9-tetrahydroimidazo[5,1-c][1,4]oxazepine-1-carboxamide.

* * * * *